United States Patent
Sinha et al.

(10) Patent No.: US 9,388,196 B2
(45) Date of Patent: Jul. 12, 2016

(54) THIAZOLE DERIVATIVES AS ALPHA 7 NACHR MODULATORS

(71) Applicant: Lupin Limited, Mumbai, Maharashtra (IN)

(72) Inventors: Neelima Sinha, Pune (IN); Navnath Popat Karche, Pune (IN); Anil Kashiram Hajare, Pune (IN); Shridhar Keshav Adurkar, Pune (IN); Bikramjit Singh Lairikyengbam, Pune (IN); Firoj Aftab Raje, Pune (IN); Ajay Ramchandra Tilekar, Pune (IN); Baban Rupaji Thube, Pune (IN); Venkata P. Palle, Pune (IN); Rajender Kumar Kamboj, Pune (IN)

(73) Assignee: Lupin Limited, Mumbai (IN)

(*) Notice: Subject to any disclaimer, the term of this patent is extended or adjusted under 35 U.S.C. 154(b) by 14 days.

(21) Appl. No.: 14/379,134

(22) PCT Filed: Feb. 22, 2013

(86) PCT No.: PCT/IB2013/051455
§ 371 (c)(1),
(2) Date: Aug. 15, 2014

(87) PCT Pub. No.: WO2013/132380
PCT Pub. Date: Sep. 12, 2013

(65) Prior Publication Data
US 2015/0291617 A1    Oct. 15, 2015

(30) Foreign Application Priority Data

Mar. 6, 2012 (IN) .............................. 235/KOL/2012
Mar. 6, 2012 (IN) .............................. 236/KOL/2012
Mar. 6, 2012 (IN) .............................. 237/KOL/2012
Nov. 12, 2012 (IN) ........................... 1307/KOL/2012

(51) Int. Cl.
| | |
|---|---|
| *A61K 31/5377* | (2006.01) |
| *A61K 31/5386* | (2006.01) |
| *A61K 31/454* | (2006.01) |
| *A61K 31/439* | (2006.01) |
| *A61K 31/427* | (2006.01) |
| *C07D 417/14* | (2006.01) |
| *C07D 417/06* | (2006.01) |
| *C07D 417/04* | (2006.01) |
| *C07D 498/08* | (2006.01) |
| *C07D 277/56* | (2006.01) |
| *C07D 221/22* | (2006.01) |
| *A61K 45/06* | (2006.01) |

(52) U.S. Cl.
CPC ............ *C07D 498/08* (2013.01); *A61K 31/427* (2013.01); *A61K 31/439* (2013.01); *A61K 31/454* (2013.01); *A61K 31/5377* (2013.01); *A61K 31/5386* (2013.01); *A61K 45/06* (2013.01); *C07D 221/22* (2013.01); *C07D 277/56* (2013.01); *C07D 417/04* (2013.01); *C07D 417/06* (2013.01); *C07D 417/14* (2013.01)

(58) Field of Classification Search
CPC .. C07D 417/04; C07D 417/06; C07D 417/14; C07D 498/08; C07D 277/56; C07D 221/22; A61K 31/437; A61K 31/439; A61K 31/454; A61K 31/5377; A61K 31/5386
See application file for complete search history.

(56) References Cited

U.S. PATENT DOCUMENTS

| | | |
|---|---|---|
| 3,953,596 A | 4/1976 | Miller |
| 4,235,871 A | 11/1980 | Papahadjopoulos et al. |

(Continued)

FOREIGN PATENT DOCUMENTS

| | | |
|---|---|---|
| EP | 1012142 B1 | 8/2004 |
| EP | 1489077 A1 | 12/2004 |

(Continued)

OTHER PUBLICATIONS

International Search Report in corresponding International Application No. PCT/IB2012/050806, mailed May 25, 2012.

(Continued)

*Primary Examiner* — Rebecca Anderson
(74) *Attorney, Agent, or Firm* — Leydig, Voit & Mayer, Ltd.

(57) ABSTRACT

Disclosed is a compound of formula (I) wherein Y, Ring D, m and $R^1$-$R^4$ are as described herein, as a modulator of nicotinic acetylcholine receptors particularly the α7 subtype, in a subject in need thereof, as well as pharmaceutically acceptable salts, polymorphs, solvates, and isomers thereofs, for use either alone or in combinations with suitable other medicaments, and pharmaceutical compositions containing such compounds. Also disclosed are a process of preparation of the compounds and the intended uses thereof in therapy, particularly in the prophylaxis and therapy of disorders such as Alzheimer's disease, mild cognitive impairment, senile dementia, and the like.

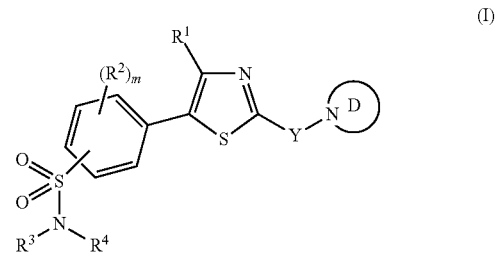

17 Claims, No Drawings

(56) References Cited

U.S. PATENT DOCUMENTS

| | | | |
|---|---|---|---|
| 4,501,728 | A | 2/1985 | Geho et al. |
| 4,837,028 | A | 6/1989 | Allen |
| 5,019,369 | A | 5/1991 | Presant et al. |
| 5,608,082 | A | 3/1997 | Varney et al. |
| 7,683,084 | B2 | 3/2010 | Faghih et al. |
| 7,741,364 | B2 | 6/2010 | Faghih et al. |
| 2003/0236413 | A1 | 12/2003 | Cellier et al. |
| 2005/0080095 | A1 | 4/2005 | Zheng et al. |
| 2006/0142349 | A1 | 6/2006 | Hurst et al. |
| 2006/0258670 | A1 | 11/2006 | Desos et al. |
| 2007/0032531 | A1 | 2/2007 | Smith et al. |
| 2007/0142450 | A1 | 6/2007 | Dahl et al. |
| 2009/0253691 | A1 | 10/2009 | Thuring et al. |
| 2010/0190819 | A1 | 7/2010 | Kanner |
| 2010/0222398 | A1 | 9/2010 | Nardi et al. |
| 2010/0227869 | A1 | 9/2010 | Peters et al. |
| 2010/0240707 | A1 | 9/2010 | Thuring et al. |
| 2010/0298388 | A1 | 11/2010 | Haydon et al. |
| 2013/0331387 | A1 | 12/2013 | Sinha et al. |

FOREIGN PATENT DOCUMENTS

| | | | |
|---|---|---|---|
| EP | | 1790640 A1 | 5/2007 |
| EP | | 1866314 B1 | 9/2010 |
| WO | WO 2004/000792 | A1 | 12/2003 |
| WO | WO 2004/031186 | A1 | 4/2004 |
| WO | WO 2005/030715 | A1 | 4/2005 |
| WO | WO 2005/077932 | A2 | 8/2005 |
| WO | WO 2005/105789 | A2 | 11/2005 |
| WO | WO 2007/031440 | A2 | 3/2007 |
| WO | WO 2007/092751 | A2 | 8/2007 |
| WO | WO 2008/002974 | A1 | 1/2008 |
| WO | WO 2008/057336 | A2 | 5/2008 |
| WO | WO 2008/084300 | A1 | 7/2008 |
| WO | WO 2009/043780 | A1 | 4/2009 |
| WO | WO 2009/043784 | A1 | 4/2009 |
| WO | WO 2009/115547 | A1 | 9/2009 |
| WO | WO 2009/127678 | A1 | 10/2009 |
| WO | WO 2009/127679 | A1 | 10/2009 |
| WO | WO 2009/135944 | A1 | 11/2009 |
| WO | WO 2009/145996 | A2 | 12/2009 |
| WO | WO 2010/120854 | A1 | 10/2010 |
| WO | WO 2010/130768 | A1 | 11/2010 |
| WO | WO 2011/036167 | A1 | 3/2011 |
| WO | WO 2011/064288 | A1 | 6/2011 |
| WO | WO 2012/104782 | A1 | 8/2012 |
| WO | WO 2012/114285 | A9 | 8/2012 |
| WO | WO 2012/131576 | A1 | 10/2012 |
| WO | WO 2013/005153 | A1 | 1/2013 |

OTHER PUBLICATIONS

Albuquerque, E.X., et al., "Modulation of Nicotinic Receptor Activity in the Central Nervous System: A Novel Approach to the Treatment of Alzheimer Disease," *Alzheimer Disease and Associated Disorders*, vol. 15, Suppl. 1, pp. S19-S25 (2001).

Alkondon, Manickavasagom, et al., "α7 Nicotinic acetylcholine receptors and modulation of gabaergic synaptic transmission in the hippocampus," *European Journal of Pharmacology*, vol. 393, pp. 59-67 (2000).

Arias, Hugo R., et al., "Role of non-neuronal nicotinic acetylcholine receptors in angiogenesis," *The International Journal of Biochemistry & Cell Biology*, vol. 41, pp. 1441-1451 (2009).

Avis, Kenneth E., "Parenteral Preparations," *Remington's Pharmaceutical Sciences*, 17th Edition, Chapter 85, Mack Publishing Company, Easton, PA, pp. 1518-1541 (1985).

Bennouna, M., et al., "Cholinergic hypothesis in psychosis following traumatic brain injury and cholinergic hypothesis in schizophrenia: a link?," *L'Encéphale*, vol. 33, pp. 616-620 (Sep. 2007).

Berge, Stephen M., et al., "Pharmaceutical Salts," Review Article form *Journal of Pharmaceutical Sciences*, vol. 66, No. 1, pp. 1-19 (Jan. 1977).

Bitner, Robert S., et al., "Broad-Spectrum Efficacy across Cognitive Domains by α7 Nicotinic Acetylcholine Receptor Agonism Correlates with Activation of ERK1/2 and CREB Phosphorylation Pathways," *The Journal of Neuroscience*, vol. 27, No. 39, pp. 10578-10587 (Sep. 26, 2007).

Boess, Frank G., et al., "The Novel α7 Nicotinic Acetylcholine Receptor Agonist N-[(3R)-1-Azabicyclo[2.2.2]oct-3-yl]-7-[2-(methoxy)phenyl]-1-benzofuran-2-carboxamide Improves Working and Recognition Memory in Rodents," *The Journal of Pharmacology and Experimental Therapeutics*, vol. 321, No. 2, pp. 716-725 (2007).

Bruchfeld, A., et al., "Whole blood cytokine attenuation by cholinergic agonists ex vivo and relationship to vagus nerve activity in rheumatoid arthritis," *Journal of Internal Medicine*, vol. 268, No. 1, pp. 94-101 (Jul. 2010).

Calleja-Macias, Itzel E., "Cholinergic signaling through nicotinic acetylcholine receptors stimulates the proliferation of cervical cancer cells: An explanation for the molecular role of tobacco smoking in cervical carcinogenesis?," *International Journal of Cancer*, vol. 124, pp. 1090-1096 (2009).

Cannon, Tyrone D., "The inheritance of intermediate phenotypes for schizophrenia," *Current Opinion in Psychiatry*, vol. 18, pp. 135-140 (2005).

Carson, Robyn, et al., "Genetic Variation in the α7 Nicotinic Acetylcholine Receptor is Associated with Delusional Symptoms in Alzheimers's Disease," *NeuroMolecular Medicine*, vol. 10, pp. 377-384 (2008).

Chadwick, Derek J., et al., "Esters of Furan-, Thiophen-, and N-Methylpyrrole-2-carboxylix Acids. Bromination of Methyl Furan-2-carboxylate, Furan-2-carbaldehyde, and Thiopen-2-carbaldehyde in the Presence of Aluminum Chloride," *Journal of the Chemical Society, Perkin Transactions 1*, pp. 1766-1773 (1973).

Chan, Wai Kit, et al., "Frontal cortical α7 and α4β2 nicotinic acetylcholinen receptors in working and reference memory," *Neuropharmacology*, vol. 52, pp. 1641-1649 (2007).

Chen, Zheng-Bo, et al., "A Cascade Approach to Pyridines from 2-Azido-2,4-dienoates and α-Diazocarbonyl Compounds," *The Journal of Organic Chemistry*, vol. 74, pp. 903-905 (2009).

Cui, Xinjiang, et al., "Fe(II)-catalyzed N-alkylation of sulfonamides with benzylic alcohols," *Tetrahedron Letters*, vol. 51, pp. 2048-2051 (2010).

Curzon, Peter, et al., "Antisense knockdown of the rat α7 nicotinic acetylcholine receptor produces spatial memory impairment," *Neuroscience Letters*, vol. 410, pp. 15-19 (2006).

Dajas-Bailador, Federico, et al., "Nicotinic acetylcholine receptors and the regulation of neuronal signalling," *TRENDS in Pharmacological Sciences*, vol. 25, No. 6, pp. 317-324 (Jun. 2004).

Damaj, M. Imad, et al., "The antinociceptive effects of α7 nicotinic agonists in an acute pain model," *Neuropharmacology*, vol. 39, pp. 2785-2791 (2000).

Deamici, M., et al., "Analogues of the low-efficacy partial $GABA_A$ agonist 4-PIOL. Synthesis and in vitro pharmacological studies," *European Journal of Medicinal Chemistry*, vol. 26, pp. 625-631 (1991).

Decker, Michael W., et al., "The therapeutic potential of nicotinic acetylcholine receptor agonists for pain control," *Expert Opinion on Investigational Drugs*, vol. 10, No. 10, pp. 1819-1830 (2001).

Deluca, Patrick P., et al., "Parenteral Drug-Delivery Systems," *Pharmaceutics and Pharmacy Practice*, Chapter 8, J.B. Lippincott Company, Philadelphia, PA, pp. 238-250 (1982).

Deng, Wei, et al., "Copper-catalyzed cross-coupling of sulfonamides with aryl iodides and bromides facilitated by amino acid ligands," *Tetrahedron Letters*, vol. 46, pp. 7295-7298 (2005).

Deutsch, Stephen I., et al., "Progressive Worsening of Adaptive Functions in Down Syndrome May be mediated by Complexing of Soluble Aβ Peptides With the $α_7$ Nicotinic Acetylcholine Receptor: Therapeutic Implications," *Clinical Neuropharmacology*, vol. 26, No. 5, pp. 277-283 (2003).

Dong, Huijun, et al., "Transition Metal-Catalyzed Synthesis of Pyrroles from Dienyl Azides," *Organic Letters*, vol. 9, No. 25, pp. 5191-5194 (2007).

Donnelly-Roberts, Diana L., et al., "ABT-594 [(R)-5-(2-Azetidinylmethoxy)-2-Chloropyridine]: A Novel, Orally Effective Analgesic Acting via Neuronal Nicotinic Acetylcholine Receptors: I.

(56) References Cited

OTHER PUBLICATIONS

In Vitro Characterization," *The Journal of Pharmacology and Experimental Therapeutics,* vol. 285. No. 2, pp. 777-786 (1998).

Dunlop, John, et al., "Old and New Pharmacology: Positive Allosteric Modulation of the α7 Nicotinic Acetylcholine Receptor by the 5-Hydroxytryptamne$_{2B/C}$ Receptor Antagonist SB-206553 (3,5-Dihydro-5-methyl-*N*-3-pyridinylbenzo[1,2-*b*:4,5-*b*'] di pyrrole-1-(2*H*)-carboxamide)," *The Journal of Pharmacology and Experimental Therapeutics,* vol. 328, No. 3, pp. 766-776 (2009).

Duris, Kamil, et al, "α7 Nicotinic Acetylcholine Receptor Agonist PNU-282987 Attenuates Early Brain Injury in a Perforation Model of Subarachnoid Hemorrhage in Rats," *Stroke,* vol. 42, pp. 3530-3536 (2011).

Dvornikova, Elena, et al., "Synthesis of 2- and 3-Substituted *N*-Methylpyrroles," *Synlett,* vol. 7, pp. 1152-1153 (2002).

Ebbert, Jon O., et al., "Varenicline for smoking cessation: efficacy, safety, and treatment recommendations," *Patient Preference and Adherence,* vol. 4, pp. 355-362 (2010).

Envivo Pharmaceuticals, "EnVivo Reports Positive Results of Its EVP-6124 Clinical Bio-Marker Study in Schizophrenia Patients," Press Release (Jan. 12, 2009).

Faghih, Ramin, et al., "Discovery of 4-(5-(4-Chlorophenyl)-2-methyl-3-propionyl-1*H*-pyrrol-1-yl)benzenesulfonamide (A-867744) as a Novel Positive Allosteric Modulator of the α7 Nicotinic Acetylcholine Receptor," *Journal of Medicinal Chemistry,* vol. 52, pp. 3377-3384 (2009).

Fehér, Ágnes, et al., "Association between a Genetic Variant of the Alpha-7 Nicotinic Acetylcholine Receptor Subunit and Four Types of Dementia," *Dementia and Geriatric Cognitive Disorders,* vol. 28, pp. 56-62 (2009).

Freedman, Robert, et al., "Evidence in Postmortem Brain Tissue for Decreased Numbers of Hippocampal Nicotinic Receptors in Schizophrenia," *Biological Psychiatry,* vol. 38, pp. 22-33 (1995).

Freedman, Robert, et al., "The Genetics of Sensory Gating Deficits in Schizophrenia," *Current Psychiatry Reports,* vol. 5, pp. 155-161 (2003).

Gallowitsch-Puerta, Margot, et al., "Neuro-immune interactions via the cholinergic anti-inflammatory pathway," *Life Sciences,* vol. 80, No. 24-25, pp. 2325-2329 (May 30, 2007).

Giebelen, Ida A., et al., "Stimulation of α7 Cholinergic Receptors Inhibits Lipopolysaccharide-Induced Neutrophil Recruitment by a Tumor Necrosis Factor α-Independent Mechanism," *Shock,* vol. 27, No. 4, pp. 443-447 (2007).

Goldstein, Richard, et al., "Cholinergic Agonists Inhibit LPS Induced Whole Blood TNF Release Ex Vivo in Patients With Sever Sepsis: A Pilot Study," *Academic Emergency Medicine,* vol. 14, No. 5, Suppl. 1, pp. S185-S186, Abstract 474 (May 2007).

Gupton, John T., et al., "The application of vinylogous iminium salt derivatives to an efficient synthesis of the pyrrole containing alkaloids Rigidin and Rigidin E," *Tetrahedron,* vol. 62, pp. 8243-8255 (2006).

Harrington, C.R., et al., "Senile Dementia of Lewt Body Type and Alzheimer Type are Biochemically Distinct in Terms of Paired Helical Filaments and Hyperphosphorylated Tau Protein," *Diementia,* vol. 5, pp. 215-228 (1994).

Hashimoto, Kenji, et al., "Phencyclidine-Induced Cognitive Deficits in Mice are Improved by Subsequent Subchronic Administration of the Novel Selective α7 Nicotinic Receptor Agonist SSR180711," *Biological Psychiatry,* vol. 63, pp. 92-97 (2008).

Hauser, T.A., et al., "TC-5619: An alpha7 neuronal nicotinic receptor-selective agonist that demonstrates efficacy in animal models of the positive and negative symptoms and cognitive dysfunction of schizophrenia," *Biochemical Pharmacology,* vol. 78, No. 7, pp. 803-812 (Oct. 1, 2009).

Haydar, Simon N., et al., "SAR and biological evaluation of SEN12333/WAY-317538: Novel alpha 7 nicotinic acetylcholine receptor agonist," *Bioorganic & Medicinal Chemistry,* vol. 17, pp. 5247-5258 (2009).

Heeschen, Christopher, et al., "A novel angiogenic pathway mediated by non-neuronal nicotinic acetylcholine receptors," *The Journal of Clinical Investigation,* vol. 110, No. 4, pp. 527-536 (Aug. 2002).

Imamura, Yorishige, et al., "Catalytic Properties of Carbonyl Reductase from Rabbit Kidney for Acetohexamide and Its Analogs," *Bioorganic Chemistry,* vol. 22, pp. 387-394 (1994).

Jeyarasasingam, G., et al., "Stimulation of Non-α7 Nicotinic Receptors Partially Protects Dopaminergic Neurons From 1-Methyl-4-Phenylpyridinium-Induced Toxicity in Culture," *Neuroscience,* vol. 109, No. 2, pp. 275-285 (2002).

Jin, Y., et al., "Genomic polymorphism within alpha 7 nicotinic acetylcholine receptor and severe sepsis in Chinese Han Population," *International Journal of Immunogenetics,* vol. 37, pp. 361-365 (2010).

Karshtedt, Dmitry, et al., "Plabrium-Based Catalysts for the Hydroamination of Olefins with Sulfonamides and Weakly Basic Anilines," *Journal of the American Chemical Society,* vol. 127, pp, 12640-12646 (2005).

Kaur, Kirendeep, et al., "Design, synthesis and activity of novel derivatives of Oxybutynin and Tolterodine," *Bioorganic & Medicinal Chemistry Letters,* vol. 15, pp. 2093-2096 (2005).

Kawamorita, Soichiro, et al., "Ester-Directed Regioselective Borylation of Heteroarenes Catalyzed by a Silica-Supported Iridium Complex," *The Journal of Organic Chemistry,* vol. 75, pp. 3855-3858 (2010).

Kuzmin, Alexander, et al., "Effects of subunit selective nACh receptors on operant ethanol self-administration and relapse-like ethanol-drinking behavior," *Psychopharmacology,* vol. 203, pp. 99-108 (2009).

Lee, Sang-Hyeup,et al., "The direct conversion of carbamates to ureas using aluminum amides," *Tetrahedron,* vol. 60, pp. 3439-3443 (2004).

Leiser, Steven C., et al., "A cog in cognition: How the α7 nicotinic acetylcholine receptor is geared towards improving cognitive defects," *Pharmacology & Therapeutics,* vol. 122, No. 3, pp. 302-311 (Jun. 2009).

Leonard, S., et al.' "Smoking and mental illness" *Pharmacology, Bochemistry and Behavior,* vol. 70, pp. 561-570 (2001).

Letellier, Marie-Anne, et al., "Synthesis of potential Rho-kinase inhibitors based on the chemistry of an original heterocycle: 4,4-Dimethyl-3,4-dihydro-1*H*-quinolin-2-one," *European Journal of Medicinal Chemistry,* vol. 43, pp. 1730-1736 (2008).

Liu, Chong, et al., "Antishock effect of anisodamine involves a novel pathway for activating α7 nicotinic acetylcholine receptor," *Critical Care Medicine,* vol. 37, No. 2, pp. 634-641 (2009).

Luo, Fan, et al., "Highly enantioselective bioreduction of 2-fluorocinnamyl alcohols mediated by *Saccharomyces cerevisiae,*" *Tetrahedron Letters,* vol. 51, pp. 1693-1695 (2010).

Mansvelder, Huibert D., et al., "Nicotinic modulation of neuronal networks: from receptors to cognition," *Psychopharmacology,* vol. 184, pp. 292-305 (2006).

Marrero, Mario B., et al., "Convergence of alpha 7 nicotinic acetylcholine receptor-activated pathways for anti-apoptosis and anti-inflammation: Central role for JAK2 activation of STAT3 and NF-κB," *Brain Research,* vol. 1256, pp. 1-7 (2009).

Martin, Laura F., et al., "Sensory Gating and Alpha-7 Nicotinic Receptor Gene Allelic Variants in Schizoaffective Disorder, Bipolar Type," *American Journal of Medical Genetics Part B: Neuropsychiatric Genetics,* vol. 144B, No. 5, pp. 611-614 (Jul. 5, 2007).

Martin, Laura F., et al., "Alpha-7 nicotinic receptor agonists: potential new candidates for the treatment of schizophrenia," *Psychopharmacology,* vol. 174, pp. 54-64 (2004).

McKay, Bruce E., et al., "Regulation of synaptic transmission of plasticity by neuronal nicotinic acetylcholine receptors," *Biochemical Pharmacology,* vol. 74, pp. 1120-1133 (2007).

Miyaura, Norio, et al., "Palladium-Catalyzed Cross-Coupling Reactions of Organoboron Compounds," *Chemical Reviews,* vol. 95, pp. 2457-2483 (1995).

Nagele, R.G., et al., "Intracellular Accumulation of β-Amyloid$_{1-42}$ in Neurons is Facilitated by the α7 Nicotinic Acetycholine Receptor in Alzheimer's Disease," *Neuroscience,* vol. 110, No. 2, pp. 199-211 (2002).

(56) References Cited

OTHER PUBLICATIONS

Nakano, Jun, et al., "Studies on Ketene and Its Derivatives. CX.[1]) Synthesis of 1,3-Dimethoxyfluoren-9-ones," *Chemical and Pharmaceutical Bulletin*, vol. 30, No. 7, pp. 2590-2594 (1982).

Ng, Herman J., et al., "Nootropic α7 nicotinic receptor allosteric modulator derived from $GABA_A$ receptor modulators," *Proceedings of the National Academy of Sciences*, vol. 104, No. 19, pp. 8059-8064 (May 8, 2007).

Nishio, Takehiko, "Sulfur-Containing Heterocycles Derived by Reaction of ω-Keto Amides with Lawesson's Reagent," *Helvetica Chimica Acta*, vol. 81, pp. 1207-1214 (1998).

Nizri, Eran, et al., "The Role of Cholinergic Balance Perturbation in Neurological Diseases," *Drug News & Perspectives*, vol. 20, No. 7, pp. 421-429 (Sep. 2007).

Nordberg, Agneta, et al., "Neuroprotection in Alzheimer's Disease—New Strategies for Treatment," *Neurotoxicity Research*, vol. 2, pp. 157-165 (2000).

O'Donnell, Christopher J., et al., "Discovery of 4-(5-Methyloxazolo[4,5-b]pyridine-2-yl)-1,4-diazabicyclo[3.2.2]nonane (CP-810,123), a Novel α7 Nicotinic Acetylcholine Receptor Agonist for the Treatment of Cognitive Disorders in Schizophrenia: Synthesis, SAR Development, and in Vivo Efficacy in Cognition Models," *Journal of Medicinal Chemistry*, vol. 53, pp. 1222-1237 (2010).

Olincy, Ann, et al., "Proof-of-Concept Trial of an α7 Nicotinic Agonist in Schizophrenia," *Archives of General Psychiatry*, vol. 63, pp. 630-638 (Jun. 2006).

Olincy, Ann, "Nicotine Receptor Dysfunction in Schizophrenia and Therapeutic Effects of Nicotine Agonist DMXBA," *Biological Psychiatry*, vol. 57, p. 13S, Abstract No. 44 (2005).

Pan, Changduo, et al., "$Cu(OAc)_2$-Catalyzed N-Arylation of Sulfonamides with Arylboronic Acids or Trimethoxy(phenyl)silane," *Synthetic Communications*, pp. 2082-2092 (2009).

Paterson, David, et al., "Neuronal nicotinic receptors in the human brain," *Progress in Neurobiology*, vol. 61, pp. 75-111 (2000).

Peña, Geber, et al., "Unphosphorylated STAT3 modulates alpha7 nicotinic receptor signaling and cytokine production in sepsis," *European Journal of Immunology*, vol. 40, No. 9, pp. 2580-2589 (Sep. 2010).

Peng, ZZ, et al., "The transmission of disequilibrium analysis between neuronal nicotinic acetylcholine receptor alpha 7 subunit gene polymorphisms and schizophrenia," *Zhonghua Yi Xue Yi Chuan Xue Za Zhi*, vol. 25, No. 2, pp. 154-158 (Apr. 2008).

Perry, Elaine, et al., "Nicotinic receptor subtypes in human brain ageing, Alzheimer and Lewy body diseases," *European Journal of Pharmacology*, vol. 393, pp. 215-222 (2000).

Pichat, Philippe, et al., "SSR180711, a Novel Selective α7 Nicotinic Receptor Partial Agonist: (II) Efficacy in Experimental Models Predictive of Activity Against Cognitive Symptoms of Schizophrenia," *Neuropsychopharmacology*, vol. 32, pp. 17-34 (2007).

"Product Identification Guide," *Physicians' Desk Reference*, 58th Edition, Thomson PDR, Montvale, NJ, pp. 303-340 (2004).

"Product Information—Eisai," *Physicians' Desk Reference*, 58th Edition, Thomson PDR, Montvale, NJ, pp. 1221-1223 (2004).

"Product Information—Janssen," *Physicians' Desk Reference*, 58th Edition, Thomson PDR, Montvale, NJ, pp. 1759-1764 (2004).

"Product Information—Novartis Pharmaceuticals," *Physicians' Desk Reference*, 58th Edition, Thomson PDR, Montvale, NJ, pp. 2252-2259 (2004).

"Product Information—Pfizer," *Physicians' Desk Reference*, 58th Edition, Thomson PDR, Montvale, NJ, pp. 2570-2573 (2004).

Redrobe, John P., et al., "α7 nicotinic acetylcholine receptor activation ameliorates scopolamine-induced behavioural changes in a modified continuous Y-maze task in mice," *European Journal of Pharmacology*, vol. 602, pp. 58-65 (2009).

Remingtons' Pharmaceutical Sciences, 18th Edition, p. 1445 (1990).

Richardson, Christine M., et al., "Discovery of a potent CDK2 inhibitor with a novel binding mode, using virtual screening and initial, structure-guided lead scoping," *Bioorganic & Medicinal Chemistry Letters*, vol. 17, pp. 3880-3885 (2007).

Roger, Julien, et al., "Regioselective C-2 or C-5 Direct Arylation of Pyrroles with Aryl Bromides using a Ligand-Free Palladium Catalyst," *Advanced Synthesis & Catalysis*, vol. 351, pp. 1977-1990 (2009).

Roncarati, Renza, et al., "Procognitive and Neuroprotective Activity of a Novel α7 Nicotinic Acetylcholine Receptor Agonist for Treatment of Neurodegenerative and Cognitive Diseases," *The Journal of Pharmacology and Experimental Therapeutics*, vol. 329, No. 2, pp. 459-468 (2009).

Rosas-Ballina, M., et al., "Cholinergic control of inflammation," *Journal of Internal Medicine*, vol. 265, pp. 663-679 (2009).

Rosas-Ballina, Mauricio, et al., "The Selective α7 Agonist GTS-21 Attenuates Cytokine Production in Human Whole Blood and Human Monocytes Activated by Ligands of TLR2, TLR3, TLR4, TLR9, and RAGE," *Molecular Medicine*, vol. 15, No. 7-8, pp. 195-202 (Jul.-Aug. 2009).

Rowbotham, Michael C., et al., "A randomized, double-blind, placebo-controlled trial evaluating the efficacy and safety of ABT-594 in patients with diabetic peripheral neuropathic pain," *Pain*, vol. 146, pp. 245-252 (2009).

Rowley, T.J., et al., "Antinociceptive and anti-inflammatory effects of choline in a mouse model of postoperative pain," *British Journal of Anaesthesia*, vol. 105, No. 2, pp. 201-207 (2010).

Rubboli, F., et al., "Distribution of Neuronal Nicotinic Receptor Subunits in Human Brain," *Neurochemistry International*, vol. 25, No. 1, pp. 69-71 (1994).

Sanberg, Paul R., et al., "Nicotine for the Treatment of Tourette's Syndrome," *Pharmacology & Therapeutics*, vol. 74, No. 1, pp. 21-25 (1997).

Schulller, Hildegard M., et al., "Interaction of tobacco-specific toxicants with neuronal $α_7$ nicotinic acetylcholine receptor and its associated mitogenic signal transduction pathway: potential role in lung carcinogenesis and pediatric lung disorders," *European Journal of Pharmacology*, vol. 393, pp. 265-277 (2000).

Solinas, Marcello, et al., "Nicotinic $α_7$ Receptors as a New Target for Treatment of Cannabis Abuse," *The Journal of Neuroscience*, vol. 27, No. 21, pp. 5615-5620 (May 23, 2007).

Stahl, P. Heinrich, et al., *Handbook of Pharmaceutical Salts: Properties, Selection, and Use*, Wiley-VCH, Weinheim, pp. 1-374 (2002).

Suemaru, K. et al., "Involvement of neuronal nicotinic receptor in psychiatric disorders," *Nihon Yakurigaku Zasshi*, vol. 119, No. 5, pp. 295-300 (May 2002).

Szoka, Jr., Francis, et al., "Comparative Properties and Methods of Preparation of Lipid Vesicles (Liposomes)," *Annual Review of Biophysics & Bioengineering*, vol. 9, pp. 467-508 (1980).

Taguchi, Kazuhiko, et al., "Synthesis of quinolines from amino alcohol and ketones catalyzed by $[IrCl(cod)]_2$ or $IrCl_3$ under solvent-free conditions," *Tetrahedron Letters*, vol. 46, pp. 4539-4542 (2005).

Tatsumi, Ryo, et al., "(+)-3-[2-(Benzo[b]thiophen-2-yl)-2-oxoethyl]1-azabicyclo[2.2.2]-octane as potent agonist for the α7 nicotinic acetylcholine receptor," *Bioorganic & Medicinal Chemistry Letters*, vol. 14, pp. 3781-3784 (2004).

Tatsumi, Ryo, et al., "(R)-3'-(3-Methylbenzo[b]thiophen-5-yl)spiro[1-azabicyclo[2,2,2]octane-3,5'-oxazolidin]-2'-one, a Novel and Potent α7 Nicotinic Acetylcholine Receptor Partial Agonist Displays Cognitive Enhancing Properties," *Journal of Medicinal Chemistry*, vol. 49, pp. 4374-4383 (2006).

Thomsen, Morten S., et al., "Cognitive Improvement by Activation of $α_7$ Nicotinic Acetylcholine Receptors: From Animal Models to Human Pathophysiology," *Current Pharmaceutical Design*, vol. 16, pp. 323-343 (2010).

Timmermann, Daniel B., et al., "An Allosteric Modulators of the α7 Nicotinic Acetylcholine Receptor Possessing Cognition-Enhancing Properties in Vivo," *The Journal of Pharmacology and Experimental Therapeutics*, vol. 323, No. 1, pp. 294-307 (2007).

Trissel, Lawrence A., "Intravenous Infusion Solutions," *ASHP Handbok on Injectable Drugs*, Fourth Edition, American Society of Hospital Pharmacists, Inc., Bethesda, MD, pp. 622-630 (1986).

Tsuang, Debby W., et al., "Examination of Genetic Linkage of Chromosome 15 to Schizophrenia in a Large Veterans Affairs Cooperative Study Sample," *American Journal of Medical Genetics (Neuropsychiatric Genetics)*, vol. 105, pp. 662-668 (2001).

(56) References Cited

OTHER PUBLICATIONS

Tusco, Salvatore J., et al., "Intravenous Admixtures," *Remington's Pharmaceutical Sciences*, 17th Edition, Chapter 86, Mack Publishing Company, Easton, PA, pp. 1542-1552 (1985).

Van Kampen, Marja, et al., "AR-R 17779 improves social recognition in rats by activation of nicotinic $\alpha_7$ receptors," *Psychopharmacology*, vol. 174, pp. 375-383 (2004).

Verbois, S.L., et al. "Chronic nicotine treatment attenuates α7 nicotinic receptoir deficits following traumatic brain injury," *Neuropharmacology*, vol. 44, pp. 224-233 (2003).

Wang, Hoau-Yan, et al., "Dissociating β-Amyloid from α7 Nicotinic Acetylcholine Receptor by a Novel Therapeutic Agent, S 24795, Normalizes α7 Nicotinic Acetylcholine and NMDA Receptor Function in Alzheimer's Disease Brain," *The Journal of Neuroscience*, vol. 29, No. 35, pp. 10961-10973 (Sep. 2, 2009).

Wang, Juan, et al., "Huperzine A Improves Chronic Inflammation and Cognitive Decline in Rats With Cerebral Hypoperfusion," *Journal of Neuroscience Research*, vol. 88, pp. 807-815 (2010).

Wasserman, Todd H., et al., "Clinical Comparison of the Nitrosoureas," *Cancer*, vol. 36, pp. 1258-1268 (1975).

Weiss, Robert B., et al., "A Candidate Gene Approach identifies the CHRNA5-A3-B4 Region as a Risk Factor for Age-Dependent Nicotine Addition," *PLoS Genetics*, vol 4, No. 7, e1000125, pp. 1-11 (Jul. 2008).

Westman, M., et al., "Cell Specific Synovial Expression of Nicotinic Alpha 7 Acetylcholine Receptor in Rheumatoid Arthritis and Psoriatic Arthritis," *Scandinavian Journal of Immunology*, vol. 70, pp. 136-140 (2009).

Wilens, Timothy E., et al., "Neuronal Nicotinic Receptor Agonists for the Treatment of Attention-Deficit/Hyperactivity Disorder: Focus on Cognition," *Biochemical Pharmacology*, vol. 74, No. 8, pp. 1212-1223 (Oct. 15, 2007).

Xu, Liang, et al., "Oxidative cyclization of N-alkyl-*o*-methyl-arenesulfonamides to biologically important saccharin derivatives," *Tetrahedron*, vol. 62, pp. 7902-7910 (2006).

Yang, Lei, et al., "Heteropoly acids: a green and efficient heterogeneous Bronsted acidic catalyst for the intermolecular hydroamination of olefins," *Tetrahedron Letters*, vol. 49, pp. 2882-2885 (2008).

Young, Jared W., et al., "Impaired attention is central to the cognitive deficits observed in alpha 7 deficient mice," *European Neuropsychopharmacology*, vol. 17, pp. 145-155 (2007).

Young, Jared W., et al., "Nicotine Improves Sustained Attention in Mice: Evidence for involvement of the α7 Nicotinic Acetylcholine Receptor," *Neuropsychopharmacology*, vol. 29, pp. 891-900 (2004).

Zhao, Xilong, et al., "Post-Stroke Dementia: Nootropic Drug Modulation of Neuronal Nicotinic Acetylcholine Receptors," *Annals New York Academy of Sciences*, vol. 939, pp. 179-186 (2001).

U.S. Appl. No. 14/894,803, filed Nov. 30, 2015.

THIAZOLE DERIVATIVES AS ALPHA 7 NACHR MODULATORS

CROSS-REFERENCE TO RELATED APPLICATIONS

The present application is the U.S. national stage of PCT/IB2013/051455, filed Feb. 22, 2013, which claims the benefit of Indian Provisional Patent Application Nos. 0235/KOL/2012 filed on 6 Mar. 2012, 0236/KOL/2012 filed on 6 Mar. 2012, 0237/KOL/2012 filed on 6 Mar. 2012, and 1307/KOL/2012 filed on 12 Nov. 2012, the disclosures of which are incorporated herein by reference in their entirety.

FIELD OF THE INVENTION

The present invention relates to thiazole derivatives, their tautomeric forms, their stereoisomers, and their pharmaceutically acceptable salts, pharmaceutical compositions comprising one or more such compounds, and their use as nicotinic acetylcholine receptor α7 subunit (α7 nAChR) modulator.

BACKGROUND OF THE INVENTION

Cholinergic neurotransmission, mediated primarily through the neurotransmitter acetylcholine (ACh), is a predominant regulator of the physiological functions of the body via the central and autonomic nervous system. ACh acts on the synapses of the neurons present in of all the autonomic ganglia, neuromuscular junctions and the central nervous system. Two distinct classes of ACh target receptors viz. muscarinic (mAChRs) and the nicotinic (nAChRs) have been identified in brain, forming a significant component of receptors carrying its mnemonic and other vital physiological functions.

Neural nicotinic ACh receptors (NNRs) belong to the class of ligand-gated ion channels (LGIC) comprising of five subunits (α2-α10, β2-β4) arranged in heteropentameric (α4β2) or homopertameric (α7) configuration (Paterson D, et al., Prog. Neurobiol., 2000, 61, 75-111). α4β2 and α7 nAChR constitute the predominant subtypes expressed in the mammalian brain. α7 nAChR has attained prominence as a therapeutic target due to its abundant expression in the learning and memory centers of brain, hippocampus and the cerebral cortex (Rubboli F, et al., Neurochem. Int., 1994, 25, 69-71). Particularly, α7 nAChR is characterized by a high $Ca^{2+}$ ion permeability, which is responsible for neurotransmitter release and consequent modulation of excitatory and inhibitory neurotransmission (Alkondon M, et al., Eur. J. Pharmacol., 2000, 393, 59-67; Dajas-Bailador F, et al., Trends Pharmacol. Sci., 2004, 25, 317-324). Furthermore, high $Ca^{2+}$ ion influx also has implications on the long-term potentiation of memory via alterations in gene expression (Bitner R S, et al., J. Neurosci., 2007, 27, 10578-10587; McKay B E, et al., Biochem. Pharmacol., 2007, 74, 1120-1133).

Several recent studies have confirmed the role of α7 nAChR in neural processes like attention, memory and cognition (Mansvelder H D, et al., Psychopharmacology (Berl), 2006, 184, 292-305; Chan W K, et al., Neuropharmacology, 2007, 52, 1641-1649; Young J W, et at, Eur. Neuropsychopharmacol., 2007, 17, 145-155). Gene polymorphisms associated with the α7 nAChR protein CHRNA7 have been implicated in the genetic transmission of schizophrenia, related neurophysiological sensory gating deficits and resultant cognitive impairment (Freedman R, et al., Biol. Psychiatry, 1995, 38, 22-33; Tsuang D W, et al., Am. J. Med. Genet., 2001, 105, 662-668). Also, preclinical studies in α7 nAChR knock-out and anti-sense oligonucleotide treated mice have demonstrated impaired attention and defective cognition underscoring the prominent role of α7 nAChR in cognition (Curzon P, et al., Neurosci. Lett., 2006, 410, 15-19; Young J W, et al., Neuropsychopharmacology., 2004, 29, 891-900). Additionally, pharmacological blockade of α7 nAChR impairs memory and its activation enhances same in preclinical rodent models implicating α7 nAChR as target for cognitive enhancement (Hashimoto K, et al., Biol. Psychiatry, 2008, 63, 92-97).

Pathological brain function in sensory-deficit disorders has been associated with nicotinic cholinergic transmission particularly through α7 receptors (Freedman R, et al., Biol. Psychiatry, 1995, 38, 22-33; Tsuang D W, et al., Am. J. Med. Genet., 2001, 105, 662-668; Carson R, et al., Neuromolecular, 2008, Med. 10, 377-384; Leonard S, et al., Pharmacol. Biochem. Behav., 2001, 70, 561-570; Freedman R, et al., Curr. Psychiatry Rep., 2003, 5, 155-161; Cannon T D, et al., Curr. Opin. Psychiatry, 2005, 18, 135-140). A defective pre-attention processing of sensory information is understood to be the basis of cognitive fragmentation in schizophrenia and related neuropsychiatric disorders (Leiser S C, et al., Pharmacol. Ther., 2009, 122, 302-311). Genetic linkage studies have traced sharing of the α7 gene locus for several affective, attention, anxiety and psychotic disorders (Leonard S, et al., Pharmacol. Biochem. Behav., 2001, 70, 561-570; Suemaru K, et al., Nippon Yakurigaku Zasshi, 2002, 119, 295-300).

Perturbations in the cholinergic and glutamatergic homeostasis, has long been implicated as causative factors for host of neurological disease, including dementia(s) (Nizri E, et al., Drug News Perspect., 2007, 20, 421-429). Dementia is a severe, progressive, multi-factorial cognitive disorder affecting memory, attention, language and problem solving. Nicotinic ACh receptor, particularly the interaction of α7 receptor to $\alpha\beta_{1-42}$ is implicated as an up-stream pathogenic event in Alzheimer's disease, a major causative factor for dementia (Wang H Y, et al., J. Neurosci., 2009, 29, 10961-10973). Moreover, gene polymorphisms in CHRNA7 have been implicated in dementia with lewy bodies (DLB) and Pick's disease (Feher A, et al., Dement. Geriatr. Cogn. Disord., 2009, 28, 56-62).

Disease modification potential of nAChRs particularly the α7 receptor has application for disease-modification of Alzheimer's disease (AD) and Parkinson's disease (PD) by enhancing neuron survival and preventing neurodegeneration (Wang et al. 2009; Nagele R G, et al., Neuroscience, 2002, 110, 199-211; Jeyarasasingam G, et al., Neuroscience, 2002, 109, 275-285). Additionally, α7 nAChR induced activation of anti-apoptotic (BCL-2) and anti-inflammatory pathways in brain could have neuroprotective effects in neurodegenerative diseases (Marrero M B, et al., Brain. Res., 2009, 1256, 1-7). Dopamine containing neurons of ventral tegmental area (VTA) and laterodorsal tegmental nucleus (LDT) are known to express nicotinic ACh receptors, particularly α4, α3, β2, β3, β4 subunits (Kuzmin A, et al., Psychopharmacology (Berl), 2009, 203, 99-108). Nicotinic ACh receptors, α4β2 and α3β4 have been identified with candidate-gene approach to have strong mechanistic link for nicotine addiction (Weiss R B, et al., PLoS Genet., 2008, 4, e1000125). α7 nAChR has particularly been studied for a putative role in *cannabis* addiction (Solinas M. et al., J. Neurosci., 2007, 27, 5615-5620). Vareniciline, a partial agonist at α4β2, has demonstrated better efficacy in reducing the smoking addiction and relapse prevention in comparison to buproprion (Ebbert J O, et al., Patient. Prefer. Adherence, 2010, 4, 355-362).

Presence of a high-affinity nicotine binding site at α4β2 nAChR, in the descending inhibitory pathways from brainstem has sparked interest in the antinociceptive properties of nicotinic ACh receptor agonists like epibatidine (Decker M W, et al., Expert. Opin. Investig. Drugs, 2001, 10, 1819-1830). Several new developments have opened the area for use of nicotinic modulators for therapy of pain (Rowbotham M C, et al., Pain, 2009, 146, 245-252). Appropriate modulation of the nicotinic ACh receptors could provide for remedial approach to pain related states.

Another key role of the α7 nAChR is the ability to modulate the production of pro-inflammatory cytokines, like interleukins (IL), tumor necrosis factor alpha (TNF-α), and high mobility group box (HMGB-1) in the central nervous system. Consequently, an anti-inflammatory and antinociceptive effect in pain disorders have been demonstrated (Damaj M I, et al., Neuropharmacology, 2000, 39, 2785-2791). Additionally, 'cholinergic anti-inflammatory pathway' is proposed to be a regulatory of local and systemic inflammation and neuro-immune interactions through neural and humoral pathways (Gallowitsch-Puerta M, et al., Life Sci., 2007, 80, 2325-2329; Gallowitsch-Puerta and Pavlov 2007; Rosas-Ballina M, et al., Mol. Med., 2009, 15, 195-202; Rosas-Ballina M, et al., J. Intern. Med., 2009, 265, 663-679). Selective modulators of nicotinic ACh receptors, particularly α7 type, like GTS-21, attenuate cytokine production and IL-1β after endotoxin exposure. Furthermore, α7 nAChR are understood to have a central role in arthritis pathogenesis and potential therapeutic strategy for treatment of joint inflammation (Westman M. et al., Scand. J. Immunol., 2009, 70, 136-140). A putative role for α7 nAChR has also been implicated in severe sepsis, endotoxemic shock and systemic inflammation (Jin Y. et al. (2010) Int. J. Immunogenet., Liu C, et al., Crit. Care. Med., 2009, 37, 634-641).

Angiogenesis, is a critical physiological process for the cell survival and pathologically important for cancer proliferation; several non-neural nicotinic ACh receptors, particularly α7, α5, α3, β2, β4, are involved (Arias H R, et al., Int. J. Biochem. Cell. Biol., 2009, 41, 1441-1451; Heeschen C, et al., J. Clin. Invest., 2002, 110, 527-536). A role of nicotinic ACh receptors in the development of cervical cancer, lung carcinogenesis and paediatric lung disorders in smoking-exposed population has also been studied (Calleja-Macias I E, et al., Int. J. Cancer., 2009, 124, 1090-1096; Schuller H M, et al., Eur. J. Pharmacol., 2000, 393, 265-277). Several α7 nAChR agonists, partial agonists, have been characterized for their efficacy in clinical and preclinical studies. EVP-6124, an agonist at α7 nAChR, has demonstrated significant improvement in sensory processing and cognition biomarkers in Phase Ib study with patients suffering from schizophrenia (EnVivo Pharmaceuticals press release 2009, Jan. 12). GTS-21 (DMXB-Anabaseine), an α7 nAChR agonist, in the P II clinical trials, has shown efficacy in improving cognitive deficits in schizophrenia and inhibition of endotoxin-induced TNF-α release (Olincy A, et al., Biol. Psychiatry, 2005, 57(8, Suppl.), Abst 44; Olincy A, et al., Arch. Gen. Psychiatry, 2006, 63, 630-638; Goldstein R, et al., Acad. Emerg. Med., 2007, 14 (15, Suppl. 1), Abst 474). CP-810123, a α7 nAChR agonist, exhibits protection against the scopolamine-induced dementia and inhibition of amphetamine-induced auditory evoked potentials in preclinical studies (O'Donnell C J, et al., J. Med. Chem., 2010, 53, 1222-1237). SSR-180711A, also an α7 nAChR agonist, enhances learning and memory, and protects against MK-801/Scopolamine-induced memory loss and prepulse inhibition in preclinical studies (Redrobe J P, et al., Eur. J. Pharmacol., 2009, 602, 58-65; Dunlop J, et al., J. Pharmacol. Exp. Ther., 2009, 328, 766-776; Pichat P, et al., Neuropsychopharmacology, 2007, 32, 17-34). SEN-12333, protected against scopolamine-induced amnesia in passive avoidance test in preclinical studies (Roncarati R, et al., J. Pharmacol. Exp. Ther., 2009, 329, 459-468). AR-R-17779, an agonist at α7 nAChR, exhibits improvement in the social recognition task performed in rats (Van K M, et al., Psychopharmacology (Berl), 2004, 172, 375-383). ABBF, an agonist at α7 nAChR, improves social recognition memory and working memory in Morris maze task in rats (Boess F G, et al., J. Pharmacol. Exp. Ther., 2007, 321, 716-725). TC-5619, a selective α7 nAChR agonist has demonstrated efficacy in animal models of positive and negative symptoms and cognitive dysfunction in schizophrenia (Hauser T A, et al., Biochem. Pharmacol., 2009, 78, 803-812).

An alternative strategy to reinforce or potentiate the endogenous cholinergic neurotransmission of ACh without directly stimulating the target receptor is the positive allosteric modulation (PAM) of α7 nAChR (Albuquerque E X, et al., Alzheimer Dis. Assoc. Disord., 2001, 15 Suppl 1, S19-S25). Several PAMs have been characterized, albeit in the preclinical stages of discovery. A-86774, α7 nAChR PAM, improves sensory gating in DBA/2 mice by significantly reducing the T: C ratio in a preclinical model of schizophrenia (Faghih R, et al., J. Med. Chem., 2009, 52, 3377-3384). XY-4083, an α7 nAChR PAM, normalizes the sensorimotor gating deficits in the DBA/2 mice and memory acquisition in 8-arm radial maze without altering the receptor desensitization kinetics (Ng H J, et al., Proc. Natl. Acad. Sci., U.S.A., 2007, 104, 8059-8064). Yet another PAM, PNU-120596, profoundly alters α7 nAChR desensitization kinetics and simultaneously protecting against the disruption of prepulse inhibition by MK-801. NS-1738, another PAM, has exhibited efficacy in-vivo in the animal models of social recognition and spatial memory acquisition in the Morris maze task (Timmermann D B, et al., J. Pharmacol. Exp. Ther., 2007, 323, 294-307). In addition, several patents/applications published are listed below—US 2006/0142349, US 2007/0142450, US 2009/0253691, WO 2007/031440, WO 2009/115547, WO 2009/135944, WO 2009/127678, WO 2009/127679, WO 2009/043780, WO 2009/043784, U.S. Pat. Nos. 7,683,084, 7,741,364, WO 2009/145996, US 2010/0240707, WO 2011/064288, US 2010/0222398, US 2010/0227869, EP 1866314, WO 2010/130768, WO 2011/036167, US 2010/0190819, WO 2012/104782, WO 2012/114285, WO 2012/131576, WO 2013/005153 disclose efficacy of allosteric modulators of nicotinic ACh receptors and underscoring their therapeutic potential.

BRIEF SUMMARY OF THE INVENTION

The present invention provide compounds of the general formula I, its tautomeric forms, its stereoisomers, its pharmaceutically acceptable salts, their combinations with suitable medicament, pharmaceutical compositions containing them and their use as nicotinic acetylcholine receptor α7 subunit (α7 nAChR) modulator.

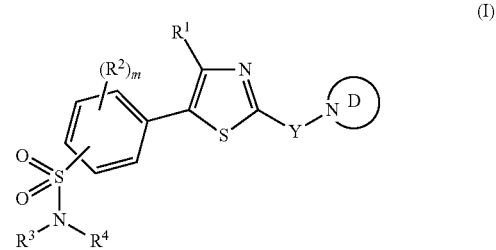

(I)

According to one aspect of the present invention there is provided compounds represented by the general formula I, its tautomeric forms, its stereoisomers, its pharmaceutically acceptable salts, their combinations with suitable medicament and pharmaceutical compositions containing them, wherein $R^1$ to $R^4$, ring D, Y. and m are described in details below.

Thus the present invention further provides a pharmaceutical composition, containing the compounds of the general formula (I) as defined herein, its tautomeric forms, its stereoisomers, and its pharmaceutically acceptable salts in combination with the usual pharmaceutically employed carriers, diluents, and the like are useful for the treatment and/or prophylaxis of diseases or disorder or condition such as Alzheimer's disease (AD), mild cognitive impairment (MCI), senile dementia, vascular dementia, dementia of Parkinson's disease, attention deficit disorder, attention deficit hyperactivity disorder (ADHD), dementia associated with Lewy bodies, AIDS dementia complex (ADC), Pick's disease, dementia associated with Down's syndrome, Huntington's disease, cognitive deficits associated with traumatic brain injury (TBI), cognitive decline associated with stroke, poststroke neuroprotection, cognitive and sensorimotor gating deficits associated with schizophrenia, cognitive deficits associated with bipolar disorder, cognitive impairments associated with depression, acute pain, post-surgical or post-operative pain, chronic pain, inflammation, inflammatory pain, neuropathic pain, smoking cessation, need for new blood vessel growth associated with wound healing, need for new blood vessel growth associated with vascularization of skin grafts and lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, and rheumatoid spondylitis.

The present invention also provides a pharmaceutical composition, containing the compounds of the general formula (I) as defined herein, its tautomeric forms, its stereoisomers, its pharmaceutically acceptable salts, its polymorphs, its solvates, and its optical isomers in combination with the usual pharmaceutically employed carriers, diluents, and the like are useful for the treatment and/or prophylaxis of diseases or disorder or condition classified or diagnosed as major or minor neurocognitive disorders, or disorders arising due to neurodegeneration.

The present invention also provides method of administering a compound of formula I, as defined herein in combination with or as adjunct to medications used in the treatment of attention deficit hyperactivity disorders, schizophrenia, and other cognitive disorders such as Alzheimer's disease, Parkinson's dementia, vascular dementia or dementia associated with Lewy bodies, traumatic brain injury.

The present invention also provides method of administering a compound of formula I, as defined herein in combination with or as an adjunct to acetylcholinesterase inhibitors, disease modifying drugs or biologics for neurodegenerative disorders, dopaminergic drugs, antidepressants, typical or an atypical antipsychotic.

The present invention also provides use of a compound of formula I as defended herein in the preparation of a medicament for treating a disease or disorder or condition selected from the group classified or diagnosed as major or minor neurocognitive disorders, or disorders arising due to neurodegeneration.

The present invention also provides use of a compound of formula I as defended herein in the preparation of a medicament for treating a disease or disorder or condition selected from attention deficit hyperactivity disorders, schizophrenia, cognitive disorders, Alzheimer's disease, Parkinson's dementia, vascular dementia or dementia associated with Lewy bodies, and traumatic brain injury.

The present invention also provides use of compound of formula I as defined herein in combination with or as an adjunct to acetylcholinesterase inhibitors, disease modifying drugs or biologics for neurodegenerative disorders, dopaminergic drugs, antidepressants, or a typical or atypical antipsychotic.

DETAILED DESCRIPTION OF THE INVENTION

The present invention relates to novel compound of the general formula I, its tautomeric forms, its stereoisomers, its pharmaceutically acceptable salts, their combinations with suitable medicament, and pharmaceutical compositions containing them

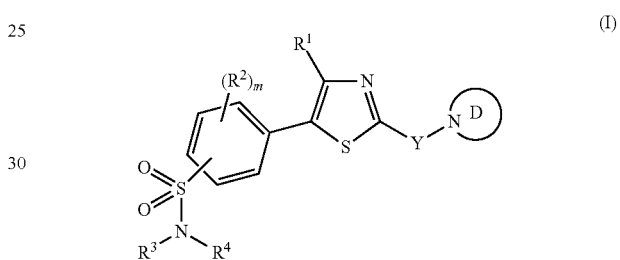

(I)

wherein, in the compound of formula I, ring D is substituted- or unsubstituted-5 to 12 membered heterocycle optionally containing 1 to 3 additional heteroatom(s)/group(s) selected from —S(O)$_n$—, —NR$^5$—, and —O—;

ring D may be substituted on ring carbons with 1 to 6 substituent(s) independently selected from halogen, nitro, cyano, oxo, substituted- or unsubstituted-alkyl, perhaloalkyl, substituted- or unsubstituted-cycloalkyl, substituted- or unsubstituted-aryl, substituted- or unsubstituted-heteroaryl, substituted- or unsubstituted-heterocyclyl, $R^{6b}$O—, $R^6$N(H)C(=O)—, $R^{6a}$C(=O)N(H)—, $R^6$N($R^7$)—, and $R^6$N(H)C(=O)N(H)—;

Y is bond, —CH$_2$—, or —C(=O)—;

$R^1$ is selected from substituted- or unsubstituted-aryl, substituted- or unsubstituted-heteroaryl, substituted- or unsubstituted-cycloalkyl, substituted- or unsubstituted-heterocyclyl;

$R^2$ is independently selected at each occurrence from halogen, nitro, cyano, substituted- or unsubstituted-alkyl, perhaloalkyl, substituted- or unsubstituted-cycloalkyl, substituted- or unsubstituted-heterocyclyl, $R^{6b}$O—, and $R^{6a}$C(=O)—, or two $R^2$ groups and the carbon atoms to which they are attached together form a 5- to 6-membered cyclic system which optionally contains 1 to 3 heteroatom(s) selected from —N—, —S—, and —O—, the said 5 to 6 membered ring system may be substituted with 1 to 3 substituent(s) independently selected from oxo, halogen, cyano, and alkyl;

$R^3$ and $R^4$ are independently selected from hydrogen, $R^{6a}$C(=O)—, substituted- or unsubstituted-alkyl, substituted- or unsubstituted-cycloalkyl, and substituted- or unsubstituted-heterocyclyl; or R³ and R⁴ together with the nitrogen atom to which they are attached form a 3- to 10-membered heterocyclic ring system containing one to three heteroatom(s) selected from —S—, —N—, and —O—, the said 3- to 10-membered heterocyclic ring system may be substituted with 1 to 3 substituent(s) independently selected from oxo, halogen, alkyl, OR⁶ᵇ, and R⁶N(H)—;

R⁵ is selected from hydrogen, substituted- or unsubstituted-alkyl, substituted- or unsubstituted-cycloalkyl, substituted- or unsubstituted-aryl, substituted- or unsubstituted-heterocyclyl, R⁶ᵃC(=O)—, and R⁶N(R⁷)C(=O)—;

R⁶ and R⁷ are each independently selected from hydrogen, substituted- or unsubstituted-alkyl, substituted- or unsubstituted-cycloalkyl, and substituted- or unsubstituted-heterocyclyl;

R⁶ᵃ is selected from substituted- or unsubstituted-alkyl, perhaloalkyl, substituted- or unsubstituted-cycloalkyl, and substituted- or unsubstituted-heterocyclyl;

R⁶ᵇ is selected from hydrogen, substituted- or unsubstituted-alkyl, perhaloalkyl, substituted- or unsubstituted-cycloalkyl, and substituted- or unsubstituted-heterocyclyl;

m is an integer selected from 0, 1, 2, and 3;

n is an integer selected from 0, 1, and 2;

when the alkyl group is a substituted alkyl group, the alkyl group is substituted with 1 to 4 substituents selected independently from oxo, halogen, nitro, cyano, perhaloalkyl, substituted- or unsubstituted-cycloalkyl, substituted- or unsubstituted-aryl, substituted- or unsubstituted-heteroaryl, substituted- or unsubstituted-heterocyclyl, R⁸ᵇO—, R⁸ᵃS(O₂)—, R⁸ᵃOC(=O)—, R⁸ᵃC(=O)O—, R⁸N(H)C(=O)—, R⁸N(alkyl)C(=O)—, R⁸ᵃC(=O)N(H)—, R⁸N(H)—, R⁸N(alkyl)-, R⁸N(H)C(=O)N(H)—, and R⁸N(alkyl)C(=O)N(H)—;

when the cycloalkyl and the carbocyclic groups are substituted, each of them is substituted with 1 to 3 substituents selected independently from oxo, halogen, nitro, cyano, substituted- or unsubstituted-alkyl, perhaloalkyl, substituted- or unsubstituted-aryl, substituted- or unsubstituted-heteroaryl, substituted- or unsubstituted-heterocyclyl, R⁸ᵇO—, R⁸ᶜS(O₂)—, R⁸ᶜC(=O)—, R⁸ᶜOC(=O)—, R⁸ᶜC(=O)O—, R⁸ᵈN(H)C(=O)—, R⁸ᵈN(alkyl)C(=O)—, R⁸ᶜC(=O)N(H)—, R⁸ᵈN(H)—, R⁸ᵈN(alkyl)-, R⁸ᵈN(H)C(=O)N(H)—, and R⁸ᵈN(alkyl)C(=O)N(H)—;

when the aryl group is substituted, it is substituted with 1 to 3 substituents selected independently from halogen, nitro, cyano, hydroxy, substituted- or unsubstituted-alkyl, perhaloalkyl, substituted- or unsubstituted-cycloalkyl, substituted- or unsubstituted-heterocycle, (alkyl)O—, (perhaloalkyl)O—, (alkyl)N(alkyl)-, (alkyl)N(H)—, H₂N—, (alkyl)S(O₂)—, (perhaloalkyl)S(O₂)—, (alkyl)C(=O)N(alkyl)-, (alkyl)C(=O)N(H)—, (alkyl)N(alkyl)C(=O)—, (alkyl)N(H)C(=O)—, H₂NC(=O)—, (alkyl)N(alkyl)S(O₂)—, (alkyl)N(H)S(O₂)—, and H₂NS(O₂)—;

when the heteroaryl group is substituted, it is substituted with 1 to 3 substituents selected independently from halogen, nitro, cyano, hydroxy, substituted- or unsubstituted-alkyl, perhaloalkyl, substituted- or unsubstituted-cycloalkyl, substituted- or unsubstituted-heterocycle, (alkyl)O—, (perhaloalkyl)O—, (alkyl)N(alkyl)-, (alkyl)N(H)—, H₂N—, (alkyl)S(O₂)—, (perhaloalkyl)S(O₂)—, (alkyl)C(=O)N(alkyl)-, (alkyl)C(=O)N(H)—, (alkyl)N(alkyl)C(=O)—, (alkyl)N(H)C(=O)—, H₂NC(=O)—, (alkyl)N(alkyl)S(O₂)—, (alkyl)N(H)S(O₂)—, and H₂NS(O₂)—;

when the heterocyclic group is substituted, it can be substituted either on a ring carbon atom or on a ring hetero atom, when it substituted on a ring carbon atom, it is substituted with 1-3 substituents selected independently from halogen, nitro, cyano, oxo, substituted- or unsubstituted-alkyl, perhaloalkyl, substituted- or unsubstituted-cycloalkyl, substituted- or unsubstituted-aryl, substituted- or unsubstituted-heteroaryl, substituted- or unsubstituted-heterocyclyl, R⁸ᵇO—, R⁸ᶜOC(=O)—, R⁸ᶜC(=O)O—, R⁸ᵈN(H)C(=O)—, R⁸ᵈN(alkyl)C(=O)—, R⁸ᶜC(=O)N(H)—, R⁸ᵈN(H)—, R⁸ᵈN(alkyl)-, R⁸ᵈN(H)C(=O)N(H)—, and R⁸ᵈN(alkyl)C(=O)N(H)—; when the 'heterocyclic' group is substituted on a ring nitrogen, it is substituted with a substituent selected from substituted- or unsubstituted-alkyl, substituted- or unsubstituted-cycloalkyl, substituted- or unsubstituted-aryl, substituted- or unsubstituted-heteroaryl, R⁸ᵃS(O₂)—, R⁸ᵃC(=O)—, R⁸ᵃ OC(=O)—R⁸N(H)C(=O)—, and R⁸N(alkyl)C(=O)—;

R⁸ is selected from hydrogen, alkyl, cycloalkyl, aryl, heteroaryl, and heterocyclyl;

R⁸ᵃ is selected from alkyl, perhaloalkyl, cycloalkyl, aryl, heteroaryl, and heterocyclyl;

R⁸ᵇ is selected from hydrogen, alkyl, perhaloalkyl, cycloalkyl, aryl, heteroaryl, and heterocyclyl;

R⁸ᶜ is selected from alkyl, perhaloalkyl, and cycloalkyl;

R⁸ᵈ is selected from hydrogen, alkyl, and cycloalkyl.

Ring D is particularly selected as substituted- or unsubstituted-5 to 12 membered heterocycle optionally containing 1 to 3 additional heteroatom(s) selected from —NR⁵— and —O—.

Ring D is more particularly selected from

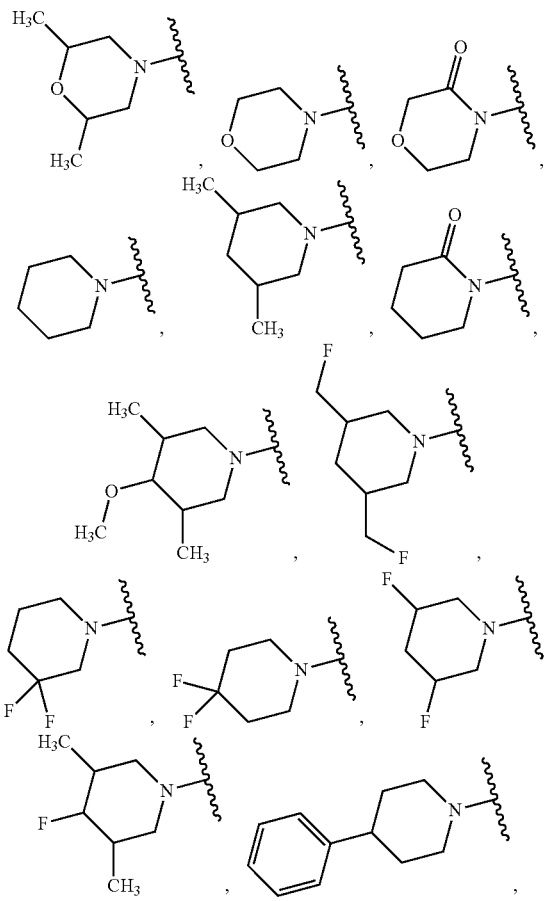

-continued

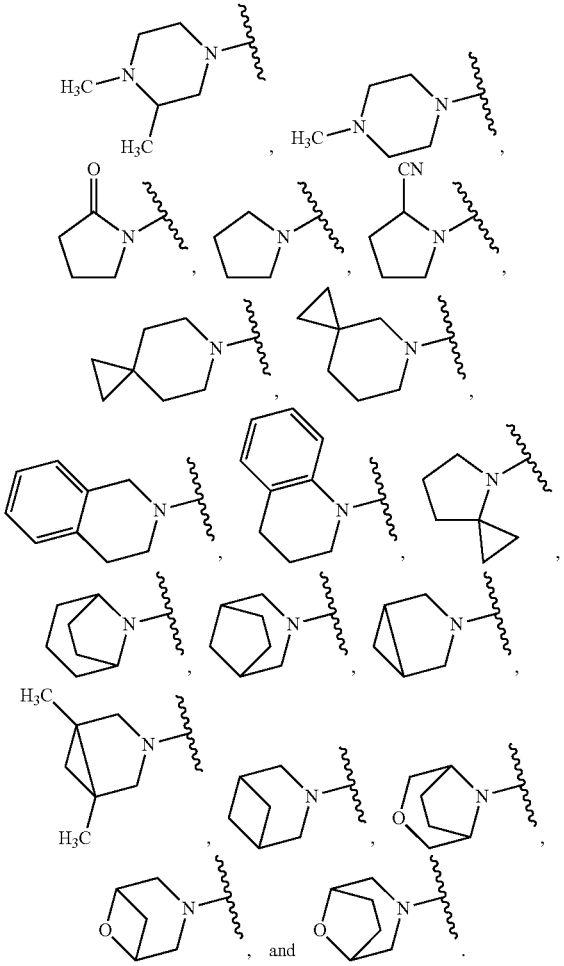

, and $R^1$ is particularly selected from a)

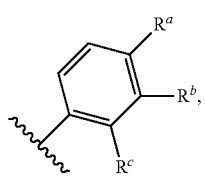

wherein $R^a$ is selected from halogen, cyano, cyclopropyl, methyl, trifluoromethyl, dimethyl amine, $H_3CS(O_2)$—, $H_2NC(=O)$—, $H_3CC(=O)N(H)$—, and $(CH_3)_2NC(=O)$—; $R^b$ is selected from hydrogen, halogen, cyclopropyl, and methyl; $R^c$ is selected from hydrogen and halogen;

b)

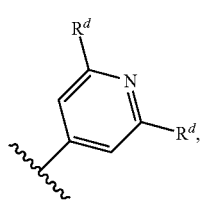

wherein $R^d$ is independently selected at each occurrence from hydrogen and methyl;

c)

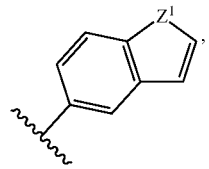

wherein, $Z^1$ is selected from —$CH_2$—, —N(H)—, —N($CH_3$)—, and —N($COCH_3$)—; "- - - -" is either a single bond or a double bond; and d) cyclopropyl,

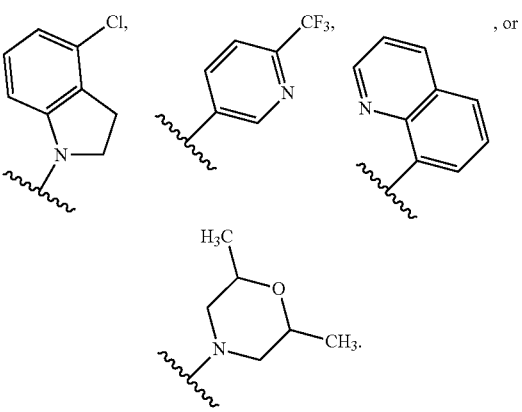

$R^2$ is particularly selected from substituted- or unsubstituted-alkyl, halogen, and perhaloalkyl; or two $R^2$ groups and the carbon atoms to which they are attached together form a substituted- or unsubstituted-5 to 6 membered carbocycle.

$R^2$ is more particularly selected from methyl, fluoro, and trifluoromethyl; or two $R^2$ groups and two adjacent carbon atoms to which they are attached together forming a six membered carbocycle.

m is particularly selected from 0, 1, and 2.

$R^3$ and $R^4$ are particularly selected from hydrogen, substituted- or unsubstituted-alkyl, and $R^{6a}C(=O)$—; or $R^3$, $R^4$ and the nitrogen to which they are attached together forming a 3- to 10-membered heterocycle.

$R^3$ and $R^4$ are more particularly selected from hydrogen, methyl, and acetyl; or $R^3$, $R^4$ and the nitrogen to which they are attached together forming piperidine.

Whenever a range of the number of atoms in a structure is indicated (e.g., a $C_{1-2}$, $C_{1-8}$, $C_{1-5}$, or $C_{1-4}$ alkyl, alkylamino, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

One of the embodiments of the present invention is compound of formula (Ia)

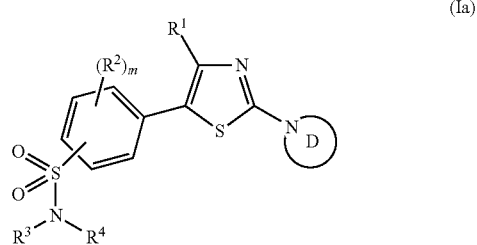

(Ia)

wherein, $R^1$, $R^2$, $R^3$, $R^4$, m, and ring D is same as defined above.

Other embodiment of the present invention is compound of formula (Ib)

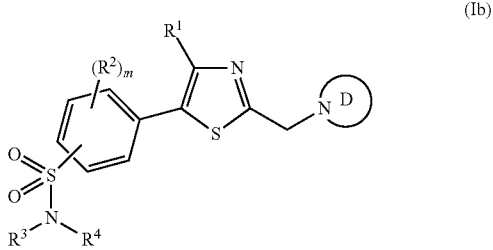

(Ib)

wherein, $R^1$, $R^2$, $R^3$, $R^4$, m, and ring D is same as defined above.

Another embodiment of the present invention is compound of formula (Ic)

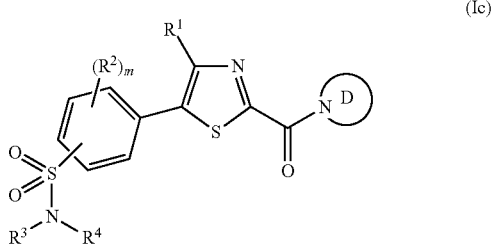

(Ic)

wherein, $R^1$, $R^2$, $R^3$, $R^4$, m, and ring D is same as defined above.

General terms used in formula can be defined as follows; however, the meaning stated should not be interpreted as limiting the scope of the term per se.

The term "alkyl", as used herein, means a straight chain or branched hydrocarbon containing from 1 to 20 carbon atoms. Preferably the alkyl chain may contain 1 to 10 carbon atoms. More preferably alkyl chain may contain up to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

'Alkyl', as defined hereinabove may be substituted with 1 to 4 substituents selected independently from oxo, halogen, nitro, cyano, perhaloalkyl, substituted- or unsubstituted-cycloalkyl, substituted- or unsubstituted-aryl, substituted- or unsubstituted-heteroaryl, substituted- or unsubstituted-heterocyclyl, $R^{8b}O-$, $R^{8a}S(O_2)-$, $R^{8a}OC(=O)-$, $R^{8a}C(=O)O-$, $R^8N(H)C(=O)-$, $R^8N(alkyl)C(=O)-$, $R^{8a}C(=O)N(H)-$, $R^8N(H)-$, $R^8N(alkyl)-$, $R^8N(H)C(=O)N(H)-$, and $R^8N(alkyl)C(=O)N(H)-$; wherein $R^8$ is selected from hydrogen, alkyl, cycloalkyl, aryl, heteroaryl, and heterocyclyl; $R^{8a}$ is selected from alkyl, perhaloalkyl, cycloalkyl, aryl, heteroaryl, and heterocyclyl; $R^{8b}$ is selected from hydrogen, alkyl, perhaloalkyl, cycloalkyl, aryl, heteroaryl, and heterocyclyl.

The term "perhaloalkyl" used herein means an alkyl group as defined hereinabove wherein all the hydrogen atoms of the said alkyl group are substituted with halogen. The perhaloalkyl group is exemplified by trifluoromethyl, pentafluoroethyl, and the like.

The term "cycloalkyl" as used herein, means a monocyclic, bicyclic, or tricyclic non-aromatic ring system containing from 3 to 14 carbon atoms, preferably monocyclic cycloalkyl ring containing 3 to 6 carbon atoms. Examples of monocyclic ring systems include cyclopropyl, cyclobutyl, cyclopentyl, cyclohexyl, cycloheptyl, and cyclooctyl-Bicyclic ring systems include monocyclic ring system fused across a bond with another cyclic system which may be an alicyclic ring or an aromatic ring. Bicyclic rings also include spirocyclic systems wherein the second ring gets annulated on a single carbon atom. Bicyclic ring systems are also exemplified by a bridged monocyclic ring system in which two non-adjacent carbon atoms of the monocyclic ring are linked by an alkylene bridge. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, bicyclo[3.3.2]decane, bicyclo[3.1.0]hexane, bicyclo[410]heptane, bicyclo[3.2.0]heptanes, octahydro-1H-indene, spiro[2.5]octane, spiro[4.5]decane, spiro[bicyclo[4.1.0]heptane-2,1'-cyclopentane], hexahydro-2'H-spiro[cyclopropane-1,1'-pentalene]. Tricyclic ring systems are the systems wherein the bicyclic systems as described about are further annulated with third ring, which may be alicyclic ring or aromatic ring. Tricyclic ring systems are also exemplified by a bicyclic ring system in which two non-adjacent carbon atoms of the bicyclic ring are linked by a bond or an alkylene bridge. Representative examples of tricyclic-ring systems include, but are not limited to, tricyclo[3.3.1.0$^{3.7}$]nonane, and tricyclo[3.3.1.1$^{3.7}$]decane (adamantane).

The term "carbocycle" as used herein, means a cyclic system made up of carbon atoms, which includes cycloalkyl, and aryl.

'Cycloalkyl', as defined hereinabove may be substituted with 1 to 3 substituents selected independently from oxo, halogen, nitro, cyano, substituted- or unsubstituted-alkyl, perhaloalkyl, substituted- or unsubstituted-aryl, substituted- or unsubstituted-heteroaryl, substituted- or unsubstituted-heterocyclyl, $R^{8b}O-$, $R^{8c}S(O_2)-$, $R^{8c}C(=O)-$, $R^{8c}OC(=O)-$, $R^{8c}C(=O)O-$, $R^{8d}N(H)C(=O)-$, $R^{8d}N(alkyl)C(=O)-$, $R^{8c}C(=O)N(H)-$, $R^{8d}N(H)-$, $R^{8d}N(alkyl)-$, $R^{8d}N(H)C(=O)N(H)-$, and $R^{8d}N(alkyl)C(=O)N(H)-$; $R^{8b}$ is selected from hydrogen, alkyl, perhaloalkyl, cycloalkyl, aryl, heteroaryl, and heterocyclyl; $R^{8c}$ is selected from alkyl, perhaloalkyl, and cycloalkyl; $R^{8d}$ is selected from hydrogen, alkyl and cycloalkyl.

The term "aryl" refers to a monovalent monocyclic, bicyclic or tricyclic aromatic hydrocarbon ring system. Examples of aryl groups include phenyl, naphthyl, anthracenyl, fluorenyl, indenyl, azulenyl, and the like. Aryl group also include partially saturated bicyclic and tricyclic aromatic hydrocarbons such as tetrahydro-naphthalene. The said aryl group also includes aryl rings fused with heteroaryl or heterocyclic rings such as 2,3-dihydro-benzo[1,4]dioxin-6-yl, 2,3-dihydro-benzo[1,4]dioxin-5-yl, 2,3-dihydro-benzofuran-5-yl, 2,3-dihydro-benzofuran-4-yl, 2,3-dihydro-benzofuran-6-yl, 2,3-dihydro-benzofuran-6-yl, 2,3-dihydro-1H-indol-5-yl, 2,3-dihydro-1H-indol-4-yl 2,3-dihydro-1H-indol-6-yl, 2,3-dihydro-1H-indol-7-yl, benzo[1,3]dioxol-4-yl, benzo[1,3]dioxol-5-yl, 1,2,3,4-tetrahydroquinolinyl, 1,2,3,4-tetrahydroisoquinolnyl, 2,3-dihydrobenzothien-4-yl, 2-oxoindolin-5-yl.

'Aryl', as defined hereinabove may be substituted with 1 to 3 substituents selected independently from halogen, nitro, cyano, hydroxy, substituted- or unsubstituted-alkyl, perhaloalkyl, substituted- or unsubstituted-cycloalkyl, substituted- or unsubstituted-heterocycle, (alkyl)O—, (perhaloalkyl)O—, (alkyl)N(alkyl)-, (alkyl)N(H)—, $H_2N$—, (alkyl)S($O_2$)—, (perhaloalkyl)S($O_2$)—, (alkyl)C(=O)N(alkyl)-, (alkyl)C(=O)N(H)—, (alkyl)N(alkyl)C(=O)—, (alkyl)N(H)C(=O)—, $H_2NC$(=O)—, (alkyl)N(alkyl)S($O_2$)—, (alkyl)N(H)S($O_2$)—, and $H_2NS(O_2)$—.

The term "heteroaryl" refers to a 5-14 membered monocyclic, bicyclic, or tricyclic ring system having 1-4 ring heteroatoms selected from O, N, or S, and the remainder ring atoms being carbon (with appropriate hydrogen atoms unless otherwise indicated), wherein at least one ring in the ring system is aromatic.

Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, benzoxazolyl, benzofuranyl, indolizinyl, imidazopyridyl, tetrazolyl, benzimidazolyl, benzothiazolyl, benzothiadiazolyl, benzoxadiazolyl, indolyl, azaindolyl, imidazopyridyl, quinazolinyl, purinyl, pyrrolo[2,3]pyrimidinyl, pyrazolo[3,4]pyrimidinyl, and benzo(b)thienyl, 2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, and the like.

'Heteroaryl', as defined hereinabove may be substituted with 1 to 3 substituents selected independently from halogen, nitro, cyano, hydroxy, substituted- or unsubstituted-alkyl, perhaloalkyl, substituted- or unsubstituted-cycloalkyl, substituted- or unsubstituted-heterocycle, (alkyl)O—, (perhaloalkyl)O—, (alkyl)N(alkyl)-, (alkyl)N(H)—, $H_2N$—, (alkyl)S($O_2$)— (perhaloalkyl)S($O_2$)—, (alkyl)C(=O)N(alkyl)-, (alkyl)C(=O)N(H)—, (alkyl)N(alkyl)C(=O)—, (alkyl)N(H)C(=O)—, $H_2NC$(=O)—, (alkyl)N(alkyl)S($O_2$)—, (alkyl)N(H)S($O_2$)—, and $H_2NS(O_2)$—.

The term "heterocycle" or "heterocyclic" as used herein, means a 'cycloalkyl' group wherein one or more of the carbon atoms replaced by —O—, —S—, —S($O_2$)—, —S(O)—, —N($R'''$)—, —Si($R'''$)$R''$—, wherein, $R'''$ and $R''$ are independently selected from hydrogen, alkyl, aryl, heteroaryl, cycloalkyl, and heterocyclyl. The heterocycle may be connected to the parent molecular moiety through any carbon atom or any nitrogen atom contained within the heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. Representative examples of bicyclic heterocycle include, but are not limited to 1,2,3,4-tetrahydroisoquinolin-2-yl, 1,2,3,4-tetrahydroquinolin-1-yl, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. The term heterocycle also include bridged and spiro heterocyclic systems such as azabicyclo[3.2.1]octane, azabicyclo[3.3.1]nonane, 8-oxa-3-azabicyclo[3.2.1]octan-3-yl, 3-oxa-8-azabicyclo[3.2.1]octan-8-yl, 6-oxa-3-azabicyclo[3.1.1]heptan-3-yl, 8-azabicyclo[3.2.1]octan-8-yl, 3-azabicyclo[3.2.1]octan-3-yl, 3-azabicyclo[3.1.0]hexan-3-yl, 6-azaspiro[2.5]octan-6-yl, 5-azaspiro[2.5]octan-5-yl, 4-azaspiro[2.4]heptan-4-yl, and the like.

'Heterocyclyl', as defined hereinabove may be substituted on ring carbons with 1 to 3 substituents selected independently from halogen, nitro, cyano, oxo, substituted- or unsubstituted-alkyl, perhaloalkyl, substituted- or unsubstituted-cycloalkyl, substituted- or unsubstituted-aryl, substituted- or unsubstituted-heteroaryl, substituted- or unsubstituted-heterocyclyl, $R^{8b}$O—, $R^{8c}$OC(=O)—, $R^{8c}$C(=O)O—, $R^{8d}$N(H)C(=O)—, $R^{8d}$N(alkyl)C(=O)—, $R^{8c}$C(=O)N(H)—, $R^{8d}$N(H)—, $R^{8d}$N(alkyl)-, $R^{8d}$N(H)C(=O)N(H)—, and $R^{8d}$N(alkyl)C(=O)N(H)—; wherein $R^{8b}$ is selected from hydrogen, alkyl, perhaloalkyl, cycloalkyl, aryl, heteroaryl, and heterocyclyl; $R^{8c}$ is selected from alkyl, perhaloalkyl, and cycloalkyl; $R^{8d}$ is selected from hydrogen, alkyl, and cycloalkyl.

'Heterocyclyl', as defined hereinabove may further be substituted on ring nitrogen(s) with substituents selected from substituted- or unsubstituted-alkyl, substituted- or unsubstituted-cycloalkyl, substituted- or unsubstituted-aryl, substituted- or unsubstituted-heteroaryl, $R^{8a}$S($O_2$)—, $R^{8a}$C(=O)—, $R^{8a}$ OC(=O)—, $R^8$N(H)C(=O)—, and $R^8$N(alkyl)C(=O)—; wherein $R^8$ is selected from hydrogen, alkyl, cycloalkyl, aryl, heteroaryl, and heterocyclyl; $R^{8a}$ is selected from alkyl, perhaloalkyl, cycloalkyl, aryl, heteroaryl, and heterocyclyl;

The term 'oxo' means a divalent oxygen (=O) attached to the parent group. For example oxo attached to carbon forms a carbonyl, oxo substituted on cyclohexane forms a cyclohexanone, and the like.

The term 'annulated' means the ring system under consideration is either annulated with another ring at a carbon atom of the cyclic system or across a bond of the cyclic system as in the case of fused or spiro ring systems.

The term 'bridged' means the ring system under consideration contain an alkylene bridge having 1 to 4 methylene units joining two non adjacent ring atoms.

A compound, its stereoisomers, racemates, and pharmaceutically acceptable salt thereof as described hereinabove wherein the compound of general formula I is selected from:
1. (cis) 4-(4-(4-chlorophenyl)-2-(2,6-dimethylmorpholino)thiazol-5-yl)benzenesulfonamide;
2. 4-(4-(4-chlorophenyl)-2-morpholinothiazol-5-yl)benzenesulfonamide;
3. 4-(4-(4-chlorophenyl)-2-(4-methylpiperazin-1-yl)thiazol-5-yl)benzenesulfonamide;
4. 4-(4-(4-chlorophenyl)-2-(piperidin-1-yl)thiazol-5-yl)benzenesulfonamide;
5. (cis) 4-(4-(4-chlorophenyl)-2-(3,5-dimethylpiperidin-1-yl)thiazol-5-yl)benzenesulfonamide;

6. (cis) 4-(4-cyclopropyl-2-(2,6-dimethylmorpholino)thiazol-5-yl)benzenesulfonamide;
7. (trans+) 4-(4-(4-chlorophenyl)-2-(3,5-dimethylpiperidin-1-yl)thiazol-5-yl)benzenesulfonamide
8. (trans−) 4-(4-(4-chlorophenyl)-2-(3,5-dimethylpiperidin-1-yl)thiazol-5-yl)benzenesulfonamide;
9. (R)-4-(4-(4-chlorophenyl)-2-(3,4-dimethylpiperazin-1-yl)thiazol-5-yl)benzenesulfonamide;
10. 4-(4-(4-chlorophenyl)-2-(2-oxopiperidin-1-yl)thiazol-5-yl)benzenesulfonamide;
11. 4-(4-(4-chlorophenyl)-2-(2-oxopyrrolidin-1-yl)thiazol-5-yl)benzenesulfonamide;
12. 4-(4-(4-chlorophenyl)-2-(3-oxomorpholino)thiazol-5-yl)benzenesulfonamide;
13. (cis) 4-(4-(4-chlorophenyl)-2-(2,6-dimethylmorpholine-4-carbonyl)thiazol-5-yl)benzenesulfonamide;
14. 4-(4-(4-chlorophenyl)-2-(morpholine-4-carbonyl)thiazol-5-yl)benzenesulfonamide;
15. (+) 4-(4-(4-chlorophenyl)-2-(4-methoxy-cis-3,5-dimethylpiperidine-1-carbonyl)thiazol-5-yl)benzenesulfonamide;
16. (−) 4-(4-(4-chlorophenyl)-2-(4-methoxy-cis-3,5-dimethylpiperidine-1-carbonyl)thiazol-5-yl)benzenesulfonamide;
17. (trans ±) 4-(2-(2,6-bis(fluoromethyl)morpholine-4-carbonyl)-4-(4-chlorophenyl)thiazol-5-yl)benzenesulfonamide;
18. 4-(4-(4-chlorophenyl)-2-(piperidine-1-carbonyl)thiazol-5-yl)benzenesulfonamide;
19. (trans ±) 4-(4-(4-chlorophenyl)-2-(3,5-dimethylpiperidine-1-carbonyl)thiazol-5-yl)benzenesulfonamide;
20. (cis) 4-(4-(4-chlorophenyl)-2-(3,5-dimethylpiperidine-1-carbonyl)thiazol-5-yl)benzenesulfonamide;
21. 4-(4-(4-chlorophenyl)-2-(3,3-difluoropiperidine-1-carbonyl)thiazol-5-yl)benzenesulfonamide;
22. 4-(4-(4-chlorophenyl)-2-(4,4-difluoropiperidine-1-carbonyl)thiazol-5-yl)benzenesulfonamide;
23. (cis) 4-(4-(4-chlorophenyl)-2-(3,5-difluoropiperidine-1-carbonyl)thiazol-5-yl)benzenesulfonamide;
24. 4-(4-(4-chlorophenyl)-2-(4-fluoro-cis-3,5-dimethylpiperidine-1-carbonyl)thiazol-5-yl)benzenesulfonamide;
25. 4-(4-(4-chlorophenyl)-2-(pyrrolidine-1-carbonyl)thiazol-5-yl)benzenesulfonamide;
26. (S)-4-(4-(4-chlorophenyl)-2-(2-cyanopyrrolidine-1-carbonyl)thiazol-5-yl)benzenesulfonamide;
27. (R)-4-(4-(4-chlorophenyl)-2-(3,4-dimethylpiperazine-1-carbonyl)thiazol-5-yl)benzenesulfonamide;
28. (cis) 4-(2-(2,6-dimethylmorpholine-4-carbonyl)-4-(4-(trifluoromethyl)phenyl)thiazol-5-yl)benzenesulfonamide;
29. (cis) 4-(2-(2,6-dimethylmorpholine-4-carbonyl)-4-(p-tolyl)thiazol-5-yl)benzenesulfonamide;
30. (cis) 4-(2-(2,6-dimethylmorpholine-4-carbonyl)-4-(4-fluorophenyl)thiazol-5-yl)benzenesulfonamide;
31. (cis) 4-(4-(4-(dimethylamino)phenyl)-2-(2,6-dimethylmorpholine-4-carbonyl)thiazol-5-yl)benzenesulfonamide;
32. (cis) 4-(2-(2,6-dimethylmorpholine-4-carbonyl)-4-(4-(methylsulfonyl)phenyl)thiazol-5-yl)benzenesulfonamide;
33. (cis) 4-(4-(4-cyclopropylphenyl)-2-(2,6-dimethylmorpholine-4-carbonyl)thiazol-5-yl)benzenesulfonamide;
34. (cis) 4-(4-(4-cyanophenyl)-2-(2,6-dimethylmorpholine-4-carbonyl)thiazol-5-yl)benzenesulfonamide;
35. (cis) 4-(2-(2,6-dimethylmorpholine-4-carbonyl)-4-(2,6-dimethylpyridin-4-yl)thiazol-5-yl)benzenesulfonamide;
36. (cis) 4-(2-(2,6-dimethylmorpholine-4-carbonyl)-4-(pyridin-4-yl)thiazol-5-yl)benzenesulfonamide;
37. (cis) 4-(4-(2,4-difluorophenyl)-2-(2,6-dimethylmorpholine-4-carbonyl)thiazol-5-yl)benzenesulfonamide;
38. (cis) 4-(4-(3,4-difluorophenyl)-2-(2,6-dimethylmorpholine-4-carbonyl)thiazol-5-yl)benzenesulfonamide;
39. (cis) 4-(4-(4-chloro-3-cyclopropylphenyl)-2-(2,6-dimethylmorpholine-4-carbonyl)thiazol-5-yl)benzenesulfonamide;
40. 4-(4-(4-chloro-3-methylphenyl)-2-(pyrrolidine-1-carbonyl)thiazol-5-yl)benzenesulfonamide;
41. (cis) 4-(2-(2,6-dimethylmorpholine-4-carbonyl)-4-(1H-indol-5-yl)thiazol-5-yl)benzenesulfonamide;
42. (cis) 4-(2-(2,6-dimethylmorpholine-4-carbonyl)-4-(1-methyl-1H-indol-5-yl)thiazol-5-yl)benzenesulfonamide;
43. (cis) 4-(4-(2,3-dihydro-1H-inden-5-yl)-2-(2,6-dimethylmorpholine-4-carbonyl)thiazol-5-yl)benzenesulfonamide;
44. (cis) 4-(4-(1-acetylindolin-5-yl)-2-(2,6-dimethylmorpholine-4-carbonyl)thiazol-5-yl)benzenesulfonamide;
45. (cis) 4-(4-(4-chloroindolin-1-yl)-2-(2,6-dimethylmorpholine-4-carbonyl)thiazol-5-yl)benzenesulfonamide;
46. (cis) 4-(4-(4-chlorophenyl)-2-(2,6-dimethylmorpholine-4-carbonyl)thiazol-5-yl)-2-methylbenzenesulfonamide;
47. (cis) 4-(4-(4-chlorophenyl)-2-(2,6-dimethylmorpholine-4-carbonyl)thiazol-5-yl)-3-fluorobenzenesulfonamide;
48. (cis) 4-(4-(4-chlorophenyl)-2-(2,6-dimethylmorpholine-4-carbonyl)thiazol-5-yl)-2-fluorobenzenesulfonamide;
49. (cis) 4-(4-(4-chlorophenyl)-2-(2,6-dimethylmorpholine-4-carbonyl)thiazol-5-yl)-2-(trifluoromethyl)benzenesulfonamide;
50. 4-(4-(4-chlorophenyl)-2-(piperidine-1-carbonyl)thiazol-5-yl)-3-fluorobenzenesulfonamide;
51. 4-(4-(4-chlorophenyl)-2-(4,4-difluoropiperidine-1-carbonyl)thiazol-5-yl)-2-methylbenzenesulfonamide;
52. 4-(4-(4-chlorophenyl)-2-(pyrrolidine-1-carbonyl)thiazol-5-yl)-3-fluorobenzenesulfonamide;
53. 4-(4-(4-chlorophenyl)-2-(pyrrolidine-1-carbonyl)thiazol-5-yl)-2-fluorobenzenesulfonamide;
54. (cis) 4-(4-(4-chloro-3-cyclopropylphenyl)-2-(2,6-dimethylmorpholine-4-carbonyl)thiazol-5-yl)-2-methylbenzenesulfonamide;
55. 4-(2-(8-oxa-3-azabicyclo[3.2.1]octan-3-yl)-4-(4-chlorophenyl)thiazol-5-yl)benzenesulfonamide;
56. 4-(2-(3-oxa-8-azabicyclo[3.2.1]octan-8-yl)-4-(4-chlorophenyl)thiazol-5-yl)benzenesulfonamide;
57. 4-(2-(6-oxa-3-azabicyclo[3.1.1]heptan-3-yl)-4-(4-chlorophenyl)thiazol-5-yl)benzenesulfonamide;
58. 4-(2-(8-azabicyclo[3.2.1]octan-8-yl)-4-(4-chlorophenyl)thiazol-5-yl)benzenesulfonamide;
59. 4-(2-(3-azabicyclo[3.2.1]octan-3-yl)-4-(4-chlorophenyl)thiazol-5-yl)benzenesulfonamide;
60. 4-(2-(3-azabicyclo[3.1.0]hexan-3-yl)-4-(4-chlorophenyl)thiazol-5-yl)benzenesulfonamide;
61. (cis) 4-(4-(4-chlorophenyl)-2-(1,5-dimethyl-3-azabicyclo[3.1.0]hexan-3-yl)thiazol-5-yl)benzenesulfonamide;
62. 4-(4-(4-chlorophenyl)-2-(6-azaspiro[2.5]octan-6-yl)thiazol-5-yl)benzenesulfonamide;
63. 4-(4-(4-chlorophenyl)-2-(5-azaspiro[2.5]octan-5-yl)thiazol-5-yl)benzenesulfonamide;
64. 4-(4-(4-chlorophenyl)-2-(3,4-dihydroisoquinolin-2(1H)-yl)thiazol-5-yl)benzenesulfonamide;
65. 4-(4-(4-chlorophenyl)-2-(3,4-dihydroquinolin-1(2H)-yl)thiazol-5-yl)benzenesulfonamide;
66. 4-(2-(3-azabicyclo[3.1.0]hexan-3-yl)-4-(2,4-difluorophenyl)thiazol-5-yl)benzenesulfonamide;

67. 4-(2-(8-oxa-3-azabicyclo[3.2.1]octane-3-carbonyl)-4-(4-chlorophenyl)thiazol-5-yl)benzenesulfonamide;
68. 4-(2-(3-oxa-8-azabicyclo[3.2.1]octane-8-carbonyl)-4-(4-chlorophenyl)thiazol-5-yl)benzenesulfonamide;
69. 4-(2-(6-oxa-3-azabicyclo[3.1.1]heptane-3-carbonyl)-4-(4-chlorophenyl)thiazol-5-yl)benzenesulfonamide;
70. 4-(2-(8-azabicyclo[3.2.1]octane-8-carbonyl)-4-(4-chlorophenyl)thiazol-5-yl)benzenesulfonamide;
71. 4-(2-(3-azabicyclo[3.2.1]octane-3-carbonyl)-4-(4-chlorophenyl)thiazol-5-yl)benzenesulfonamide;
72. (cis) 4-(4-(4-chlorophenyl)-2-(1,5-dimethyl-3-azabicyclo[3.1.0]hexane-3-carbonyl)thiazol-5-yl)benzenesulfonamide;
73. 4-(2-(3-azabicyclo[3.1.0]hexane-3-carbonyl)-4-(4-chlorophenyl)thiazol-5-yl)benzenesulfonamide;
74. 4-(4-(4-chlorophenyl)-2-(1,2,3,4-tetrahydroquinoline-1-carbonyl)thiazol-5-yl)benzenesulfonamide;
75. 4-(4-(4-chlorophenyl)-2-(1,2,3,4-tetrahydroisoquinoline-2-carbonyl)thiazol-5-yl)benzenesulfonamide;
76. 4-(4-(4-chlorophenyl)-2-(6-azaspiro[2.5]octane-6-carbonyl)thiazol-5-yl)benzenesulfonamide;
77. 4-(4-(4-chlorophenyl)-2-(5-azaspiro[2.5]octane-5-carbonyl)thiazol-5-yl)benzenesulfonamide;
78. 4-(2-(3-azabicyclo[3.1.1]heptane-3-carbonyl)-4-(4-chlorophenyl)thiazol-5-yl)benzenesulfonamide;
79. 4-(4-(4-chlorophenyl)-2-(4-azaspiro[2.4]heptane-4-carbonyl)thiazol-5-yl)benzenesulfonamide;
80. 4-(2-(3-azabicyclo[3.1.0]hexane-3-carbonyl)-4-(4-chloro-3-methylphenyl)thiazol-5-yl)benzenesulfonamide;
81. 4-(2-(3-azabicyclo[3.1.0]hexane-3-carbonyl)-5-(4-sulfamoylphenyl)thiazol-4-yl)benzamide;
82. N-(4-(2-(3-azabicyclo[3.1.0]hexane-3-carbonyl)-5-(4-sulfamoylphenyl)thiazol-4-yl)phenyl)acetamide;
83. 4-(2-(3-azabicyclo[3.1.0]hexane-3-carbonyl)-5-(4-sulfamoylphenyl)thiazol-4-yl)-N,N-dimethylbenzamide;
84. 4-(2-(3-azabicyclo[3.1.0]hexane-3-carbonyl)-4-(2,4-difluorophenyl)thiazol-5-yl)benzenesulfonamide;
85. 4-(2-(3-azabicyclo[3.1.0]hexane-3-carbonyl)-4-(4-(trifluoromethyl)phenyl)thiazol-5-yl)benzenesulfonamide;
86. 4-(2-(3-azabicyclo[3.1.0]hexane-3-carbonyl)-4-(4-cyclopropylphenyl)thiazol-5-yl)benzenesulfonamide;
87. 4-(2-(3-azabicyclo[3.1.0]hexane-3-carbonyl)-4-(6-(trifluoromethyl)pyridin-3-yl)thiazol-5-yl)benzenesulfonamide;
88. 4-(2-(3-azabicyclo[3.1.0]hexane-3-carbonyl)-4-(quinolin-8-yl)thiazol-5-yl)benzenesulfonamide;
89. 4-(2-(3-azabicyclo[3.1.0]hexane-3-carbonyl)-4-(4-chloroindolin-1-yl)thiazol-5-yl)benzenesulfonamide;
90. (cis) 4-(2-(3-azabicyclo[3.1.0]hexane-3-carbonyl)-4-(2,6-dimethylmorpholino)thiazol-5-yl)benzenesulfonamide;
91. 4-(4-(1-acetylindolin-5-yl)-2-(3-azabicyclo[3.1.0]hexane-3-carbonyl)thiazol-5-yl)benzenesulfonamide;
92. 4-(2-(3-azabicyclo[3.1.0]hexane-3-carbonyl)-4-(4-chlorophenyl)thiazol-5-yl)-N,N-dimethylbenzenesulfonamide;
93. 3-azabicyclo[3.1.0]hexan-3-yl(4-(4-chlorophenyl)-5-(4-(piperidin-1-ylsulfonyl)phenyl)thiazol-2-yl)methanone;
94. 4-(2-(3-azabicyclo[3.1.0]hexane-3-carbonyl)-4-(4-chlorophenyl)thiazol-5-yl)-2-methylbenzenesulfonamide;
95. N-((4-(2-(3-azabicyclo[3.1.0]hexane-3-carbonyl)-4-(4-chlorophenyl)thiazol-5-yl)phenyl)sulfonyl)acetamide;
96. 4-(2-(3-azabicyclo[3.1.0]hexane-3-carbonyl)-4-(4-chlorophenyl)thiazol-5-yl)-2-(trifluoromethyl)benzenesulfonamide;
97. 4-(2-(3-azabicyclo[3.1.0]hexane-3-carbonyl)-4-(4-chlorophenyl)thiazol-5-yl)-3-methylbenzenesulfonamide;
98. 4-(2-(3-azabicyclo[3.1.0]hexane-3-carbonyl)-4-(4-chlorophenyl)thiazol-5-yl)-3-fluorobenzenesulfonamide;
99. 4-(2-(3-azabicyclo[3.1.0]hexane-3-carbonyl)-4-(4-chlorophenyl)thiazol-5-yl)-2-fluorobenzenesulfonamide;
100. 4-(2-(3-azabicyclo[3.1.0]hexane-3-carbonyl)-4-(4-chlorophenyl)thiazol-5-yl)-5,6,7,8-tetrahydronaphthalene-1-sulfonamide;
101. 4-(2-(3-azabicyclo[3.1.0]hexane-3-carbonyl)-4-(4-chloro-3-methylphenyl)thiazol-5-yl)-2-fluorobenzenesulfonamide;
102. 4-(2-(3-azabicyclo[3.1.0]hexan-3-ylmethyl)-4-(4-chlorophenyl)thiazol-5-yl)benzenesulfonamide;
103. 4-(4-(4-chlorophenyl)-2-((2-oxopyrrolidin-1-yl)methyl)thiazol-5-yl)benzenesulfonamide;
104. 4-(4-(4-chlorophenyl)-2-((2-oxopyrrolidin-1-yl)methyl)thiazol-5-yl)-3-fluorobenzenesulfonamide;
105. 4-(4-(4-chlorophenyl)-2-((2-oxopiperidin-1-yl)methyl)thiazol-5-yl)benzenesulfonamide; and
106. 4-(4-(4-chlorophenyl)-2-(4-phenylpiperidin-1-yl)thiazol-5-yl)benzenesulfonamide.

According to another aspect of the present invention, the compounds of general formula I where all the symbols are as defined earlier were prepared by methods described below. However, the invention is not limited to these methods; the compounds may also be prepared by using procedures described for structurally related compounds in the literature.

Scheme-1

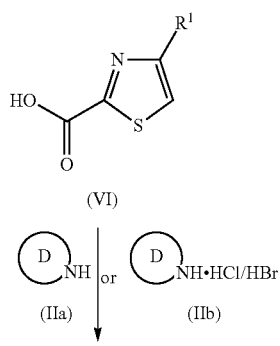

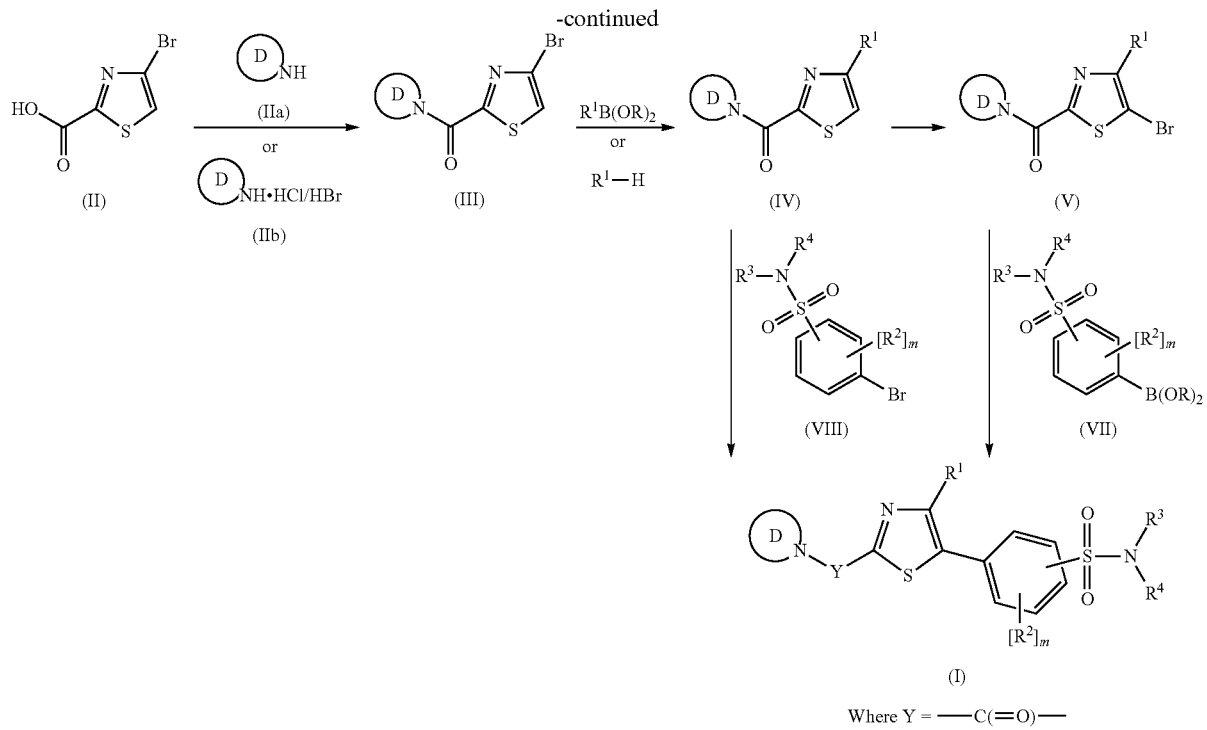

Where Y = —C(=O)—

Scheme 1 shows a method of preparation of the compound of formula (I) (where Y is —C(=O)—, $R^1$, $R^2$, $R^3$, $R^4$, m, and ring D are same as described under compound of generic formula (I)) from 4-bromothiazole-2-carboxylic acid (II).

Compound of formula (II), which in turn can be prepared by the procedures described in the literature WO 2008/057336, is reacted with appropriate amine/amine hydrochloride/amine hydrobromide of formula (IIa/IIb) to obtain compound of formula (III) (where ring D is same as defined in general formula (I)). The coupling reaction can be carried out according to the conditions known for converting carboxylic acids to amides to a person skilled in the art. The reaction may be carried out in the presence of an organic solvent, for example, DMF, THF, a halogenated hydrocarbon such as chloroform and dichloromethane, an aromatic hydrocarbon such as xylene, benzene, toluene, or mixtures thereof or the like, in the presence of suitable base such as triethylamine, diisopropylethylamine, pyridine or the like at a temperature between 0-50° C. using reagents such as 1-(3-dimethylaminopropyl)-3-ethylcarbodiimide hydrochloride (EDCI), 1,3-dicyclohexylcarbodiimide (DCC), and auxiliary reagents such as 1-hydroxy-7-azabenzotriazole (HOAT), hydroxybenzotriazole hydrate (HOBT) or the like. Preferably, coupling is carried out in DMF using EDC, HOBT, and triethylamine as base.

The compound of formula (III) so obtained in the previous step is subjected to Suzuki coupling with $R^1B(OR)_2$ or Buchwald coupling with $R^1$—H (amine) to obtain the compound of formula (IV) (where $R^1$ and ring D are same as defined in general formula (I)). Suzuki coupling can be carried out under different coupling conditions with boronic acids and boronic esters well known in the art. Buchwald coupling can be carried out with $R^1$—H (amine) under different conditions reported in the literature. Preferably, the Suzuki coupling is carried out in a mixture of ethanol and toluene, in presence of base such as potassium phosphate, potassium carbonate or the like, and tetrakis(triphenylphosphine)palladium(0) at a temperature of about 50° C. or higher. Boronic acid used in this reaction can be prepared by the methods well known in the art by hydrolysing the corresponding boronate. Boronates are generally commercially available. Besides, such boronates can also be prepared by reacting an appropriate iodo- or bromo compound with an alkyl lithium such as butyl lithium and then reacting with a borate ester or by methods well known in the art (EP1012142; Review article by N. Miyaura and A. Suzuki, Chem. Rev., 1995, 95, 2547).

Alternatively, compound of the formula (IV) can be prepared starting from compound of formula (VI) (where $R^1$ is substituted- or unsubstituted-aryl, substituted- or unsubstituted-heteroaryl, substituted- or unsubstituted-cycloalkyl). Compound of formula (VI), which in turn can be prepared by the procedures described in the literature US 2007/32531, is reacted with appropriate amine/amine hydrochloride/amine hydrobromide of formula (IIa/IIb) under above mentioned coupling conditions to obtain compound of formula (IV) (where $R^1$ is substituted- or unsubstituted-aryl, substituted- or unsubstituted-heteroaryl, substituted- or unsubstituted-cycloalkyl and ring D is same as defined in general formula (I)).

The compound of formula (IV) on bromination gave compound of formula (V). Bromination can be carried out under a condition generally used in the synthetic organic chemistry using brominating agents such as N-bromosuccinimide, bromine, phosphorous tribromide and aluminium tribromide. In the present invention, bromination has been carried out by using N-bromosuccinimide in DMF. The compound of the formula (V) is subjected to the Suzuki Coupling with boronic acid or boronic ester represented by formula (VII) to obtain compound of the formula (I) (where Y is a —C(=O)—, $R^1$, $R^2$, $R^3$, $R^4$, m, and ring D are same as described under compound of generic formula (I)). The Suzuki coupling can be carried out under same coupling conditions as defined earlier.

Alternatively, compound of the formula (I) can be prepared starting from compound of formula (IV) (where W and ring D are same as defined in general formula (I)). The compound of formula (IV) is subjected to coupling reaction (Direct arylation) with substituted- or unsubstituted-bromobenzenesulphonamide represented by formula (VIII) to obtain compound of the formula (I) (where Y is a —C(=O)—. $R^1$, $R^2$, $R^3$, $R^4$, m, and ring D are same as described under compound of generic formula (I)). Bromobenzenesulphonamides are generally commercially available. Besides, such bromobenzenesulphonamides can also be prepared by methods well known in the art (Bioorg. Med. Chem. Lett., 2007, 17, 3880-85). The coupling reaction can be carried out under a condition generally used in the synthetic organic chemistry (Adv. Synth. Catal., 2009, 351, 1977-1990). The coupling reaction can be carried out in an organic solvent such as N,N-dimethylformamide, N,N-dimethylacetamide, toluene, or the like in presence of potassium carbonate, potassium phosphate or potassium acetate, and a palladium catalyst. In the present invention the coupling reaction has been carried out in dimethyl acetamide in presence of potassium acetate and palladium acetate at a temperature of about 150° C.

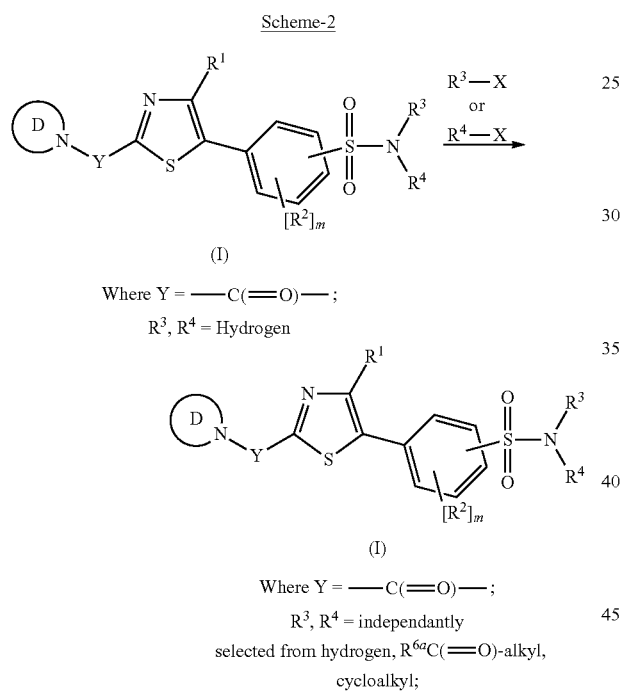

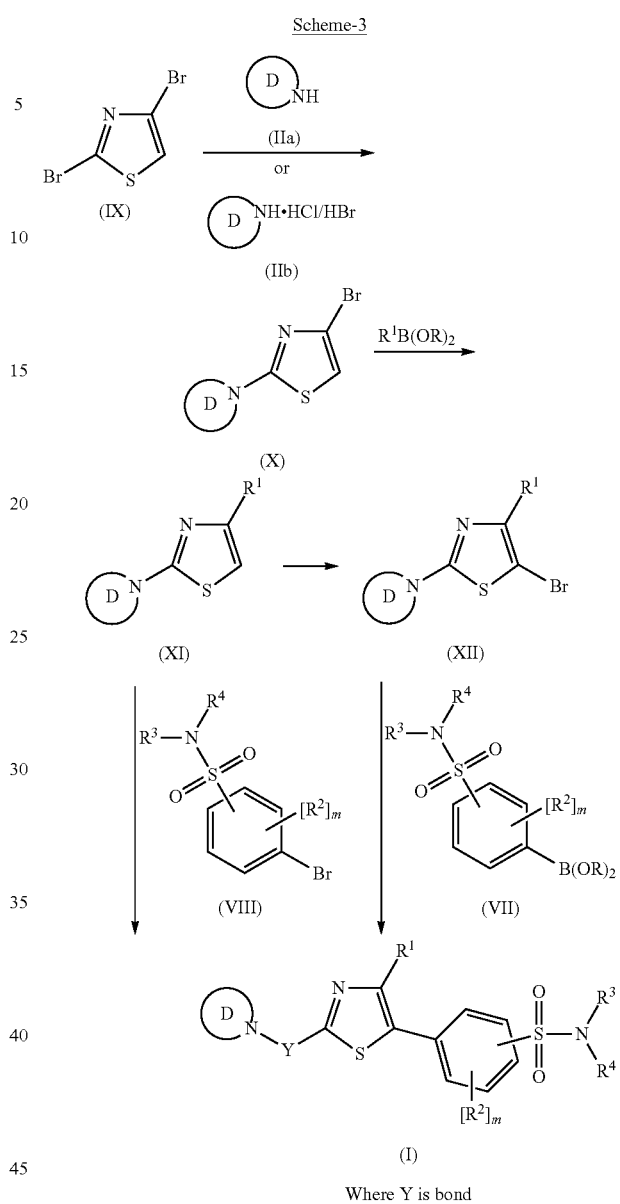

Scheme 2 provides a method of preparation of the compound of formula (I) (where Y is —C(=O)—, $R^3$ and $R^4$ are hydrogen, $R^{6a}$C(=O)—, substituted- or unsubstituted-alkyl, substituted- or unsubstituted-cycloalkyl, $R^1$, $R^2$, m, and ring D are same as described under compound of generic formula (I)) from compound of formula (I) (where Y is —C(=O)—, $R^3$ and $R^4$ are hydrogen, $R^1$, $R^2$, m, and ring D are same as described under compound of generic formula (I)).

Compound of formula (I) (where Y is —C(=O)—, $R^3$ and $R^4$ are hydrogen, $R^1$, $R^2$, m, and ring D are same as described under compound of generic formula (I)), which is prepared by following the synthetic route depicted in the scheme 1, is reacted with $R^3$—X or $R^4$—X (where $R^3$ and $R^4$ are $R^{6a}$C(=O)—, substituted- or unsubstituted-alkyl, substituted- or unsubstituted-cycloalkyl and X is halogen) in presence of base like sodium carbonate, potassium carbonate, pyridine, and triethylamine. Preferably reaction is carried out in potassium carbonate or pyridine as base in DMF as solvent.

Scheme 3 provides a method for preparation of compound of formula (I) (where Y is a bond, $R^1$, $R^2$, $R^3$, $R^4$, m, and ring D are same as described under compound of generic formula (I)), from 2,4-dibromothiazole (IX).

Compound of formula (IX) which is commercially available, is reacted with appropriate amine/amine hydrochloride/amine hydrobromide/lactum of formula (IIa/IIb) to obtain compound of formula (X) (where ring D is same as defined in general formula (I)). The reaction can be carried out in an organic solvent, for example DMF, THF, a halogenated hydrocarbon such as chloroform and dichloromethane, an aromatic hydrocarbon such as xylene, benzene, toluene, or mixtures thereof or the like, in presence of a suitable base such as triethylamine, diisopropylethylamine, pyridine or the like. Preferably, for amine/amine hydrochloride/amine hydrobromide coupling is carried out in DMF and diisopropylethylamine as base. For lactum reaction is carried out under Buchwald coupling condition as reported in the literature.

The compound of the formula (X) as obtained in the previous step is subjected to Suzuki coupling with R¹B(OR)₂ to obtain the compound of formula (XI) (where R¹ and ring D are same as defined in general formula (I)). Suzuki Coupling is carried out by following the similar procedure and condition as described hereinabove under Scheme 1 to obtain compound of formula (XI) (where the definition of R¹ and ring D are the same as defined in general formula (I)).

The compound of the formula (XI) on bromination gave compound of formula (XII). Bromination can be carried out under a condition generally used in the synthetic organic chemistry using brominating agents such as N-bromosuccinimide, bromine, phosphorous tribromide, and aluminiumtribromide. In the present invention, bromination has been carried out by using N-bromosuccinimide in DMF.

The compound of the formula (XII) is then subjected to Suzuki coupling with boronic acid or boronic ester of formula (VII) to obtain compound of formula (I) (where Y is a bond, R¹, R², R³, R⁴, m, and ring D are same as described under compound of generic formula (I)). The Suzuki Coupling is carried out under the conditions described earlier.

Alternatively, compound of the formula (I) can be prepared from compound of formula (XI). The compound of the formula (XI) can be subjected to coupling reaction (Direct arylation) with substituted- or unsubstituted-bromobenzenesulphonamide of formula (VIII) to obtain compound of the formula (I) (where Y is a bond, R¹, R², R³, R⁴, m, and ring D are same as described under compound of generic formula (I)). The coupling reaction can be carried out under a condition as described hereinabove under scheme 1.

Scheme-4

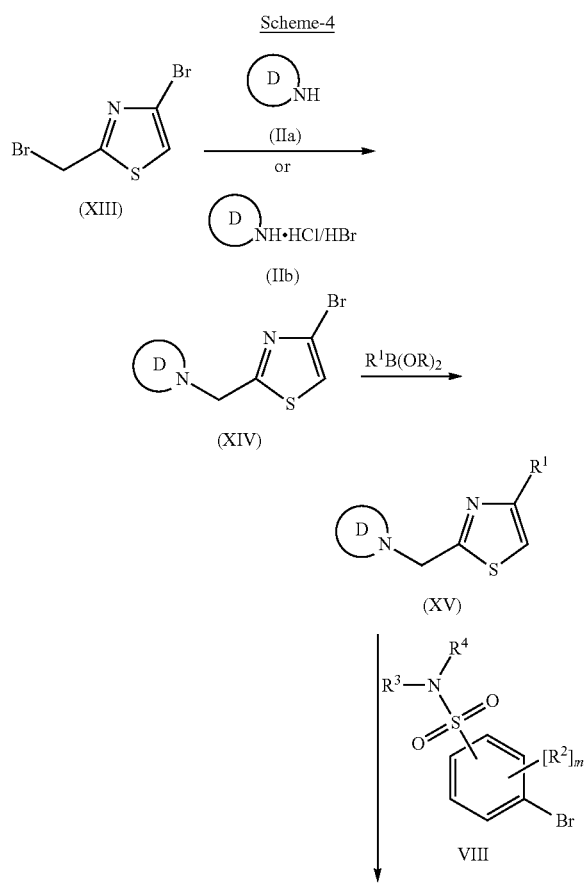

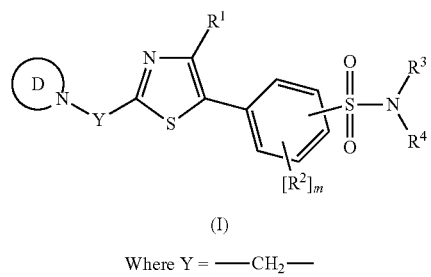

Where Y = —CH₂—

Scheme 4 shows route of synthesis of the compound of the formula (I) (where Y is —CH₂—, R¹, R², R³, R⁴, m, and ring D as described under compound of generic formula (I)) from 4-bromo-2-(bromomethyl)thiazole (XIII).

Compound of formula (XIII), which in turn can be prepared by the procedures described in the literature such as US 2010/298388, is reacted with appropriate amine/amine hydrochloride/amine hydrobromide/lactum of formula (IIa/IIb) to obtain compound of formula (XIV) (where ring D is same as defined earlier). The reaction can be carried out in the presence of an organic solvent, for example DMF, THF, a halogenated hydrocarbon such as chloroform and dichloromethane, an aromatic hydrocarbon such as xylene, benzene, toluene, or mixtures thereof or the like, and a suitable base such as sodium hydride, cesium carbonate, potassium carbonate, triethylamine, diisopropylethylamine, pyridine or the like. Preferably, for amine/amine hydrochloride/amine hydrobromide the coupling reaction is carried out in DMF in presence of potassium carbonate as base. For lactum coupling is carried out in THF in presence of sodium hydride as base.

The compound of formula (XIV) as obtained in the previous step is subjected to Suzuki coupling with R¹B(OR)₂ to obtain the compound of formula (XV) (where R¹ and ring D are same as defined earlier). Suzuki coupling with boronic acid or boronic ester can be carried out under the procedures well known in the art. Preferably, the Suzuki coupling is carried out in a mixture of ethanol, and toluene, in presence of base such as potassium phosphate, potassium carbonate or the like, and tetrakis(triphenylphosphine)palladium(0) at a temperature of about 50° C. or higher.

Compound of the formula (I) can be prepared from compound of formula (XV) (where all symbols are the same as defined in general formula (I)). The compound of the formula (XV) can be subjected to coupling reaction (Direct arylation) with substituted- or unsubstituted-bromobenzenesulphonamide represented by formula (VIII) to obtain the compound of formula (I) (where Y is —CH₂—, R¹, R², R³, R⁴, m, and Ring D are the same as defined earlier). The coupling is carried out under a condition as described hereinabove under scheme 1.

Process for synthesis of the typical intermediate of formula (IIID) is provided herein below in scheme 5, most of the intermediates (IIa/IIb) are commercially available or their syntheses are reported in the literature (US 2005/80095, U.S. Pat. No. 3,953,596, WO 2008/84300, US 2004/157849).

Scheme-5

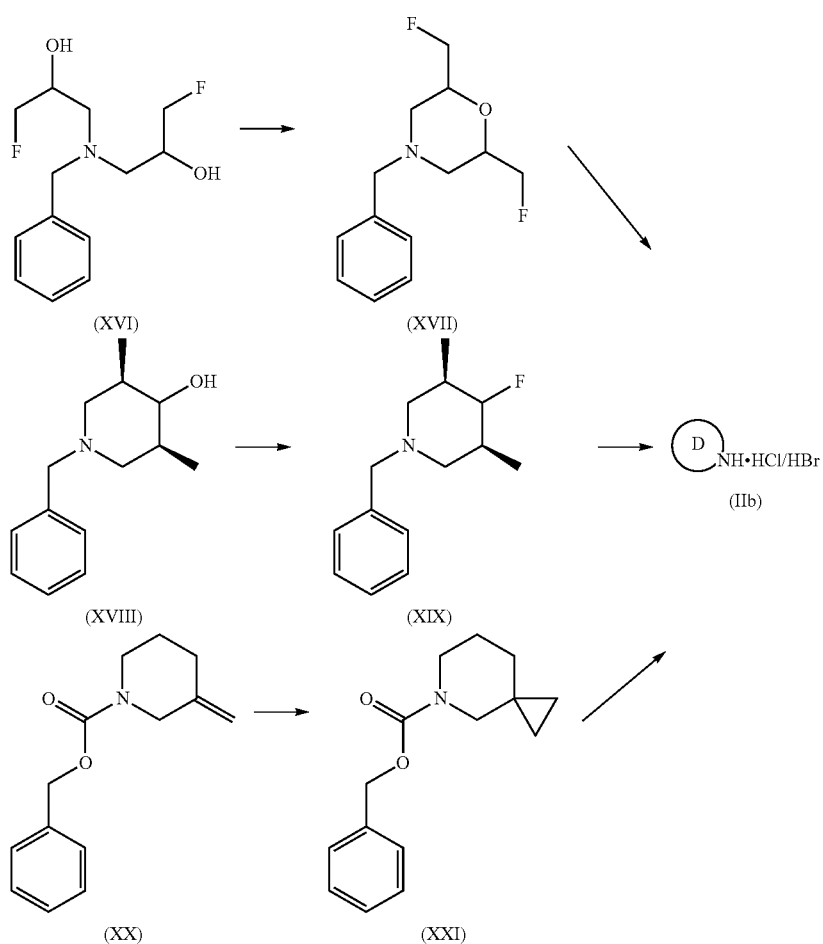

Scheme 5 shows method of preparation of (IIb) from 3,3'-(benzylazanediyl)bis(1-fluoropropan-2-ol) (XVI), which is prepared by condensation of 2-(fluoromethyl)oxirane and benzyl amine in methanol at 80° C. The compound of the formula (XVI) so obtained in the previous step is cyclized by mono tosylation followed by nucleophilic displacement in presence of base to obtain the compound of the formula (XVII). Cyclization is carried out in presence of Tris(2-(2-methoxyethoxy)ethyl)amine at 0° C. in dioxane as solvent. De-benzylation of the compound of the formula (IIb) is carried out in presence of 10% Pd/C as catalyst in hydrogen pressure.

Compound of the formula (XVIII) which in turn can be prepared by the procedure reported in the literature WO 2005/77932 is reacted with Diethylaminosulfur trifluoride to obtain the compound of the formula (XIX). The compound of the formula (XIX) so obtained in the previous step is de-benzylated by above mentioned condition to obtain the compound of the formula (IIb).

In another aspect compound of the formula (IIb) is synthesized from compound of the formula (XXI) by de-protection of benzyl carboxylate using HBr in acetic acid. Compound of the formula (XXI) is prepared by cyclopropanation from the compound of the formula (XX) which is prepared by the procedure reported in the European Journal of Medicinal Chemistry, 1991, 26, 625-631.

The term 'room temperature' denotes any temperature ranging between about 20° C. to about 40° C., except and otherwise it is specifically mentioned in the specification.

The intermediates and the compounds of the present invention may obtained in pure form in a manner known per se, for example, by distilling off the solvent in vacuum and re-crystallizing the residue obtained from a suitable solvent, such as pentane, diethyl ether, isopropyl ether, chloroform, dichloromethane, ethyl acetate, acetone or their combinations or subjecting it to one of the purification methods, such as column chromatography (e.g., flash chromatography) on a suitable support material such as alumina or silica gel using eluent such as dichloromethane, ethyl acetate, hexane, methanol, acetone, and their combinations. Preparative LC-MS method is also used for the purification of molecules described herein.

Salts of compound of formula I can be obtained by dissolving the compound in a suitable solvent, for example in a chlorinated hydrocarbon, such as methyl chloride or chloroform or a low molecular weight aliphatic alcohol, for example, ethanol or isopropanol, which was then treated with the desired acid or base as described in Berge S. M. et al. "Pharmaceutical Salts, a review article in Journal of Pharmaceutical sciences volume 66, page 1-19 (1977)" and in handbook of pharmaceutical salts properties, selection, and use by P. H. Einrich Stahl and Camille G. Wermuth, Wiley-VCH (2002). Lists of suitable salts can also be found in *Remington's Pharmaceutical Sciences,* 18th ed., Mack Publishing Company, Easton, Pa., 1990, p. 1445, and *Journal of Pharmaceutical Science,* 66, 2-19 (1977). For example, they can be a salt of an alkali metal (e.g., sodium or potassium), alkaline earth metal (e.g., calcium), or ammonium of salt.

The compound of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, potassium hydroxide. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The stereoisomers of the compounds of formula I of the present invention may be prepared by stereospecific syntheses or resolution of the achiral compound using an optically active amine, acid or complex forming agent, and separating the diastereomeric salt/complex by fractional crystallization or by column chromatography.

Modulation of the nicotinic cholinergic receptors, particularly $\alpha 7$ may provide for efficacy in a range of cognitive states, right from pre-attention to attention and subsequently working, reference and recognition memory. Accordingly, this invention may find application in the treatment and prophylaxis of multitude of disease conditions including, either one or combinations of, schizophrenia, schizophreniform disorder, cognitive deficits in schizophrenia, brief psychotic disorder, delusional disorder, schizoaffective disorder, shared psychotic disorder, paranoid personality disorder, schizoid personality disorder, schizotypal personality disorder, attention deficit disorder, attention deficit hyperactivity disorder, depression, maniac depression, major depressive disorder, posttraumatic stress disorder, generalized anxiety disorder, tourette's syndrome, cyclothymic disorder, dysthymic disorder, agoraphobia, panic disorder (with or without agoraphobia), phobias (including social phobia) and bipolar disorders (Thomsen M S, et al., Curr. Pharm. Des., 2010, 16, 323-343; Peng Z Z, et al., Zhonghua Yi Xue Yi Chuan Xue Za Zhi, 2008, 25, 154-158; Young J W, et al., Eur. Neuropsychopharmacol., 2007, 17, 145-155; Martin L F, et al., Am. J. Med. Genet., B Neuropsychiatr. Genet., 2007, 144B, 611-614; Martin L F, et al., Psychopharmacology (Berl), 2004, 174, 54-64; Feher A, et al., Dement. Geriatr. Cogn. Disord., 2009, 28, 56-62; Wilens T E, et al., Biochem. Pharmacol., 2007, 74, 1212-1223; Verbois S L, et al., Neuropharmacology, 2003, 44, 224-233; Sanberg P R, et al., Pharmacol. Ther., 1997, 74, 21-25). Cholinergic system, particularly through $\alpha 7$ nAChR seems to have implications in traumatic brain injury-induced psychosis. Chronic nicotine treatment has shown to attenuate same. Thus, this invention may also find application in the treatment of deficits in cholinergic $\alpha 7$ nAChR following traumatic brain injury (Bennouna M, et al., Encephale, 2007, 33, 616-620; Verbois S L, et al., Neuropharmacology, 2003, 44, 224-233).

Modulation of nicotinic ACh receptors, particularly the $\alpha 7$ subtype could also help supplement the down-regulated cholinergic receptor expression and transmission as in dementia(s), and also slowing disease progression by reduction of $\alpha 7$-$\alpha 3142$ complexation and internalization in AD and Down's syndrome (Nordberg A, et al., Neurotox. Res., 2000, 2, 157-165; Haydar S N, et al., Bioorg. Med. Chem., 2009, 17, 5247-5258; Deutsch S I, et al., Clin. Neuropharmacol., 2003, 26, 277-283). Appropriately, this invention may find application in the treatment and prophylaxis of multitude of disease conditions including, either one or combinations of, dementia(s) due to Alzheimer's disease, dementia with Lewy bodies, Down's syndrome, head trauma, Stroke, hypoperfusion, Parkinson's disease, Huntington's disease, Prion diseases, progressive supranuclear palsy, radiation therapy, brain tumors, normal-pressure hydrocephalus, subdural hematoma, human immunodeficiency virus (HIV) infection, vitamin deficiency, hypothyroidism, drugs, alcohol, lead, mercury, aluminium, heavy metals, syphilis, Lyme disease, viral encephalitis, fungal infection and cryptococcosis (Zhao X, et al., Ann. N. Y. Acad. Sci., 2001, 939, 179-186; Perry E, et al., Eur. J. Pharmacol., 2000, 393, 215-222; Harrington C R, et al., Dementia, 1994, 5, 215-228; Wang J, et al., J. Neurosci. Res., 2010, 88, 807-815; Duris K, et al., Stroke 2011, 42(12), 3530-6). Thus, this invention may also find application in the prophylaxis and preventive measures immediately after early-stage identification of neurodegenerative disease like Alzheimer's disease and Parkinson's disease.

Modulation of nicotinic ACh receptors particularly $\alpha 4\beta 2$, $\alpha 3\beta 4$ and $\alpha 7$ may have implications in the development of therapies for nicotine, *cannabis* addiction and relapse prevention. Accordingly, this invention may find application in the prophylaxis or therapy of nicotine addiction, *cannabis* addiction, and relapse prevention of nicotine or *cannabis* addiction. Additionally, this invention may also provide for an alternative therapy for non-responding addiction patients, patients having intolerable side-effects with de-addiction therapies or those requiring long-term maintenance therapies. (Kuzmin A, et al., Psychopharmacology (Berl), 2009, 203, 99-108; Weiss R B, et al., PLoS Genet., 2008, 4, e1000125: Solinas M, et al., J. Neurosci., 2007, 27, 5615-5620; Ebbert J O, et al., Patient. Prefer. Adherence, 2010, 4, 355-362)

This invention may also find application in the treatment and prophylaxis of multitude of pain conditions including, either one or combinations of, pain arising from, peripheral nervous system (PNS), post-diabetic neuralgia (PDN), post-herpetic neuralgia (PHN), multiple sclerosis, Parkinson's disease, low-back pain, fibromyalgia, post-operative pain, acute pain, chronic pain, mononeuropathy, primary lateral sclerosis, pseudobulbar palsy, progressive muscular palsy, progressive bulbar palsy, postpolio syndrome, diabetes induced polyneuropathy, acute demyelinating polyneuropathy (Guillain-Barre syndrome), acute spinal muscular atrophy (Werdnig-Hoffman disease) and secondary neurodegeneration (Donnelly-Roberts D L, et al., J. Pharmacol. Exp. Ther., 1998, 285, 777-786; Rowley T J, et al., Br. J. Anaesth., 2010, 105, 201-207; Bruchfeld A, et al., J. Intern. Med., 2010, 268, 94-101).

This invention may find application in the treatment and prophylaxis of plethora of inflammation and pain related states involving TNF-$\alpha$ and thus providing symptomatic relief in either any one or combination of, rheumatoid arthritis, bone resorption diseases, atherosclerosis, inflammatory bowel disease, Crohn's disease, inflammation, cancer pain, muscle degeneration, osteoarthritis, osteoporosis, ulcerative colitis, rhinitis, pancreatitis, spondylitis, acute respiratory distress syndrome (ARDS), joint inflammation, anaphylaxis, ischemia reperfusion injury, multiple sclerosis, cerebral malaria, septic shock, tissue rejection of graft, brain trauma, toxic shock syndrome, herpes virus infection (HSV-1 & HSV-2), herpes zoster infection, sepsis, fever, myalgias, asthma, uveitis, contact dermatitis, obesity-related disease, and endotoxemia (Giebelen T, et al., Shock, 2007, 27, 443-447; Pena G, et al., Eur. J. Immunol., 2010, 40, 2580-2589).

Thus the present invention further provides a pharmaceutical composition, containing the compounds of the general formula (I) as defined above, its tautomeric forms, its stereoisomers, its pharmaceutically acceptable salts, its polymorphs, its solvates, and its optical isomers in combination with the usual pharmaceutically acceptable carriers, diluents, and the like.

The pharmaceutically acceptable carrier (or excipient) is preferably one that is chemically inert to the compound of the invention and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting.

The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See Pharmaceutics and Pharmacy Practice, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as polyethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents, and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the compound ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

A compound of the present invention, alone or in combination with other suitable components, can be made into aerosol formulations to be administered via inhalation. A compound or epimer of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric, and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, the compound of the invention can be made into suppositories by mixing with a variety of bases, such as emulsifying bases or water-soluble bases.

Formulations suitable for vaginal administration can be presented as pessaries, tampons, creams, gels, pastes, foams, or spray formulas containing, in addition to the compound ingredient, such carriers as are known in the art to be appropriate.

The concentration of the compound in the pharmaceutical formulations can vary, e.g., from less than about 1% to about 10%, to as much as 20% to 50% or more by weight, and can be selected primarily by fluid volumes, and viscosities, in accordance with the particular mode of administration selected.

For example, a typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, Remington's Pharmaceutical Science (17$^{th}$ ed., Mack Publishing Company, Easton, Pa., 1985).

It will be appreciated by one of ordinary skill in the art that, in addition to the aforedescribed pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka, et al., Ann. Rev. Biophys. Bioeng., 9, 467 (1980) and U.S. Pat. Nos. 4,235,871, 4,501,728, 4,837, 028, and 5,019,369.

The compounds or pharmaceutical compositions are useful, in an embodiment, for the treatment and/or prophylaxis of diseases or disorder or condition such as Alzheimer's disease (AD), mild cognitive impairment (MCI), senile dementia, vascular dementia, dementia of Parkinson's disease, attention deficit disorder, attention deficit hyperactivity disorder (ADHD), dementia associated with Lewy bodies, AIDS dementia complex (ADC), Pick's disease, dementia associated with Down's syndrome, Huntington's disease, cognitive deficits associated with traumatic brain injury (TBI), cognitive decline associated with stroke, poststroke neuroprotection, cognitive and sensorimotor gating deficits associated with schizophrenia, cognitive deficits associated with bipolar disorder, cognitive impairments associated with depression, acute pain, post-surgical or post-operative pain, chronic pain, inflammation, inflammatory pain, neuropathic pain, smoking cessation, need for new blood vessel growth associated with wound healing, need for new blood vessel growth associated with vascularization of skin grafts, and lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, and rheumatoid spondylitis.

In another embodiment, the pharmaceutical compositions are useful for the treatment and/or prophylaxis of diseases or disorder or condition classified or diagnosed as major or minor neurocognitive disorders, or disorders arising due to neurodegeneration.

The present invention also provide method of administering a compound of formula I, as defined hereinabove in combination with or as adjunct to medications used in the treatment of attention deficit hyperactivity disorders, schizophrenia, and other cognitive disorders such as Alzheimer's disease, Parkinson's dementia, vascular dementia or dementia associated with Lewy bodies, traumatic brain injury.

The present invention also provide method of administering a compound of formula I, as defined hereinabove in combination with or as an adjunct to acetylcholinesterase inhibitors, disease modifying drugs or biologics for neurodegenerative disorders, dopaminergic drugs, antidepressants, typical or an atypical antipsychotic.

Accordingly, compound of formula I is useful for preventing or treating a disorder mediated by nicotinic acetylcholine receptors. Such compounds can be administered to a subject having such a disorder or susceptible to such disorders in a therapeutically effective amount. The compounds are particularly useful for a method of treating a mammal having a condition where modulation of nicotinic acetylcholine receptor activity is of therapeutic benefit, wherein the method is accomplished by administering a therapeutically effective amount of a compound of formula I to a subject having, or susceptible to, such a disorder.

The present invention also provides a pharmaceutical composition, containing the compounds of the general formula (I) as defined above, its tautomeric forms, its stereoisomers, its isotopes, its pharmaceutically acceptable salts, its polymorphs, its solvates, and its optical isomers in combination with the usual pharmaceutically employed carriers, diluents, and the like, and for use in any of the methods described herein.

The compounds of the invention can be administered in a dose sufficient to treat the disease, condition or disorder. Such doses are known in the art (see, for example, the *Physicians' Desk Reference* (2004)). The compounds can be administered using techniques such as those described in, for example, Wasserman, et al., Cancer, 36, pp. 1258-1268 (1975) and *Physicians' Desk Reference,* 58th ed., Thomson PDR (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present method can involve the administration of about 0.1 µg to about 50 mg of at least one compound of the invention per kg body weight of the individual. For a 70 kg patient, dosages of from about 10 µg to about 200 mg of the compound of the invention would be more commonly used, depending on a patient's physiological response.

By way of example and not intending to limit the invention, the dose of the pharmaceutically active agent(s) described herein for methods of treating or preventing a disease or condition as described above can be about 0.001 to about 1 mg/kg body weight of the subject per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. The dose of the pharmaceutically active agent(s) described herein for the described methods can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

In accordance with embodiments, the present invention provides methods of treating, preventing, ameliorating, and/or inhibiting a condition modulated by the nicotinic acetylcholine receptor comprising administering a compound of formula (I) or a salt thereof.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the inventive methods can provide any amount of any level of treatment, prevention, amelioration, or inhibition of the disorder in a mammal. For example, a disorder, including symptoms or conditions thereof, may be reduced by, for example, 100%, 90%, 80%, 70%, 60%, 50%. 40%, 30%, 20%, or 10%. Furthermore, the treatment, prevention, amelioration, or inhibition provided by the inventive method can include treatment, prevention, amelioration, or inhibition of one or more conditions or symptoms of the disorder, e.g., cancer. Also, for purposes herein, "treatment," "prevention," "amelioration," or "inhibition" can encompass delaying the onset of the disorder, or a symptom or condition thereof.

In accordance with the invention, the term subject includes an "animal" which in turn includes a mammal such as, without limitation, the order Rodentia, such as mice, and the order Lagomorpha, such as rabbits. It is preferred that the mammals are from the order Carnivora, including Felines (cats) and Canines (dogs). It is more preferred that the mammals are from the order Artiodactyla, including Bovines (cows) and Swine (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Following are the abbreviations used and meaning thereof in the specification:

ACh: Acetylcholine.
AD: Alzheimer's disease.
ADC: AIDS dementia complex.
ADHD: attention deficit hyperactivity disorder.
AIDS: Acquired immunodeficiency syndrome.
ARDS: acute respiratory distress syndrome.
DCC: 1,3-dicyclohexylcarbodiimide.
DCE: dichloroethane.
DCM: dichloromethane.
DIPEA: diisopropyl ethyl amine
DLB: dementia with Lewy bodies.
DMF: N,N-dimethylformamide.
EDCI: 1-(3-dimethylaminopropyl)-3-ethylcarbodiimide hydrochloride.
FLIPR: Fluorometric Imaging Plate Reader.
HATU: 2-(1H-7-Azabenzotri azol-1-yl)-1,1,3,3-tetram ethyl uronium hexafluorophosphate.
HBSS: Hank's balanced salt solution.
HEPES: 4-(2-hydroxyethyl)piperazine-1-ethanesulfonic acid.
HMGB: high mobility group box.
HOAT: 1-hydroxy-7-azabenzotriazole.
HOBT: hydroxybenzotriazole hydrate.
HPLC: High Performance liquid chromatography.
IL: interleukins.
LDT: laterodorsal tegmental nucleus.
LGIC: ligand-gated ion channels.
MCI: mild cognitive impairment.
NBS: N-bromosuccinimide.
NCS: N-chlorosuccinimide.
NIS: N-iodosuccinamide
NNRs: Neural nicotinic ACh receptors.
PAM: positive allosteric modulation.
PD: Parkinson's disease.
PDN: post-diabetic neuralgia.
PHN: post-herpetic neuralgia.
PMBO: p-methoxy benzyloxy.
PNS: peripheral nervous system.
TBI: traumatic brain injury.
THF: Tetrahydrofuran.
TLC: Thin layer chromatography.
TMS: tetramethylsilane.
TNF-α: tumor necrosis factor alpha.
VTA: ventral tegmental area.
α7 nAChR: nicotinic acetylcholine receptor α7 subunit.

The following examples are provided to further illustrate the present invention and therefore should not be construed in any way to limit the scope of the present invention. All $^1$HNMR spectra were determined in the solvents indicated and chemical shifts are reported in δ units downfield from the internal standard tetramethylsilane (TMS) and interproton coupling constants are reported in Hertz (Hz).

Example 1

Preparation of Intermediates

Intermediate 1: Preparation of 2,6-bis(fluoromethyl)morpholine hydrochloride

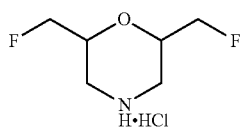

Step 1: 3,3'-(benzylazanediyfibis (1-fluoropropan-2-ol)

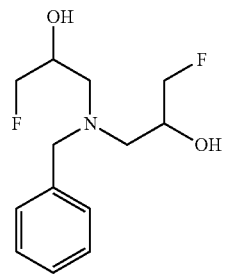 [SMILES: OC(CF)CN(Cc1ccccc1)CC(O)CF]

2-(fluoromethyl)oxirane (5.0 g, 65.70 mmol) and benzyl amine (3.52 g. 32.90 mmol) were added in methanol (50 ml) and heated at 80° C. for 17 hr. The progress of reaction was monitored by TLC. Reaction mixture was concentrated under reduced pressure to remove solvent; residue was purified by flash column chromatography using 40% ethyl acetate in hexanes as an eluent to obtain the title compound (8.3 g, 97.4%)

MS: m/z 260 (M+1);

$^1$HNMR (CDCl$_3$, 400 MHz): δ 7.39-7.29 (m, 5H), 4.51-4.44 (m, 1H). 4.41-4.32 (m, 2H), 4.30-4.23 (m, 1H), 4.01-3.88 (m, 3H), 3.76 (s, 2H), 2.95 (bs-exchanges with D$_2$O, 2H), 2.78-2.64 (m, 4H).

Step 2: 4-benzyl-2,6-bis(fluoromethyl)morpholine

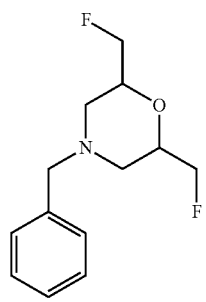 [SMILES: FCC1CN(Cc2ccccc2)CC(CF)O1]

Tris(2-(2-methoxyethoxy)ethyl)amine (1.06 g, 3.28 mmol) and potassium hydroxide (3.68 g, 65.60 mmol) were added to a solution of 3,3'-(benzylazanediyl)bis(1-fluoropropan-2-ol) (step 1 of intermediate 1, 8.5 g, 32.80 mmol) in 1,4-Dioxane (150 ml). Reaction mixture was cooled to 0° C. and solution of Tosyl chloride (6.25 g, 1.93 mmol) in 1,4-Dioxane (50 ml) was added slowly. The reaction mixture was stirred at 0° C. for 1 hr. The reaction mixture then allowed to come to room temperature and stirred for 18 hr. The progress of reaction was monitored by TLC. Reaction mixture was filtered through celite and washed with 1,4-Dioxane (50 ml). Combined filtrate was concentrated under reduced pressure. Residue obtained was diluted with 2N HCl (100 ml) and extracted with ethyl acetate (2×50 ml). The aqueous layer separated was cooled to 0° C. and neutralized by adding aqueous NaOH solution. The aqueous layer was extracted with ethyl acetate (2×50 ml). The combined organic layer was washed with brine (150 ml), dried over sodium sulphate and concentrated under reduced pressure to obtain a crude product; which was purified by flash column chromatography to obtain the title compound (3.5 g, 44.3%). MS: m/z 243 (M+1).

$^1$HNMR (CDCl$_3$, 400 MHz): δ 7.44-7.28 (m, 5H), 4.72-4.67 (m, 1H), 4.58-4.50 (m, 2H), 4.47-4.38 (m, 1H), 4.20-4.09 (m, 2H), 3.50 (s, 2H), 2.60-2.54 (m, 2H), 2.44-2.36 (m, 2H).

Step 3: 2,6-bis(fluoromethyl)morpholine hydrochloride

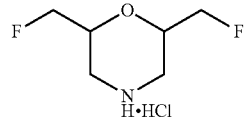

To a stirred solution of 4-benzyl-2,6-bis(fluoromethyl) morpholine (step 2, 3.5 g, 14.51 mmol) in methanol (100 ml) was added 10% Pd/C (0.5 g) at 25° C. Reaction mixture was stirred under Hydrogen for 15 hr. The progress of reaction was monitored by TLC. Reaction mixture was filtered through celite, washed with methanol 20 ml. To the filtrate was added HCl in methanol (3M, 30 ml) and stirred at 25° C. for 30 min. The reaction mixture was concentrated under reduced pressure to obtain title compound (2.1 g, 99%).

Intermediate 2: Preparation of 4-fluoro-cis-3,5-dimethylpiperidine hydrochloride

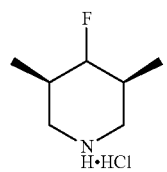

Step 1: 1-benzyl-4-fluoro-cis-3,5-dimethylpiperidine

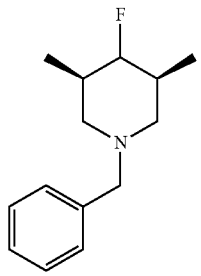 [SMILES: C[C@@H]1CN(Cc2ccccc2)C[C@H](C)C1F]

Diethylaminosulfur trifluoride (7.35 g, 6.0 ml, 45.60 mmol) was added drop wise to a stirred solution of 1-benzyl-cis-3,5-dimethylpiperidin-4-ol (prepared according to the procedure given in WO 2005/77932, 5.0 g, 22.80 mmol) in dichloromethane (50 ml) at −50° C. Reaction mixture was allowed to come at room temperature and stirred at 25° C. for 18 hr. The progress of reaction was monitored by TLC. Reaction mixture was quenched with saturated aqueous sodium bicarbonate solution (20 ml) and extracted with dichloromethane (2×100 ml). The combined organic layer was washed with water (100 ml), dried over sodium sulphate and concentrated under reduced pressure to obtain a crude product (3.5 g, 69.4%). MS: m/z 222 (M+1).

$^1$HNMR (CDCl$_3$, 400 MHz): δ 7.39-7.26 (m, 5H). 3.49 (s, 2H), 3.60 (dt, J=50.0, 10.0 Hz, 1H), 2.88-2.82 (m, 2H), 2.01-1.90 (m. 2H), 1.73 (t, J=11.2 Hz, 2H), 0.98 (d, J=6.4 Hz, 6H).

Step 2: 4-fluoro-cis-3,5-dimethylpiperidine hydrochloride

To a stirred solution of 1-benzyl-4-fluoro-cis-3,5-dimethylpiperidine (step 1 of intermediate 2, 3.5 g, 15.81 mmol) in methanol (20 ml) was added 10% Pd/C (1.70 g) at 25° C. Reaction mixture was stirred under Hydrogen for 7 hr. The progress of reaction was monitored by TLC. Reaction mixture was filtered through celite, washed with methanol (20 ml). To the filtrate was added HCl in methanol (3M, 30 ml) and stirred at 25° C. for 30 min. Reaction mixture was concentrated under reduced pressure to obtain title compound (2.55 g, 96.2%). MS: m/z 132 (M+1).

$^1$HNMR (DMSO, 400 MHz): δ 9.45 (br-s, exchanges with D$_2$O, 1H), 4.01 (dt, J=50.0, 10.0 Hz, 1H), 3.24-3.16 (m, 2H), 2.72-2.58 (m, 2H), 2.12-2.02 (m, 2H), 0.98 (d, J=6.4 Hz, 6H).

Intermediate 3: Preparation of 5-azaspiro[2.5]octane hydrobromide

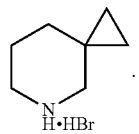

Step 1: benzyl 5-azaspiro[2.5]octane-5-carboxylate

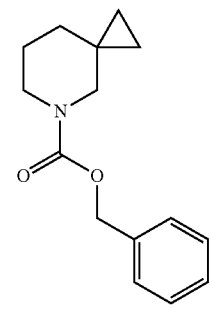 [SMILES: O=C(OCc1ccccc1)N1CCCC2(CC2)C1]

To a stirred solution of Diethyl zinc (1.38 g, 11.2 ml, 1 M solution in hexane 11.24 mmol) in dichloromethane (10 ml) was added trifluoroacetic acid (1.28 g, 0.84 ml, 11.24 mmol) drop wise manner at 0° C. Diiodomethane (3.01 g, 0.90 ml, 11.24 mmol) in dichloromethane (5 ml) was added and reaction mixture was stirred at 0° C. for 30 min. A solution of benzyl 3-methylenepiperidine-1-carboxylate (prepared according to the procedure given in European Journal of Medicinal Chemistry 1991, 26, 625-631), (1.3 g, 5.62 mmol) in dichloromethane (10 ml) was added and reaction mixture stirred at 0° C. for 30 min and then at 25° C. for 18 hr. The progress of reaction was monitored by TLC. Reaction mixture was diluted with dichloromethane (25 ml) and poured in to a saturated solution of sodium bicarbonate (50 ml). Solid precipitated out was filtered, organic layer was separated and dried over sodium sulphate and concentrated under reduced pressure to obtain a crude product, which was purified by flash column chromatography using 6% ethyl acetate in hexanes to obtain the title compound (0.95 g, 68.9%). MS: m/z 246 (M+1).

$^1$HNMR (CDCl$_3$, 400 MHz): δ 7.38-7.32 (m, 5H), 5.17-5.08 (m, 2H), 4.87-4.79 (m, 1H), 3.97 (s, 1H), 3.56-3.48 (m, 2H), 3.25-3.18 (m, 2H), 2.31-2.25 (m, 2H), 1.62-1.58 (m, 1H), 1.46-1.40 (m, 1H), 0.52-0.38 (m, 1H), 0.30-0.25 (m, 1H).

Step 2: 5-azaspiro[2.5]octane hydrobromide

HBr (6.16 g, 4.13 ml, 30% solution in glacial acetic acid, 22.83 mmol) was added to a benzyl 5-azaspiro[2.5]octane-5-carboxylate (step 1 of intermediate 3, 2.8 g, 11.41 mmol) at 0° C. Reaction mixture was stirred at 25° C. for 3 hr. The progress of reaction was monitored by TLC. Reaction mixture was diluted with hexane (25 ml) and stirred for 15 min at 25° C. Organic layer was separated and solid was again stirred with diethyl ether (25 ml). Solvent layer was removed by decanting and solid was dried to obtain the title compound (1.86 g, 85%). MS: m/z 112 (M+1).

Example 2

Preparation of 4-(2-(3-oxa-S-azabicyclo[3.2.1]oc-tane-8-carbonyl)-4-(4-chlorophenyl) thiazol-5-yl) benzenesulfonamide (Compound 68)

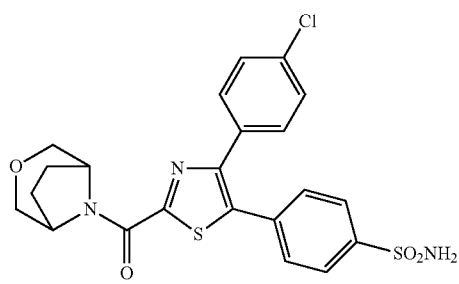 [SMILES: NS(=O)(=O)c1ccc(-c2sc(C(=O)N3C4CCC3COC4)nc2-c2ccc(Cl)cc2)cc1]

Step 1: 3-oxa-8-azabicyclo[3.2.1]octan-8-yl(4-bromothiazol-2-yl)methanone

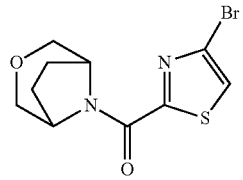 [SMILES: O=C(c1nc(Br)cs1)N1C2CCC1COC2]

To a solution of 4-bromothiazole-2-carboxylic acid (prepared according to the procedure given in WO 2008/57336, 1.4 g, 6.73 mmol) in DMF (15 ml) was added HOBT (1.13 g, 7.40 mmol) at room temperature, followed by the addition of 3-oxa-8-azabicyclo[3.2.1]octane (prepared according to the procedure given in WO 2010/120854, 0.76 g, 6.69 mmol). Reaction mixture was cooled to 0° C. and to this were added EDC (1.93 g, 10.10 mmol) and triethylamine (3.40 g, 4.69 ml, 33.60 mmol). Reaction mixture was stirred at room temperature for 15 hr. The progress of reaction was monitored by TLC. The reaction mixture was concentrated under reduced pressure. The residue so obtained was taken in ethyl acetate (150 ml) and washed with saturated sodium bicarbonate solution (1×40 ml), brine (1×20 ml). The organic layers separated were dried over anhydrous sodium sulphate, filtered and concentrated under reduced pressure to get a crude product. This crude product was purified by column chromatography over silica gel (100-200 mesh) using 2.5% methanol in DCM as an eluent to obtain the title compound (0.35 g. 17.15%). MS: m/z 304 (M+1).

¹HNMR (CDCl₃, 400 MHz): δ 7.47 (s, 1H), 5.72 (d, J=5.6 Hz, 1H), 4.76 (d, J=7.2 Hz, 1H), 3.86-3.74 (m, 4H), 2.18-1.98 (m, 4H).

Step 2: 3-oxa-8-azabicyclo[3.2.1]octan-8-yl(4-(4-chlorophenyl)thiazol-2-yl)methanone

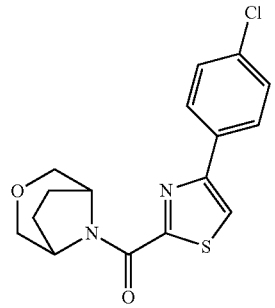 [SMILES: O=C(c1nc(-c2ccc(Cl)cc2)cs1)N1C2CCC1COC2]

To a solution of 3-oxa-8-azabicyclo[3.2.1]octan-8-yl(4-bromothiazol-2-yl)methanone (Step-1 of compound 68, 0.35 g, 1.15 mmol) in a mixture of toluene:ethanol (2.5 ml: 7.5 ml) were added (4-chlorophenyl) boronic acid (0.2 g, 1.27 mmol) and potassium carbonate (0.34 g, 2.42 mmol) at 25° C. in a tube, nitrogen gas was bubbled through reaction mixture for 15 minutes. To the reaction mixture was added tetrakis(triphenylphosphine)palladium(0) (0.07 g, 0.06 mmol) under nitrogen, tube was sealed and reaction mixture was heated at 90-95° C. for 18 hr with stirring. The progress of reaction was monitored by TLC. The reaction mixture was cooled to 25° C. and filtered through celite. The residue was washed with ethanol (2×20 ml). The filtrate was concentrated under reduced pressure to obtain a crude product. This crude product was purified by column chromatography over silica gel (100-200 mesh) using 35% ethyl acetate in hexanes as an eluent to obtain the title compound (0.2 g, 51.7%). MS: m/z 335 (M+1).

¹HNMR (CDCl₃, 400 MHz): δ 7.80 (d, J=8.8 Hz, 2H), 7.70 (s, 1H), 7.43 (d, J=8.8 Hz, 2H), 5.85 (d, J=5.6 Hz, 1H), 4.81 (d, J=6.8 Hz, 1H), 3.95-3.67 (m, 4H), 2.23-1.99 (m, 4H).

Step 3

3-oxa-8-azabicyclo[3.2.1]octan-8-yl(5-bromo-4-(4-chlorophenyl)thiazol-2-yl)methanone

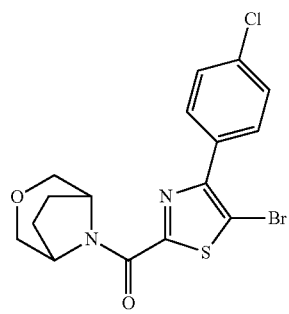 [SMILES: O=C(c1nc(-c2ccc(Cl)cc2)c(Br)s1)N1C2CCC1COC2]

To a stirred solution 3-oxa-8-azabicyclo[3.2.1]octan-8-yl (4-(4-chlorophenyl)thiazol-2-yl)methanone (Step-2 of compound 68, 0.2 g, 0.60 mmol) in DMF (10 ml) at 0° C. was added N-bromosuccinimide (0.10 g, 0.60 mmol) in a portionwise manner. The resulting reaction mixture was stirred at 50-55° C. for 4 hrs. The progress of reaction was monitored by TLC. The reaction mixture was cooled to room temperature, water (40 ml) was added slowly and aqueous layer was extracted with ethyl acetate (2×50 ml). The organic layer was washed with water (1×30 ml). Combined organic layer was dried over anhydrous $Na_2SO_4$. The solvent was evaporated under reduced pressure to obtain a crude product; which was purified by flash column chromatography using 20% ethyl acetate in hexanes as an eluent to obtain the title compound (0.12 g, 48.6%). MS: m/z 414 (M+1).

$^1$HNMR (CDCl$_3$, 400 MHz): δ 7.85 (d, J=8.4 Hz, 2H), 7.45 (d, J=8.4 Hz, 2H), 5.73 (d, J=5.6 Hz, 1H), 4.76 (d, J=6.4 Hz, 1H), 3.86 (d, J=10.8 Hz, 2H), 3.75 (t, J=10.8 Hz, 2H), 2.17-1.98 (m, 4H).

Step 4: 4-(2-(3-oxa-8-azabicyclo[3.2.1]octane-8-carbonyl)-4-(4-chlorophenyl)thiazol-5-yl)benzenesulfonamide

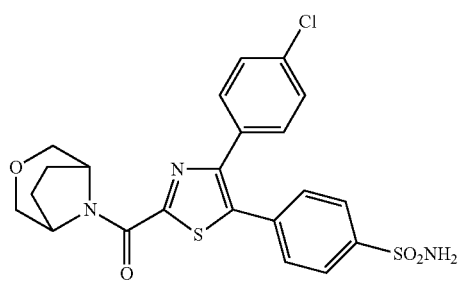 [SMILES: NS(=O)(=O)c1ccc(-c2sc(C(=O)N3C4CCC3COC4)nc2-c2ccc(Cl)cc2)cc1]

To a solution of 3-oxa-8-azabicyclo[13.2.1]octan-8-yl(5-bromo-4-(4-chlorophenyl)thiazol-2-yl)methanone (Step 3 of compound 68, 0.12 g, 0.29 mmol) in a mixture of toluene:ethanol (2 ml: 6 ml) were added 4-aminosulfonylbenzene boronic acid (0.07 g, 0.35 mmol) and potassium carbonate (0.12 g, 0.87 mmol) at 25° C. in a tube, the nitrogen gas was bubbled through reaction mixture for 15 minutes. To the reaction mixture was added tetrakis(triphenylphosphine)palladium(0) (0.017 g, 0.015 mmol) under nitrogen and tube was sealed. The reaction mixture was heated at 90-95° C. for 18 hr with stirring. The progress of reaction was monitored by TLC. The reaction mixture was cooled to 25° C. and filtered through celite. The residue was washed with ethanol (2×20 ml). The filtrate was concentrated under reduced pressure to obtain a crude product; which was purified by column chromatography over silica gel (100-200 mesh) using 40% ethyl acetate in hexanes as an eluent to obtain the title compound (0.08 g, 56.3%). MS: m/z 490 (M+1).

$^1$HNMR (CDCl$_3$, 400 MHz): δ 7.93 (d, J=8.4 Hz, 2H), 7.51 (d, J=8.4 Hz, 2H), 7.38 (d, J=8.4 Hz, 2H), 7.33 (d, J=8.4 Hz, 2H), 5.81 (d, J=5.2 Hz, 1H), 4.96 (bs, exchanges with D$_2$O, 2H), 4.81 (d, J=6.4 Hz, 1H), 3.90 (dd, J=10.8, 8.4 Hz, 2H), 3.77 (t, J=10.8 Hz, 2H), 2.19-2.04 (m, 4H).

The following compounds were prepared according to the procedure described above but with appropriate changes to the reactants.

(cis) 4-(4-(4-chlorophenyl)-2-(2,6-dimethylmorpholine-4-carbonyl)thiazol-5-yl)benzenesulfonamide (Compound 13). MS: m/z 492 (M+1).

$^1$HNMR (DMSO-d$_6$, 400 MHz): δ 7.85 (d, J=8.4 Hz, 2H), 7.59 (d, J=8.4 Hz, 2H), 7.48-7.43 (m, 6H), 5.31 (d, J=13.2 Hz, 1H), 4.36 (d, J=13.2 Hz, 1H), 3.64 (m, 2H), 2.97 (dd. J=13.2, 10.8 Hz, 1H), 2.61 (dd, J=13.2, 10.8 Hz, 1H), 1.17-1.12 (m, 6H).

4-(4-(4-chlorophenyl)-2-(morpholine-4-carbonyl)thiazol-5-yl)benzenesulfonamide (Compound 14). MS: m/z 464 (M+1).

$^1$HNMR (DMSO-d$_6$, 400 MHz): δ 7.84 (d, J=8.4 Hz, 2H), 7.59 (d, J=8.4 Hz, 2H), 7.55-7.46 (m, 6H), 4.45-4.32 (m, 2H), 3.68-3.25 (m, 6H).

4-(4-(4-chlorophenyl)-2-(piperldine-1-carbonyl)thiazol-5-yl)benzenesulfonamide (Compound 18). MS: m/z 462 (M+1).

$^1$HNMR (DMSO-d$_6$, 400 MHz): δ 7.84 (d, J=8.4 Hz, 2H), 7.59 (d, J=8.4 Hz, 2H), 7.50-7.44 (m, 6H), 4.32-4.20 (m, 2H,) 3.72-3.62 (m, 2H), 1.72-1.55 (m, 6H).

4-(2-(3-azabicyclo[3.2.1]octane-3-carbonyl)-4-(4-chlorophenyl)thiazol-5-yl)benzenesulfonamide (Compound 71). MS: m/z 488 (M+1).

$^1$HNMR (DMSO-d$_6$, 400 MHz): δ 7.84 (d, J=8.4, Hz, 2H), 7.59 (d, J=8.4 Hz, 2H), 7.49-7.42 (m, 6H), 4.96 (d, J=12.4 Hz, 1H), 4.25 (d, J=12.4 Hz, 1H), 3.32 (d, J=12.8 Hz, 1H), 2.93 (d, J=12.8 Hz, 1H), 2.28-2.32 (m, 2H), 1.45-1.71 (m, 6H).

Example 3

Preparation of 4-(2-(8-oxa-3-azabicyclo[3.2.1]octane-3-carbonyl)-4-(4-chlorophenyl)thiazol-5-yl)benzenesulfonamide. (Compound 67)

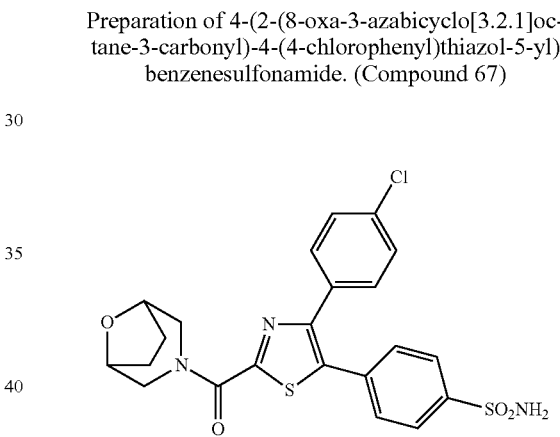

Step 1: 8-oxa-3-azabicyclo[3.2.1]octan-3-yl(4-bromothiazol-2-yl)methanone

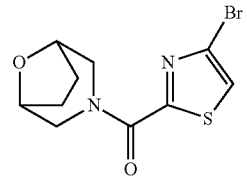 [SMILES: O=C(c1nc(Br)cs1)N1CC2CCC(C1)O2]

To a solution of 4-bromothiazole-2-carboxylic acid (prepared according to the procedure given in WO 2008/57336, 1.00 g, 4.82 mmol) in DMF (15 ml) was added HOST (0.88 g, 5.78 mmol) at room temperature, followed by the addition of (1R,5S)-8-oxa-3-azabicyclo[3.2.1]octane (prepared according to the procedure given in WO 2004/31186, 0.60 gm, 5.30 mmol). The reaction mixture was cooled to 0° C. and to this were added EDC (1.38 g, 7.23 mmol) and triethylamine (1.46 g, 2.02 ml, 14.46 mmol). The reaction mixture was stirred at room temperature for 15 hr and the progress of reaction was monitored by TLC. The reaction mixture was concentrated under reduced pressure. The residue so obtained was taken in ethyl acetate (150 ml) and washed with saturated sodium bicarbonate solution (1×40 ml), brine (1×20 ml) and organic layers separated were dried over anhydrous sodium sulphate, filtered and concentrated under reduced pressure to get a crude product. The crude product was purified by column chromatography over silica gel (100-200 mesh) using 25% ethyl acetate in hexanes as an eluent to obtain the title compound (0.45 g, 30.8%). MS: m/z 304 (M+1).

$^1$HNMR (CDCl$_3$, 400 MHz): δ 7.47 (s, 1H), 5.20 (d, J=13.2 Hz, 1H), 4.49 (d, J=3.6 Hz, 1H), 4.45 (d, J=3.6 Hz, 1H), 4.31 (d, J=13.2 Hz, 1H), 3.55 (dd, J=13.2, 2.0 Hz, 1H), 3.19 (dd, J=13.2, 2.0 Hz, 1H). 2.03-1.82 (m, 4H).

Step 2: 8-oxa-3-azabicyclo[3.2.1]octan-3-yl(4-(4-chlorophenyl)thiazol-2-yl)methanone

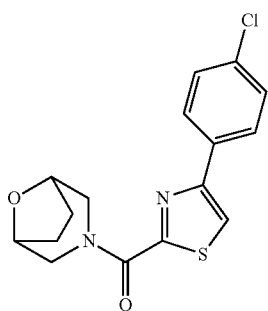 [SMILES: O=C(c1nc(-c2ccc(Cl)cc2)cs1)N1CC2CCC(C1)O2]

To a solution of 8-oxa-3-azabicyclo[3.2.1]octan-3-yl(4-bromothiazol-2-yl)methanone (Step-1 of compound 67, 1.1 g, 3.63 mmol) in a mixture of toluene:ethanol (5 ml:15 ml) were added (4-chlorophenyl) boronic acid (0.85 g, 5.44 mmol) and potassium carbonate (1.25 g, 9.07 mmol) at 25° C. in a tube, the nitrogen gas was bubbled through reaction mixture for 15 minutes. To the reaction mixture was added tetrakis(triphenylphosphine)palladium(0) (0.41 g, 0.36 mmol) under nitrogen and the tube was sealed. The reaction mixture was heated at 90-95° C. for 18 hr with stirring. The progress of reaction was monitored by TLC; the reaction mixture was cooled to 25° C. and filtered through celite. The residue was washed with mixture of 10% methanol in dichloromethane (2×50 ml). The filtrate was concentrated under reduced pressure to obtain a crude product; which was purified by column chromatography over silica gel (100-200 mesh) using 25% ethyl acetate in hexanes as an eluent to obtain the title compound (0.7 g, 57.8%). MS: m/z 335 (M+1).

$^1$HNMR (CDCl$_3$, 400 MHz): δ 7.82 (d, J=8.4 Hz, 2H), 7.69 (s, 1H), 7.42 (d, J=8.4 Hz, 2H), 5.32 (d, J=13.2 Hz, 1H), 4.51 (d, J=3.6 Hz, 1H), 4.48 (d, J=3.6 Hz, 1H), 4.34 (d, J=13.2 Hz, 1H), 3.61 (d. J=13.2. Hz, 1H), 3.23 (d, J=13.2 Hz, 1H), 2.06-1.90 (m, 4H).

Step 3: 4-(2-(8-oxa-3-azabicyclo[3.2.1]octane-3-carbonyl)-4-(4-chlorophenyl)thiazol-5-yl)benzenesulfonamide

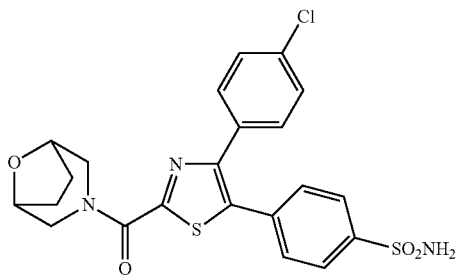 [SMILES: NS(=O)(=O)c1ccc(-c2sc(C(=O)N3CC4CCC(C3)O4)nc2-c2ccc(Cl)cc2)cc1]

To a solution of 8-oxa-3-azabicyclo[3.2.1]octan-3-yl(4-(4-chlorophenyl)thiazol-2-yl)methanone (Step 2 of compound 67, 0.7 g, 2.09 mmol) in dimethyl acetamide (10 ml) were added 4-bromobenzenesulfonamide (0.54 g, 2.30 mmol) and potassium acetate (0.41 g, 4.18 mmol) at 25° C. in a tube, the nitrogen gas was bubbled through reaction mixture for 15 minutes. To this was added palladium (II) acetate (0.047 g, 0.20 mmol) under nitrogen and the tube was sealed. The reaction mixture was heated at 150° C. for 15 hr with stirring. The progress of reaction was monitored by TLC; the reaction mixture was cooled to 25° C. and concentrated under reduced pressure. The residue was dissolved in ethyl acetate (100 ml). The reaction mixture was washed with water (2×30 ml), dried over sodium sulphate and concentrated under reduced pressure to obtain a crude product; which was purified by column chromatography over silica gel (100-200 mesh) using 35% ethyl acetate in hexanes as an eluent to obtain the title compound (0.2 g, 19.5%). MS: m/z 490 (M+1).

$^1$HNMR (DMSO, 400 MHz): δ 7.85 (d. J=8.4 Hz, 2H), 7.59 (d, J=8.4 Hz, 2H), 7.49-7.46 (m, 6H), 5.03 (d, J=13.2 Hz, 1H), 4.42 (d, J=13.2 Hz, 2H), 4.11 (d, J=13.2 Hz, 1H), 3.49 (d, J=13.2, Hz, 1H), 3.10 (d, J=13.2, Hz, 1H). 1.87-1.69 (m, 4H).

The following compounds were prepared according to the procedure described above but with appropriate changes to the reactants.

(trans ±) 4-(4-(4-chlorophenyl)-2-(3,5-dimethylpiperidine-1-carbonyl)thiazol-5-yl)benzenesulfonamide (Compound 19). MS: m/z 490 (M+1).

$^1$HNMR (DMSO-d$_6$, 400 MHz): δ 7.84 (d, J=8.4 Hz, 2H), 7.59 (d, J=8.4 Hz, 2H), 7.49-7.42 (m, 6H), 4.18-4.01 (m, 2H), 3.80-3.72 (m, 2H), 3.38-3.20 (m, 1H), 2.07-1.88 (m, 2H), 1.51-1.40 (m, 2H), 0.94-0.90 (m, 6H).

(cis) 4-(4-(4-chlorophenyl)-2-(3,5-dimethylpiperidine-1-carbonyl)thiazol-5-yl)benzenesulfonamide (Compound 20). MS: m/z 490 (M+1).

$^1$HNMR (DMSO-d$_6$, 400 MHz): δ 8.22 (d, J=8.4 Hz, 2H), 7.97 (d, J=8.4 Hz, 2H), 7.76 (d, J=8.4 Hz, 2H), 7.59 (d. J=8.4 Hz, 2H), 7.54 (bs-exchanges with D$_2$O, 2H). 4.48 (d, J=11.2 Hz, 1H), 3.35-3.31 (m, 3H), 2.33 (t, J=12.0 Hz, 1H), 2.24 (t, J=12.0 Hz, 1H), 1.62-1.51 (m, 2H), 0.89 (d, J=6.0 Hz, 3H), 0.59 (d, J=6.0 Hz, 3H).

(R)-4-(4-(4-chlorophenyl)-2-(3,4-dimethylpiperazine-1-carbonyl)thiazol-5-yl)benzenesulfonamide (Compound 27). MS: m/z 491 (M+1).

$^1$HNMR (DMSO-d$_6$, 400 MHz): δ 7.84 (d, J=8.4 Hz, 2H), 7.60 (d, J=8.4 Hz, 2H), 7.52-7.43 (m, 6H), 5.02-5.18 (m, 1H), 4.32-4.16 (m, 1H), 4.28-4.10 (m, 1H), 2.88-2.68 (m, 2H), 2.30-2.05 (m, 5H), 1.15-1.02 (m, 3H).

(cis) 4-(2-(2,6-dimethylmorpholine-4-carbonyl)-4-(4-(trifluoromethyl)phenyl)thiazol-5-yl)benzenesulfonamide (Compound 28). MS: m/z 526 (M+1).

$^1$HNMR (DMSO-d$_6$, 400 MHz): δ 7.85 (d, J=8.4 Hz, 2H), 7.78 (d, J=8.4 Hz, 2H), 7.66-7.60 (m, 4H), 7.50 (bs-exchanges with D$_2$O, 2H), 5.32 (d, J=13.2 Hz, 1H). 4.37 (d, J=13.2 Hz, 1H), 3.76-3.60 (m, 2H), 2.98 (t, J=13.2 Hz, 1H), 2.66 (t, J=13.2 Hz, 1H), 1.25-1.08 (m, 6H).

(cis) 4-(2-(2,6-dimethylmorpholine-4-carbonyl)-4-(p-tolyl)thiazol-5-yl)benzenesulfonamide (Compound 29). MS: m/z 472 (M+1).

$^1$HNMR (DMSO-d$_6$, 400 MHz): δ 7.83 (d, J=8.4 Hz, 2H), 7.58 (d, J=8.4 Hz, 2H), 7.48 (bs-exchanges with D$_2$O, 2H), 7.32 (d, J=8.0 Hz, 2H), 7.10 (d, J=8.0 Hz, 2H). 5.35 (d, J=13.2 Hz, 1H), 4.37 (d, J=13.2 Hz, 1H), 3.72-3.50 (m, 2H), 2.97 (t, J=13.2 Hz, 1H), 2.61 (t, J=13.2 Hz. 1H), 2.31 (s, 3H). 1.20-1.12 (m, 6H).

(cis) 4-(2-(2,6-dimethylmorpholine-4-carbonyl)-4-(4-fluorophenyl)thiazol-5-yl)benzenesulfonamide (Compound 30). MS: m/z 476 (M+1).

$^1$HNMR (DMSO-d$_6$, 400 MHz): δ 7.84 (d, J=8.4 Hz, 2H), 7.59 (d, J=8.4 Hz, 2H), 7.52-7.46 (m, 4H), 7.25 (t, J=8.8 Hz, 2H), 5.31 (d, J=13.2 Hz, 1H), 4.37 (d, J=13.2 Hz, 1H), 3.72-3.57 (m, 2H), 2.98 (t, J=12.4 Hz, 1H), 2.64 (t, J=12.4 Hz, 1H), 1.22-1.06 (m, 6H).

(cis) 4-(4-(4-(dimethylamino)phenyl)-2-(2,6-dimethylmorpholine-4-carbonyl)thiazol-5-yl)benzenesulfonamide (Compound 31). MS: m/z 501 (M+1).

$^1$HNMR (DMSO-d$_6$, 400 MHz): δ 7.83 (d, J=8.4 Hz, 2H), 7.60 (d, J=8.4 Hz, 2H), 7.48 (bs-exchanges with D$_2$O, 2H), 7.27 (d, J=8.8 Hz, 2H), 6.68 (d, J=8.8 Hz, 2H), 5.40 (d, J=13.2 Hz, 1H), 4.36 (d, J=13.2 Hz, 1H), 3.72-3.56 (m, 2H), 2.97 (t, J=13.2 Hz, 1H), 2.91 (s, 6H), 2.60 (t, J=13.2 Hz, 1H), 1.25-1.03 (m, 6H).

(cis) 4-(2-(2,6-dimethylmorpholine-4-carbonyl)-4-(4-(methylsulfonyl)phenyl)thiazol-5-yl)benzenesulfonamide (Compound 32). MS: m/z 536 (M+1).

$^1$HNMR (DMSO-d$_6$, 400 MHz): δ 7.94 (d, J=8.4 Hz, 2H), 7.86 (d, J=8.4 Hz, 2H), 7.69 (d, J=8.8 Hz, 2H), 7.62 (d, J=8.8 Hz, 2H), 7.50 (bs-exchanges with D$_2$O, 2H), 5.31 (d, J=13.2 Hz, 1H), 4.37 (d, J=13.2 Hz, 1H), 3.72-3.58 (m, 2H), 3.28 (s, 3H), 3.02 (t, J=13.2 Hz, 1H), 2.62 (t; J=13.2 Hz, 1H), 1.71-1.13 (m, 6H).

(cis) 4-(4-(4-cyclopropylphenyl)-2-(2,6-dimethylmorpholine-4-carbonyl)thiazol-5-yl)benzenesulfonamide (Compound 33). MS: m/z 498 (M+1).

$^1$HNMR (DMSO-d$_6$, 400 MHz): δ 7.83 (d, J=8.8 Hz, 2H), 7.58 (d, J=8.8 Hz, 2H), 7.49 (bs-exchanges with D$_2$O, 2H), 7.31 (d, J=8.4 Hz, 2H), 7.08 (d, J=8.4 Hz, 2H), 5.35 (t, J=13.2 Hz, 1H), 4.36 (t, J=13.2 Hz, 1H), 3.76-3.58 (m, 2H), 3.01 (t, J=13.2 Hz, 1H), 2.64 (t, J=13.2 Hz, 1H), 1.98-1.84 (m, 1H), 1.27-1.08 (m, 6H), 0.98-0.92 (m, 2H), 0.73-0.65 (m, 2H).

(cis) 4-(4-(4-cyanophenyl)-2-(2,6-dimethylmorpholine-4-carbonyl)thiazol-5-yl)benzenesulfonamide (Compound 34). MS: m/z 483 (M+1).

$^1$HNMR (DMSO-d$_6$, 400 MHz): δ 7.91-7.83 (m, 4H), 7.63-7.59 (m, 4H), 7.05 (bs-exchanges with D$_2$O, 2H), 5.28 (d, J=12.8 Hz, 1H), 4.37 (d, J=12.8 Hz, 1H), 3.71-3.58 (m, 2H), 2.99 (t, J=12.8 Hz, 1H), 2.61 (t, J=12.8 Hz, 1H), 1.17-1.12 (m, 6H).

(cis) 4-(2-(2,6-dimethylmorpholine-4-carbonyl)-4-(2,6-dimethylpyridin-4-yl)thiazol-5-yl)benzenesulfonamide (Compound 35). MS: m/z 487 (M+1).

$^1$HNMR (DMSO-d$_6$, 400 MHz): δ 7.86 (d, J=8.8 Hz, 2H), 7.62 (d, J=8.8 Hz, 2H), 7.51 (bs-exchanges with D$_2$O, 2H), 7.04 (s, 2H), 5.26 (d, J=13.2 Hz, 1H), 4.36 (d, J=13.2 Hz, 1H), 3.68-3.55 (m, 2H), 2.98 (t, J=13.2 Hz, 1H), 2.65 (t, J=13.2 Hz, 1H), 2.36 (s, 6H), 1.19-1.13 (m, 6H).

(cis) 4-(2-(2,6-dimethylmorpholine-4-carbonyl)-4-(pyridin-4-yl)thiazol-5-yl)benzenesulfonamide (Compound 36). MS: m/z 459 (M+1).

$^1$HNMR (DMSO-d$_6$, 400 MHz): δ 8.59 (d, J=6.0 Hz, 2H), 7.87 (d, J=8.4 Hz, 2H), 7.65 (d, J=8.4 Hz, 2H), 7.52 (bs-exchanges with D$_2$O, 2H), 7.40 (d, J=6.0 Hz, 2H), 5.30 (d, J=13.2 Hz, 1H), 4.37 (d, J=13.2 Hz, 1H), 3.78-3.60 (m, 2H), 2.99 (t, J=13.2 Hz, 1H), 2.62 (t, J=13.2 Hz, 1H), 1.19-1.13 (m, 6H).

(cis) 4-(4-(2,4-difluorophenyl)-2-(2,6-dimethylmorpholine-4-carbonyl)thiazol-5-yl)benzenesulfonamide (Compound 37). MS: m/z 494 (M+1).

$^1$HNMR (DMSO-d$_6$, 400 MHz): δ 7.80 (d, J=8.4 Hz, 2H), 7.65-7.58 (m, 1H), 7.52 (d, J=8.4 Hz, 2H), 7.48 (bs-exchanges with D$_2$O, 2H), 7.37-7.31 (m, 1H), 7.25-7.19 (m, 1H), 5.22 (d, J=13.2 Hz, 1H), 4.02 (d, J=13.2 Hz, 1H), 3.72-3.58 (m, 2H), 2.95 (t, J=13.2 Hz, 1H), 2.60 (t, J=13.2 Hz, 1H), 1.20-1.07 (m, 6H).

(cis) 4-(4-(3,4-difluorophenyl)-2-(2,6-dimethylmorpholine-4-carbonyl)thiazol-5-yl)benzenesulfonamide (Compound 38). MS: m/z 494 (M+1).

$^1$HNMR (DMSO-d$_6$, 400 MHz): δ 7.85 (d, J=8.4 Hz, 2H), 7.60 (d, J=8.4 Hz, 2H), 7.55-7.44 (m, 4H), 7.34-7.20 (m, 1H), 5.28 (d, J=13.2 Hz, 1H), 4.36 (d, J=13.2 Hz, 1H), 3.72-3.55 (m, 2H), 2.94 (t, J=13.2 Hz, 1H), 2.61 (t, J=13.2 Hz, 1H), 1.22-1.07 (m, 6H).

(cis) 4-(4-(4-chloro-3-cyclopropylphenyl)-2-(2,6-dimethylmorpholine-4-carbonyl)thiazol-5-yl)benzenesulfonamide (Compound 39). MS: m/z 532 (M+1).

$^1$HNMR (DMSO-d$_6$, 400 MHz): δ 7.86 (d, J=8.4 Hz, 2H), 7.59 (d, J=8.4 Hz, 2H), 7.50 (bs-exchanges with D$_2$O, 2H), 7.43 (d, J=8.0 Hz, 1H), 7.22 (d, J=8.0 Hz, 1H), 6.99 (s, 1H), 5.36 (d, J=13.2 Hz, 1H), 4.36 (d, J=13.2 Hz, 1H), 3.76-3.58 (m, 2H), 2.97 (t, J=13.2 Hz, 1H), 2.61 (t, J=13.2 Hz, 1H), 2.18-2.05 (m, 1H), 1.24-1.10 (m, 6H), 0.96-0.85 (m, 2H), 0.46-0.35 (m, 2H).

4-(4-(4-chloro-3-methylphenyl)-2-(pyrrolidine-1-carbonyl)thiazol-5-yl)benzenesulfonamide (Compound 40). MS: m/z 462 (M+1).

$^1$HNMR (DMSO-d$_6$, 400 MHz): δ 7.84 (d, J=8.4 Hz, 2H), 7.59 (d, J=8.4 Hz, 2H), 7.52 (s, 1H), 7.48 (bs-exchanges with D$_2$O, 2H), 7.40 (d, J=8.0 Hz, 1H), 7.19 (dd, J=8.0 Hz, 2.0 Hz, 1H), 4.08 (t, J=6.8 Hz, 2H), 3.57 (t, J=13.2 Hz, 2H), 2.23 (s, 3H), 2.02-1.94 (m, 2H), 1.92-1.83 (m, 2H).

(cis) 4-(2-(2,6-dimethylmorpholine-4-carbonyl)-4-(1H-indol-5-yl)thiazol-5-yl)benzenesulfonamide (Compound 41). MS: m/z 497 (M+1).

$^1$HNMR (DMSO-d$_6$, 400 MHz): δ 11.26 (bs-exchanges with D$_2$O, 1H), 7.79 (d, J=8.4 Hz, 2H), 7.66 (s, 1H), 7.57 (d, J=8.4 Hz, 2H), 7.45 (bs-exchanges with D$_2$O, 2H), 7.42-7.35 (m, 2H), 7.12 (dd, J=8.4 Hz, 1.6 Hz, 1H), 6.42 (s, 1H), 5.41 (d, J=13.2 Hz, 1H), 4.38 (d, J=13.2 Hz, 1H), 3.72-3.57 (m, 2H), 2.99 (t, J=13.2 Hz, 1H), 2.64 (t, J=13.2 Hz, 1H), 1.21-1.08 (m, 6H).

(cis) 4-(2-(2,6-dimethylmorpholine-4-carbonyl)-4-(1-methyl-1H-indol-5-yl)thiazol-5-yl)benzenesulfonamide (Compound 42). MS: m/z 511 (M+1).

$^1$HNMR (DMSO-d$_6$, 400 MHz): δ 7.79 (d, J=8.4 Hz, 2H), 7.67 (s, 1H), 7.57 (d, J=8.4 Hz, 2H), 7.50-7.44 (m 3H), 7.37 (d, J=3.2 Hz, 1H), 7.18 (dd, J=8.4 Hz, 1.6 Hz, 1H), 6.43 (d, J=3.2 Hz, 1H), 5.41 (d, J=13.2 Hz, 1H), 4.40 (d, J=13.2 Hz, 1H), 3.79 (s, 3H), 3.72-3.58 (m, 2H), 2.99 (t, J=13.2 Hz, 1H), 2.61 (t, J=13.2 Hz, 1H), 1.21-1.08 (m, 6H).

(cis) 4-(4-(2,3-dihydro-1H-inden-5-yl)-2-(2,6-dimethylmorpholine-4-carbonyl)thiazol-5-yl)benzenesulfonamide (Compound 43). MS: m/z 498 (M+1).

$^1$HNMR (DMSO-$d_6$, 400 MHz): δ 7.82 (d, J=8.4 Hz, 2H), 7.58 (d, J=8.4 Hz, 2H), 7.47 (bs-exchanges with $D_2O$, 2H), 7.35 (s, 1H), 7.20 (d, J=8.0 Hz, 1H), 7.11 (d, J=8.0 Hz, 1H), 5.35 (d, J=12.8 Hz, 1H), 4.37 (d, J=12.8 Hz, 1H), 3.74-3.55 (m, 2H), 3.02 (t, J=13.2 Hz, 1H), 2.88-2.78 (m, 4H), 2.60 (t, J=13.2 Hz, 1H), 2.10-1.92 (m, 2H), 1.22-1.06 (m, 6H).

(cis) 4-(4-(1-acetylindolin-5-yl)-2-(2,6-dimethylmorpholine-4-carbonyl)thiazol-5-yl)benzenesulfonamide (Compound 44). MS: m/z 541 (M+1).

$^1$HNMR (DMSO-$d_6$, 400 MHz): δ 7.94 (d, J=8.0 Hz, 1H), 7.83 (d, J=8.4 Hz, 2H). 7.58 (d, J=8.4 Hz, 2H), 7.47 (bs-exchanges with $D_2O$, 2H), 7.34 (s, 1H), 7.15 (d, J=8.0 Hz, 1H), 5.32 (d, J=12.8 Hz, 1H), 4.36 (d, J=12.8 Hz, 1H), 4.18-4.08 (m. 2H), 3.76-3.60 (m, 2H), 3.22-3.10 (m, 2H), 3.00-2.91 (m, 1H), 2.66-2.50 (m, 1H), 2.15 (s, 3H), 1.25-1.10 (m, 6H).

(cis) 4-(4-(4-chlorophenyl)-2-(2,6-dimethylmorpholine-4-carbonyl)thiazol-5-yl)-2-methylbenzenesulfonamide (Compound 46). MS: m/z 506 (M+1).

$^1$HNMR (DMSO-$d_6$, 400 MHz): δ 7.83 (d, J=8.4 Hz, 1H), 7.51 (bs-exchanges with $D_2O$, 2H), 7.50-7.44 (m, 5H), 7.33 (dd, J=8.0 Hz, 1.6 Hz, 1H), 5.31 (d, J=12.8 Hz, 1H), 4.36 (d, J=13.2 Hz, 1H), 3.78-3.56 (m, 2H), 2.97 (t, J=12.8 Hz, 1H), 2.70-2.55 (m, 4H), 1.21-1.10 (m, 6H).

(cis) 4-(4-(4-chlorophenyl)-2-(2,6-dimethylmorpholine-4-carbonyl)thiazol-5-yl)-3-fluorobenzenesulfonamide (Compound 47). MS: m/z 510 (M+1).

$^1$HNMR (DMSO-$d_6$, 400 MHz): δ 7.76-7.63 (m, 4H), 7.50-7.36 (m, 5H), 5.31 (d, J=12.8 Hz, 1H), 4.37 (d, J=12.8 Hz, 1H), 3.76-3.56 (m, 2H), 2.99 (t, J=12.8 Hz, 1H), 2.61 (t, J=12.8 Hz, 1H), 1.25-0.81 (m, 6H).

(cis) 4-(4-(4-chlorophenyl)-2-(2,6-dimethylmorpholine-4-carbonyl)thiazol-5-yl)-2-fluorobenzenesulfonamide (Compound 48). MS: m/z 510 (M+1).

$^1$HNMR (DMSO-$d_6$, 400 MHz): δ 7.90-7.68 (m, 1H), 7.55-7.42 (m, 7H), 7.36 (d, J=7.6 Hz, 1H), 5.29 (d, J=12.8 Hz, 1H), 4.37 (d, J=12.8 Hz, 1H), 3.72-3.60 (m, 2H), 2.89 (t, J=12.8 Hz, 1H), 2.61 (t, J=12.8 Hz, 1H), 1.28-1.02 (m, 6H).

(cis) 4-(4-(4-chlorophenyl)-2-(2,6-dimethylmorpholine-4-carbonyl)thiazol-5-yl)-2-(trifluoromethyl)benzenesulfonamide (Compound 49). MS: m/z 560 (M+1).

$^1$HNMR (DMSO-$d_6$, 400 MHz): δ 8.17 (d, J=8.0 Hz, 1H), 7.92 (d, J=8.0 Hz, 1H), 7.88-7.82 (m, 3H), 7.52-7.41 (m, 4H), 5.27 (d, J=13.2 Hz, 1H), 4.37 (d, J=13.2 Hz, 1H), 3.71-3.60 (m, 2H), 3.01-2.95 (m, 1H), 2.68-2.60 (m, 1H), 1.24-1.02 (m, 6H).

(cis) 4-(4-(4-chloro-3-cyclopropylphenyl)-2-(2,6-dimethylmorpholine-4-carbonyl)thiazol-5-yl)-2-methylbenzenesulfonamide (Compound 54). MS: m/z 546 (M+1).

$^1$HNMR (DMSO-$d_6$, 400 MHz): δ 7.86 (d, J=8.0 Hz, 1H), 7.52 (bs-exchanges with $D_2O$, 2H), 7.47-7.42 (m, 2H), 7.36 (dd, J=8.0 Hz, 2.0 Hz, 1H), 7.25 (dd, J=8.4 Hz, 2.4 Hz, 1H), 7.01 (d, J=2.4 Hz, 1H), 5.36 (d, J=13.2 Hz, 1H), 4.36 (d, J=13.2 Hz, 1H), 3.78-3.60 (m, 2H), 3.05-2.90 (m, 1H), 2.62-2.54 (m, 4H), 2.15-2.06 (m, 1H), 1.23-1.12 (m, 6H), 1.00-0.88 (m, 2H), 0.45-0.36 (m, 2H).

4-(2-(6-oxa-3-azabicyclo[3.1.1]heptane-3-carbonyl)-4-(4-chlorophenyl)thiazol-5-yl)benzenesulfonamide (Compound 69). MS: m/z 476 (M+1).

$^1$HNMR (DMSO-$d_6$, 400 MHz): δ 7.85 (d, J=8.4 Hz, 2H), 7.61 (d, J=8.4 Hz, 2H), 7.51-7.44 (m, 6H), 4.68-4.61 (m, 311), 4.24 (d, J=12.0 Hz, 1H), 3.90 (d, J=12.0 Hz, 1H), 3.69 (d, J=12.0 Hz, 1H), 3.12 (d, J=8.8 Hz, 1H), 1.90 (d, J=8.8, Hz, 1H).

4-(2-(8-azabicyclo[3.2.1]octane-8-carbonyl)-4-(4-chlorophenyl)thiazol-5-yl)benzenesulfonamide (Compound 70). MS: m/z 488 (M+1).

$^1$HNMR (DMSO-$d_6$, 400 MHz): δ 7.84 (d, J=8.4, Hz, 2H), 7.61 (d, J=8.4 Hz, 2H), 7.49-7.45 (m, 6H), 5.60 (d, J=6.4 Hz, 1H), 4.65 (d, J=6.4 Hz, 1H), 2.06-1.56 (m, 10H).

(cis) 4-(4-(4-chlorophenyl)-2-(1,5-dimethyl-3-azabicyclo[3.1.0]hexane-3-carbonyl)thiazol-5-yl)benzenesulfonamide (Compound 72). MS: m/z 488 (M+1).

$^1$HNMR (DMSO-$d_6$, 400 MHz): δ 7.84 (d, J=8.4, Hz, 2H), 7.58 (d, J=8.4 Hz, 2H). 7.49-7.44 (m, 6H), 4.62 (d, J=12.0, Hz, 1H), 3.95 (d, J=12.0, Hz, 1H), 3.72 (d, J=12.0, Hz, 1H), 3.38 (d, J=12.0 Hz, 1H), 1.20 (s, 6H), 0.43 (d, J=4.4 Hz, 1H), 0.38 (d, J=4.4 Hz, 1H).

4-(2-(3-azabicyclo[3.1.0]hexane-3-carbonyl)-4-(4-chlorophenyl)thiazol-5-yl)benzenesulfonamide (Compound 73). MS: m/z 459 (M+1).

$^1$HNMR (DMSO-$d_6$, 400 MHz): δ 7.85 (d, J=8.4, Hz, 2H), 7.60 (d, J=8.4 Hz, 2H), 7.52-7.44 (m, 6H), 4.56 (d, J=12.0, Hz, 1H), 3.98 (dd, J=12.0, 4.4 Hz, 1H), 3.86 (d, J=12.0, Hz, 1H), 3.58 (dd, J=12.0, 4.4 Hz, 1H), 1.75-1.72 (m, 1H), 1.63-1.61 (m, 1H), 0.77-0.74 (m, 1H), 0.19-0.15 (m, 1H).

4-(4-(4-chlorophenyl)-2-(1,2,3,4-tetrahydroquinoline-1-carbonyl)thiazol-5-yl)benzenesulfonamide (Compound 74). MS: m/z 510 (M+1).

$^1$HNMR (DMSO-$d_6$, 400 MHz): δ 7.85 (d, J=8.4, Hz, 2H), 7.59 (d, J=8.4, Hz, 2H), 7.49-7.34 (m, 5H), 7.34-7.23 (m, 3H), 7.17-7.14 (m, 2H), 4.23-4.21 (m, 2H), 2.82 (t, J=6.4 Hz, 2H), 2.01 (q, J=6.4 Hz, 2H).

4-(4-(4-chlorophenyl)-2-(1,2,3,4-tetrahydroisoquinoline-2-carbonyl)thiazol-5-yl)benzenesulfonamide (Compound 75). MS: m/z 510 (M+1).

$^1$HNMR (DMSO-$d_6$, 400 MHz): δ 7.85 (d, J=8.4, Hz, 2H), 7.61 (d, J=8.4, Hz, 2H), 7.45-7.54 (m, 6H), 7.26-7.20 (m, 4H), 5.75 (s, 2H), 4.49 (t, J=5.6 Hz, 1H), 3.90 (t, J=5.6 Hz, 1H), 2.98-2.93 (m, 2H).

4-(4-(4-chlorophenyl)-2-(6-azaspiro[2.5]octane-6-carbonyl)thiazol-5-yl)benzenesulfonamide (Compound 76). MS: m/z 488 (M+1).

$^1$HNMR (DMSO-$d_6$, 400 MHz): δ 7.85 (d, J=8.4, Hz, 2H), 7.61 (d, J=8.4, Hz, 2H), 7.49-7.43 (m, 6H), 4.33-4.29 (m, 2H), 3.73-3.69 (m, 2H), 1.46-1.42 (m, 4H), 0.39 (s, 4H).

4-(4-(4-chlorophenyl)-2-(5-azaspiro[2.5]octane-5-carbonyl)thiazol-5-yl)benzenesulfonamide (Compound 77). MS: m/z 488 (M+1).

$^1$HNMR (DMSO-$d_6$, 400 MHz): δ 7.84 (d, J=8.0, Hz, 2H), 7.59 (d, J=8.0, Hz, 2H), 7.49-7.44 (m, 4H), 7.39 (d, J=8.0 Hz, 2H), 4.32-4.30 (m, 1H), 4.10 (s, 1H), 3.73-3.68 (m, 1H), 3.47 (s, 1H), 1.72-1.52 (m, 4H), 0.52-0.47 (m, 2H), 0.33 (s, 2H).

4-(2-(3-azabicyclo[3.1.1]heptane-3-carbonyl)-4-(4-chlorophenyl)thiazol-5-yl)benzenesulfonamide (Compound 78). MS: m/z 474 (M+1).

$^1$HNMR (DMSO-$d_6$, 400 MHz): δ 7.84 (d, J=8.0, Hz, 2H), 7.60 (d, J=8.0, Hz, 2H), 7.49-7.43 (m, 6H), 4.39 (s, 2H), 3.78 (s, 2H), 2.55-2.51 (m, 2H), 2.17-2.15 (m, 2H), 1.43-1.40 (m, 2H).

4-(4-(4-chlorophenyl)-2-(4-azaspiro[2.4]heptane-4-carbonyl)thiazol-5-yl)benzenesulfonamide (Compound 79). MS: m/z 474 (M+1).

$^1$HNMR (DMSO-$d_6$, 400 MHz): δ 7.84 (d, J=8.0, Hz, 2H), 7.58 (d, J=8.0, Hz, 2H), 7.49-7.43 (m, 6H), 4.36 (t, J=4.8 Hz, 2H), 1.99-1.91 (m, 6H), 0.62 (t, J=4.8 Hz, 2H).

4-(2-(3-azabicyclo[3.1.0]hexane-3-carbonyl)-4-(4-chloro-3-methylphenyl)thiazol-5-yl)benzenesulfonamide (Compound 80). MS: m/z 474 (M+1).

$^1$HNMR (DMSO-$d_6$, 400 MHz): δ 7.83 (d, J=8.4, Hz, 2H), 7.58 (d, J=8.4 Hz, 2H), 7.53 (d, J=1.6 Hz, 1H), 7.48 (bs-exchanges with D₂O, 2H), 7.39 (d, J=8.4 Hz, 1H), 7.18 (dd, J=8.4, 1.6 Hz, 1H), 4.54 (d, J=12.0, Hz, 1H), 3.96 (dd, J=12.0, 4.0 Hz, 1H), 3.86 (d, J=12.0, Hz, 1H), 3.57 (dd, J=12.0, 4.0 Hz, 1H), 2.31 (s, 3H), 1.75-1.72 (m. 1H), 1.64-1.61 (m, 1H), 0.77-0.74 (m, 1H), 0.19-0.15 (m, 1H).

4-(2-(3-azabicyclo[3.1.0]hexane-3-carbonyl)-5-(4-sulfamoylphenyl)thiazol-4-yl)benzamide (Compound 81). MS: m/z 469 (M+1).

¹HNMR (DMSO-d₆, 400 MHz): δ 8.01 (bs-exchanges with D₂O, 2H), 7.86-7.83 (m, 4H), 7.60 (d, J=8.4, Hz, 2H), 7.54 (d, J=8.4 Hz, 2H), 7.48 (bs-exchanges with D₂O, 2H), 4.57 (d, J=12.0, Hz, 1H), 3.98 (dd, J=12.0, 4.4 Hz, 1H), 3.87 (d, J=12.0, Hz, 1H), 3.59 (dd, J=12.0, 4.4 Hz, 1H), 1.75-1.72 (m, 1H), 1.63-1.61 (m, 1H), 0.77-0.74 (m, 1H), 0.19-0.15 (m, 1H).

N-(4-(2-(3-azabicyclo[3.1.0]hexane-3-carbonyl)-5-(4-sulfamoylphenyl)thiazol-4-yl)phenyl)acetamide (Compound 82). MS: m/z 483 (M+1).

¹HNMR (DMSO-d₆, 400 MHz): δ 10.05 (bs-exchanges with D₂O, 1H), 7.84-7.79 (m, 3H), 7.66 (d, J=8.0, Hz, 1H), 7.58 (d, J=8.4 Hz, 2H), 7.46 (bs-exchanges with D₂O, 2H), 7.24 (t, J=8.0 Hz, 1H), 6.93 (d, J=8.0 Hz, 1H), 4.57 (d, J=12.0, Hz, 1H), 3.95 (dd, J=12.0, 4.4 Hz, 1H), 3.85 (d, J=12.0. Hz, 1H), 3.58 (dd, J=12.0, 4.4 Hz, 1H), 1.75-1.72 (m, 1H), 1.63-1.61 (m, 1H), 0.77-0.74 (m, 1H), 0.19-0.15 (m, 1H).

4-(2-(3-azabicyclo[3.1.0]hexane-3-carbonyl)-5-(4-sulfamoylphenyl)thiazol-4-yl)-N,N-dimethylbenzamide (Compound 83). MS: m/z 497 (M+1).

¹HNMR (DMSO-d₆, 400 MHz): δ 7.85 (d, J=8.4, Hz, 2H), 7.61 (d, J=8.4 Hz, 2H), 7.53 (d, J=8.4 Hz, 2H), 7.48 (bs-exchanges with D₂O, 2H), 7.41 (d, J=8.4 Hz, 2H), 4.57 (d, J=12.0, Hz, 1H), 4.00 (dd, J=12.0, 4.4 Hz, 1H), 3.85 (d, J=12.0, Hz, 1H), 3.58 (dd, J=12.0, 4.4 Hz, 1H), 2.97 (s, 3H), 2.91 (s, 3H), 1.77-1.74 (m, 1H), 1.63-1.61 (m, 1H), 0.77-0.74 (m, 1H), 0.19-0.15 (m, 1H).

4-(2-(3-azabicyclo[3.1.0]hexane-3-carbonyl)-4-(2,4-difluorophenyl)thiazol-5-yl)benzenesulfonamide (Compound 84). MS: m/z 462 (M+1).

¹HNMR (DMSO-d₆, 400 MHz): δ 7.79 (d, J=8.4, Hz, 2H), 7.70-7.64 (m, 1H), 7.51 (d, J=8.4 Hz, 2H), 7.47 (bs-exchanges with D₂O, 2H), 7.35-7.21 (m, 2H), 4.48 (d, J=12.0, Hz, 1H), 3.93-3.85 (m, 2H), 3.58 (dd, J=12.0, 4.4 Hz, 1H), 1.75-1.69 (m, 1H), 1.64-1.60 (m, 1H), 0.76-0.71 (m, 1H), 0.18-0.14 (m, 1H).

4-(2-(3-azabicyclo[3.1.0]hexane-3-carbonyl)-4-(4-(trifluoromethyl)phenyl)thiazol-5-yl)benzenesulfonamide (Compound 85). MS: m/z 494 (M+1).

¹HNMR (DMSO-d₆, 400 MHz): δ 7.85 (d, J=8.4, Hz, 2H), 7.78 (d, J=8.4 Hz, 2H), 7.68 (d, J=8.4 Hz, 2H), 7.62 (d, J=8.4 Hz, 2H), 7.50 (bs-exchanges with D₂O, 2H), 4.57 (d, J=12.0, Hz, 1H), 4.01 (dd, J=12.0, 4.4 Hz, 1H), 3.85 (d, J=12.0, Hz, 1H), 3.58 (dd, J=12.0, 4.4 Hz, 1H), 1.77-1.74 (m, 1H), 1.65-1.61 (m, 1H), 0.77-0.74 (m, 1H), 0.18-0.14 (m, 1H).

4-(2-(3-azabicyclo[3.1.0]hexane-3-carbonyl)-4-(4-cyclopropylphenyl)thiazol-5-yl)benzenesulfonamide (Compound 86). MS: m/z 465 (M+1).

¹HNMR (DMSO-de, 400 MHz): δ 7.83 (d, J=8.0, Hz, 2H), 7.58 (d, J=8.0 Hz, 2H), 7.47 (bs-exchanges with D₂O, 2H), 7.34 (d, J=8.0 Hz, 2H), 7.08 (d, J=8.0 Hz, 2H), 4.55 (d, J=12.0, Hz, 1H), 3.96 (d, J=10.0 Hz, 1H), 3.86 (d, J=12.0, Hz, 1H), 3.57 (d, J=10.0 Hz, 1H), 1.92-1.85 (m, 1H), 1.77-1.74 (m, 1H), 1.65-1.61 (m, 1H), 0.97-0.93 (m, 2H), 0.77-0.74 (m, 3H), 0.18-0.14 (m, 1H).

4-(2-(3-azabicyclo[3.1.0]hexane-3-carbonyl)-4-(6-(trifluoromethyl)pyridin-3-yl)thiazol-5-yl)benzenesulfonamide (Compound 87). MS: m/z 495 (M+1).

¹HNMR (DMSO-d₆, 400 MHz): δ 8.81 (d, J=1.6 Hz, 1H), 8.16 (dd, J=8.4, 1.6 Hz, 1H), 7.96 (d, J=8.4 Hz, 1H), 7.88 (d, J=8.4 Hz, 2H), 7.66 (d, J=8.4 Hz, 2H), 7.50 (bs-exchanges with D₂O, 2H), 4.56 (d, J=12.0 Hz, 1H), 4.01 (dd, J=12.0, 4.4 Hz, 1H), 3.87 (d, J=12.0 Hz, 1H), 3.59 (dd, J=12.0, 4.4 Hz, 1H), 1.77-1.72 (m, 1H), 1.65-1.61 (m, 1H), 0.76-0.72 (m, 1H), 0.18-0.14 (m, 1H).

4-(2-(3-azabicyclo[3.1.0]hexane-3-carbonyl)-4-(quinolin-8-yl)thiazol-5-yl)benzenesulfonamide (Compound 88). MS: m/z 477 (M+1).

¹HNMR (DMSO-d₆, 400 MHz): δ 8.72-8.70 (m, 1H), 8.42 (dd, J=8.4 Hz, J=2.0 Hz, 1H), 8.11 (dd, J=8.4 Hz, J=2.0 Hz, 1H), 7.84-7.38 (m, 1H), 7.71-7.67 (m, 1H). 7.58-7.56 (m, 2H), 7.53-7.50 (m, 1H), 7.42-7.29 (m, 4H), 4.44 (d, J=12.0 Hz, 1H), 3.89 (d, J=12.0 Hz, 1H), 3.85-3.78 (m, 1H), 3.59-3.54 (m, 1H), 1.65-1.57 (m, 2H), 0.76-0.68 (m, 1H), 0.18-0.14 (m, 1H).

4-(4-(1-acetylindolin-5-yl)-2-(3-azabicyclo[3.1.0]hexane-3-carbonyl)thiazol-5-yl)benzenesulfonamide (Compound 91). MS: m/z 508 (M+1).

¹HNMR (DMSO-d₆, 400 MHz): δ 7.93 (d, J=8.4 Hz, 1H), 7.82 (d, J=8.4 Hz, 2H), 7.57 (d, J=8.4 Hz, 2H), 7.46 (bs-exchanges with D₂O, 2H), 7.41 (s, 1H), 7.13 (d, J=8.4 Hz, 1H), 4.57 (d, J=12.0, Hz, 1H), 4.12 (t, J=8.4, Hz, 2H), 3.97 (dd, J=12.0, 4.4 Hz, 1H), 3.85 (d, J=12.0, Hz, 1H), 3.58 (dd, J=12.0, 4.4 Hz, 1H), 3.13 (t, J=8.4, Hz, 2H), 2.16 (s, 3H), 1.77-1.74 (m, 1H), 1.65-1.61 (m, 1H), 0.77-0.74 (m, 1H), 0.18-0.14 (m, 1H).

3-azabicyclo[3.1.0]hexan-3-yl(4-(4-chlorophenyl)-5-(4-(piperidin-1-ylsulfonyl)phenyl)thiazol-2-yl)methanone (Compound 93). MS: m/z 528 (M+1).

¹HNMR (DMSO-d₆, 400 MHz): δ 7.76 (d, J=8.4 Hz, 2H), 7.64 (d, J=8.4 Hz, 2H), 7.46-7.41 (m, 4H), 4.57 (d, J=12.0, Hz, 1H), 3.97 (dd, J=12.0, 4.0 Hz, 1H), 3.86 (d, J=12.0, Hz, 1H), 3.59 (dd, J=12.0, 4.4 Hz, 1H), 2.94-2.91 (m, 4H), 1.77-1.74 (m, 1H), 1.65-1.61 (m, 1H), 1.55-1.51 (m, 4H), 1.39-1.37 (m, 2H), 0.77-0.74 (m, 1H), 0.18-0.14 (m, 1H).

4-(2-(3-azabicyclo[3.1.0]hexane-3-carbonyl)-4-(4-chlorophenyl)thiazol-5-yl)-2-methylbenzenesulfonamide (Compound 94). MS: m/z 474 (M+1).

¹HNMR (DMSO-d₆, 400 MHz): δ 7.83 (d, J=8.0 Hz, 1H), 7.53-7.43 (m, 7H), 7.33 (dd, J=8.0, 1.6 Hz, 1H), 4.55 (d, J=12.0 Hz, 1H), 4.00 (dd, J=12.0, 4.4 Hz, 1H), 3.87 (d, J=12.0, Hz, 1H), 3.58 (dd, J=12.0, 4.4 Hz, 1H), 1.77-1.74 (m, 1H), 1.65-1.61 (m, 1H), 0.77-0.74 (m, 1H), 0.18-0.14 (m, 1H).

4-(2-(3-azabicyclo[3.1.0]hexane-3-carbonyl)-4-(4-chlorophenyl)thiazol-5-yl)-2-(trifluoromethyl)benzenesulfonamide (Compound 96). MS: m/z 528 (M+1).

¹HNMR (DMSO-d₆, 400 MHz): δ 8.17 (d, J=8.4 Hz, 1H), 7.92 (d, J=8.4 Hz, 1H), 7.85-7.82 (m, 3H), 7.49-7.46 (m, 4H), 4.55 (d, J=12.0, Hz, 1H), 4.02 (dd, J=12.0, 4.0 Hz, 1H), 3.95 (d, J=12.0, Hz, 1H). 3.60 (dd, J=12.0, 4.0 Hz, 1H), 1.77-1.74 (m, 1H), 1.65-1.61 (m, 1H), 0.77-0.74 (m, 1H), 0.18-0.14 (m, 1H).

4-(2-(3-azabicyclo[3.1.0]hexane-3-carbonyl)-4-(4-chlorophenyl)thiazol-5-yl)-3-methylbenzenesulfonamide (Compound 97). MS: m/z 474 (M+1).

¹HNMR (DMSO-d₆, 400 MHz): δ 7.79 (s, 1H), 7.72 (d, J=8.0, Hz, 1H), 7.57 (d, J=8.0, Hz, 1H), 7.46 (bs-exchanges with D₂O, 2H), 7.42-7.38 (m, 4H), 4.61 (d, J=12.0 Hz, 1H), 4.02 (dd, J=12.0, 4.4 Hz, 1H), 3.87 (d, J=12.0 Hz, 1H), 3.60 (dd, J=12.0, 4.4 Hz, 1H), 1.99 (s, 3H), 1.77-1.74 (m, 1H), 1.65-1.61 (m, 1H), 0.77-0.74 (m, 1H), 0.21-0.18 (m, 1H).

4-(2-(3-azabicyclo[3.1.0]hexane-3-carbonyl)-4-(4-chlorophenyl)thiazol-5-yl)-3-fluorobenzenesulfonamide (Compound 98). MS: m/z 478 (M+1).

¹HNMR (DMSO-d₆, 400 MHz): δ 7.73-7.70 (m, 3H), 7.63 (bs-exchanges with D₂O, 2H), 7.54-7.44 (m, 4H), 4.57 (d, J=12.0, Hz, 1H), 3.99 (dd, J=12.0, 4.4 Hz, 1H), 3.86 (d, J=12.0, Hz, 1H), 3.59 (dd, J=12.0, 4.4 Hz, 1H), 1.77-1.74 (m, 1H), 1.65-1.61 (m, 1H), 0.77-0.74 (m, 1H), 0.19-0.15 (m, 1H).

4-(2-(3-azabicyclo[3.1.0]hexane-3-carbonyl)-4-(4-chlorophenyl)thiazol-5-yl)-2-fluorobenzenesulfonamide (Compound 99). MS: m/z 478 (M+1).

¹HNMR (DMSO-d₆, 400 MHz): δ 7.82-7.78 (m, 3H), 7.54-7.47 (m, 5H), 7.37 (dd, J=8.0, 1.6 Hz, 1H), 4.55 (d, J=12.0 Hz, 1H), 3.97 (dd, J=12.0, 4.4 Hz, 1H), 3.86 (d, J=12.0 Hz, 1H), 3.57 (dd, J=12.0, 4.4 Hz, 1H), 1.77-1.74 (m, 1H), 1.65-1.61 (m, 1H), 0.77-0.74 (m, 1H), 0.19-0.15 (m, 1H).

4-(2-(3-azabicyclo[3.1.0]hexane-3-carbonyl)-4-(4-chlorophenyl)thiazol-5-yl)-5,6,7,8-tetrahydronaphthalene-1-sulfonamide (Compound 100). MS: m/z 514 (M+1).

¹HNMR (DMSO-d₆, 400 MHz): δ 7.81 (d, J=8.0 Hz, 1H), 7.54 (bs-exchanges with D₂O, 2H), 7.43-7.40 (m, 4H), 7.37 (d, J=8.0 Hz, 1H), 4.60 (d, J=12.0 Hz, 1H), 4.01 (dd, J=12.0, 4.4 Hz, 1H), 3.87 (d, J=12.0 Hz, 1H), 3.57 (dd, J=12.0, 4.4 Hz, 1H), 3.16-3.13 (m, 2H), 2.38-2.36 (m, 2H), 1.77-1.57 (m, 6H), 0.77-0.74 (m, 1H), 0.19-0.15 (m, 1H).

4-(2-(3-azabicyclo[3.1.0]hexane-3-carbonyl)-4-(4-chloro-3-methylphenyl)thiazol-5-yl)-2-fluorobenzenesulfonamide (Compound 101). MS: m/z 492 (M+1).

¹HNMR (DMSO-d₆, 400 MHz): δ 7.79-7.75 (m, 3H), 7.56-7.51 (m, 2H), 7.43 (d, J=8.4 Hz, 1H), 7.34 (d, J=8.4 Hz, 1H), 7.21 (d, J=8.4 Hz, 1H), 4.53 (d, J=12.0 Hz, 1H), 3.95 (d, J=8.8 Hz, 1H), 3.86 (d, J=12.0 Hz, 1H), 3.58 (d, J=8.8 Hz, 1H), 2.31 (s, 3H), 1.77-1.74 (m, 1H), 1.64-1.61 (m, 1H), 0.77-0.74 (m, 1H), 0.18-0.14 (m, 1H).

Example 4

4-(2-(3-azabicyclo[3.1.0]hexane-3-carbonyl)-4-(4-chlorophenyl)thiazol-5-yl)-N,N-dimethylbenzenesulfonamide (Compound 92)

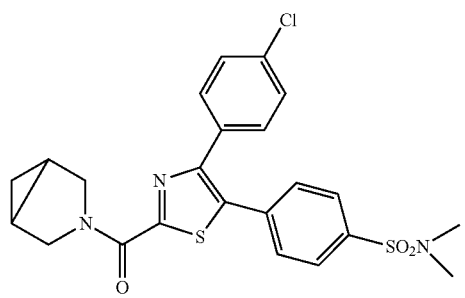

Step 1: 4-(2-(3-azabicyclo[3.1.0]hexane-3-carbonyl)-4-(4-chlorophenyl)thiazol-5-yl)-N,N-dimethylbenzenesulfonamide

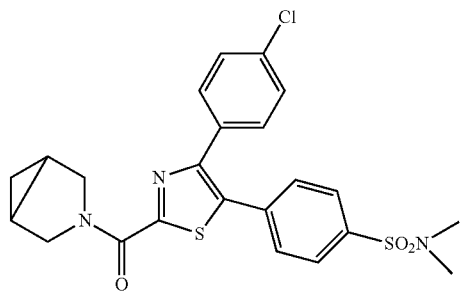

Potassium carbonate (0.19 g, 1.35 mmol) was added to stirred solution of 4-(2-(3-azabicyclo[3.1.0]hexane-3-carbonyl)-4-(4-chlorophenyl)thiazol-5-yl)benzenesulfonamide (Compound 73, 0.4 g, 0.87 mmol) in DMF (5 ml) at room temperature. The reaction mixture was stirred at room temperature for 15 min and then added methyl iodide (0.26 g, 0.11 ml, 1.83 mmol) and stirred at room temperature for 16 hr. The progress of reaction was monitored by TLC. The reaction mixture was diluted with water (25 ml) and extracted with ethyl acetate (2×25 ml). The combined organic layer was dried over sodium sulphate and concentrated under reduced pressure to obtain a crude product; which was purified by flash column chromatography using 25% ethyl acetate in hexanes as an eluent to obtain the title compound (0.08 g, 18.8%). MS: m/z 487 (M+1).

¹HNMR (DMSO-d₆, 400 MHz): δ 7.79 (d, J=8.4 Hz, 2H), 7.65 (d, J=8.4 Hz, 2H), 7.49-7.43 (m, 4H), 4.55 (d, J=12.0 Hz, 1H), 3.98 (dd, J=12.0, 4.4 Hz, 1H), 3.87 (d, J=12.0 Hz, 1H), 3.58 (dd, J=12.0, 4.4 Hz, 1H), 2.64 (s, 6H), 1.77-1.74 (m, 1H), 1.65-1.61 (m, 1H), 0.77-0.74 (m, 1H), 0.18-0.14 (m, 1H).

Example 5

N-((4-(2-(3-azabicyclo[3.1.0]hexane-3-carbonyl)-4-(4-chlorophenyl)thiazol-5-yl)phenyl)sulfonyl)acetamide (Compound 95)

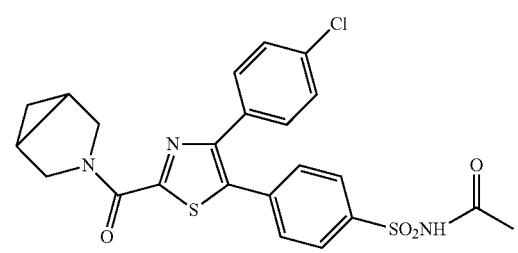

Step 1: N-((4-(2-(3-azabicyclo[3.1.0]hexane-3-carbonyl)-4-(4-chlorophenyl)thiazol-5-yl)phenyl)sulfonyl)acetamide

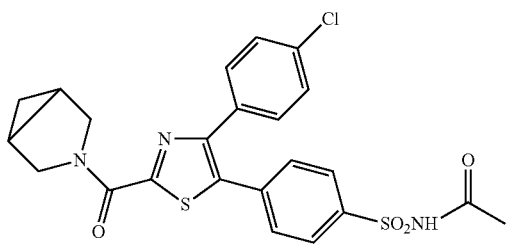

lp;1pAcetic anhydride (0.66 g, 0.65 mmol) was added to stirred solution of 44243-azabicyclo[3.1.0]hexane-3-carbonyl)-4-(4-chlorophenyl)thiazol-5-yl)benzenesulfonamide (Compound 73, 0.3 g, 0.65 mmol) in pyridine (5 ml) at 0° C. The reaction mixture was stirred at room temperature for 2 hr. The progress of reaction was monitored by TLC. The reaction mixture was diluted with water (25 ml) and extracted with ethyl acetate (2×25 ml). The combined organic layer was dried over sodium sulphate and concentrated under reduced pressure to obtain a crude product; which was purified by flash column chromatography using 25% ethyl acetate in hexanes as an eluent to obtain the title compound (0.07 g, 21.4%). MS: m/z 502 (M+1).

$^1$HNMR (DMSO-$d_6$, 400 MHz): δ 7.86 (d. J=8.0 Hz, 2H), 7.54 (d, J=8.0 Hz, 2H), 7.49-7.43 (m, 4H), 4.56 (d, J=12.0, Hz, 1H), 3.96 (dd, J=12.0, 4.4 Hz, 1H), 3.87 (d, J=12.0, Hz, 1H), 3.58 (dd, J=12.0, 4.4 Hz, 1H), 3.48 (bs-exchanges with D$_2$O, 1H), 1.91 (s, 3H), 1.77-1.74 (m, 1H), 1.65-1.61 (m, 1H), 0.77-0.74 (m, 1H), 0.18-0.14 (m, 1H).

Example 6

(cis) 4-(4-(4-chloroindolin-1-yl)-2-(2,6-dimethylmorpholine-4-carbonyl)thiazol-5-yl)benzenesulfonamide (Compound 45)

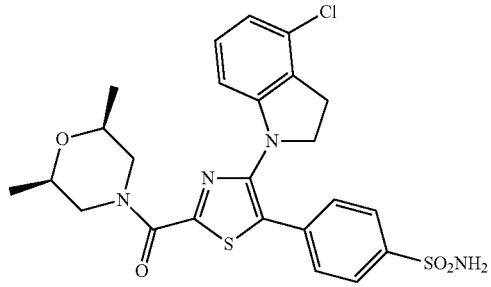 [SMILES: C[C@@H]1CN(C(=O)c2nc(N3CCc4c(Cl)cccc43)c(-c3ccc(S(N)(=O)=O)cc3)s2)C[C@H](C)O1]

Step 1: (cis) (4-bromothiazol-2-yl) (2,6-dimethylmorpholino)methanone

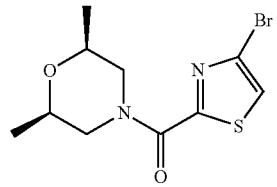 [SMILES: C[C@@H]1CN(C(=O)c2nc(Br)cs2)C[C@H](C)O1]

To a solution of 4-bromothiazole-2-carboxylic acid (prepared according to the procedure given in WO200857336, 1.35 g, 6.49 mmol) in DMF (15 ml) was added HOBT (1.09 g, 7.14 mmol) at room temperature followed by the addition of (2S,6R)-2,6-dimethylmorpholine (0.75 g, 0.8 ml, 6.49 mmol). The reaction mixture was cooled to 0° C. and to this were added EDC (1.86 gm., 9.73 mmol) and triethylamine (2.63 g, 3.62 ml, 26.00 mmol). Mixture was stirred at room temperature for 15 hr. The progress of reaction was monitored by TLC. The reaction mixture was concentrated under reduced pressure. The residue so obtained was taken in ethyl acetate (150 ml) and washed with saturated sodium bicarbonate solution (1×40 ml) followed by brine (1×20 ml). The organic layer separated was dried over anhydrous sodium sulphate, filtered and concentrated at reduced pressure to get a crude product. The crude product was purified by column chromatography over silica gel (100-200 mesh) using 15% ethyl acetate in hexanes as an eluent to obtain the title compound (1.38 g, 69.7%). MS: m/z 306 (M+1)

$^1$HNMR (CDCl$_3$, 400 MHz): δ 7.46 (s, 1H), 5.38 (d, J=13.6 Hz, 1H), 4.52 (d, J=13.2 Hz, 1H), 3.68 (m, 2H), 2.94 (dd, J=13.6, 10.8 Hz, 1H), 2.59 (dd, J=13.2, 10.8 Hz, 1H), 1.25 (d, J=5.6 Hz, 6H).

Step 2: (cis) (4-(4-chloroindolin-1-yl)thiazol-2-yl) (2,6-dimethylmorpholino) methanone

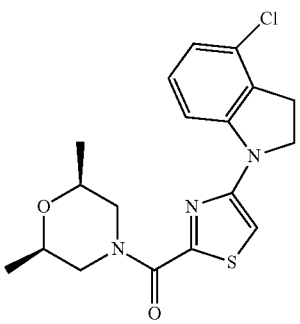 [SMILES: C[C@@H]1CN(C(=O)c2nc(N3CCc4c(Cl)cccc43)cs2)C[C@H](C)O1]

(cis) (4-bromothiazol-2-yl) (2,6-dimethylmorpholino) methanone (step-1 of compound 45, 1.0 g, 3.28 mmol) and 4-chloroindoline (0.55 g, 3.60 mmol) were added to seal tube containing toluene (25 ml). Sodium tert-butoxide (0.47 g. 4.91 mmol) was added, the nitrogen gas was bubbled through reaction mixture for 15 minutes and tris(dibenzylideneacetone)dipalladium(0) (0.15 g, 0.16 mmol) was added under nitrogen and the tube was sealed. The reaction mixture was heated at 100° C. for 18 hr under stirring. The progress of reaction was monitored by TLC. The reaction mixture was cooled to 25° C. and diluted with ethyl acetate (100 ml) and washed with water (25 ml). The organic layer was dried over sodium sulfate filtered and concentrated under reduced pressure to obtain a crude product; which was purified by flash column chromatography using 15% ethyl acetate in hexanes as an eluent to obtain the title compound (0.75 g, 60.6%). MS: m/z 378 (M+1).

$^1$HNMR (CDCl$_3$, 400 MHz): δ 7.52 (d, J=8.8 Hz, 1H), 7.18-7.05 (m, 2H), 6.33 (s, 1H), 5.56 (d, J=13.2 Hz, 1H), 4.56 (d, J=13.2 Hz, 1H), 3.99 (t, J=8.8 Hz, 2H), 3.82-3.66 (m, 2H), 3.24 (t, J=8.8 Hz, 2H), 3.10 (t, J=12.8 Hz, 1H), 2.63 (t, J=12.8 Hz, 1H), 1.41-1.22 (m, 6H).

Step 3: (cis) 4-(4-(4-chloroindolin-1-yl)-2-(2,6-dimethylmorpholine-4-carbonyl) thiazol-5-yl)benzenesulfonamide

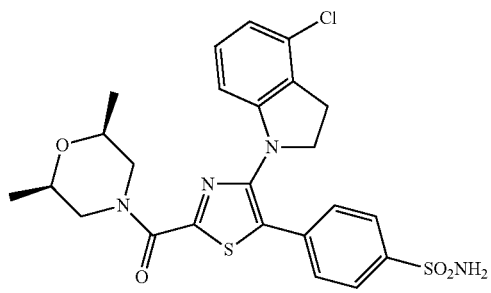 [SMILES: C[C@@H]1CN(C(=O)c2nc(N3CCc4c(Cl)cccc43)c(-c3ccc(S(N)(=O)=O)cc3)s2)C[C@H](C)O1]

To a solution of (cis) (4-(4-chloroindolin-1-yl)thiazol-2-yl) (2,6-dimethylmorpholino) methanone (Step-2, of compound 45, 0.6 g, 1.59 mmol in dimethyl acetamide (10 ml) were added 4-bromobenzenesulfonamide (0.41 g, 1.75 mmol) and potassium acetate (0.31 g, 3.18 mmol) at 25° C. in a tube, the nitrogen gas was bubbled through reaction mixture for 15 minutes. To this was added palladium (II) acetate (0.03 g, 0.16 mmol) under nitrogen and the tube was sealed. The reaction mixture was heated at 150° C. for 18 hr under stirring. The progress of reaction was monitored by TLC. The reaction mixture was cooled to 25° C. and concentrated under reduced pressure. The residue was dissolved in ethyl acetate (30 ml), reaction mixture was washed with water (2×10 ml), dried over sodium sulphate and concentrated under reduced pressure to obtain a crude product; which was purified by preparative HPLC to obtain the title compound (0.22 g, 26.0%). MS: m/z 533 (M+1).

$^1$HNMR (DMSO-d$_6$, 400 MHz): δ 7.85 (d, J=8.4 Hz, 2H), 7.79 (d, J=8.4 Hz, 2H), 7.44 (bs-exchanges with D$_2$O, 2H), 7.25-7.20 (m, 1H), 6.95 (dd, J=8.4 Hz, 2.4 Hz, 1H), 6.50 (d, J=8.4 Hz, 1H), 5.25 (d, J=12.8 Hz, 1H), 4.33 (d, J=8.4 Hz, 1H), 3.90-3.68 (m, 2H), 3.70-3.56 (m, 2H), 3.14 (t, J=8.4 Hz, 2H), 2.89 (t, J=12.8 Hz, 1H), 2.57 (t, J=12.8 Hz, 1H), 1.20-1.04 (m, 6H).

The following compounds were prepared according to the procedure described above but with appropriate changes to the reactants.

4-(2-(3-azabicyclo[3.1.0]hexane-3-carbonyl)-4-(4-chloroindolin-1-yl)thiazol-5-yl)benzenesulfonamide (Compound 89). MS: m/z 501 (M+1).

$^1$HNMR (DMSO-d$_6$, 400 MHz): δ 7.85-7.78 (m, 4H), 7.44 (bs-exchanges with D$_2$O. 2H), 7.23 (s, 1H), 6.95 (d, J=8.4 Hz, 1H), 6.38 (d, J=8.4 Hz, 1H), 4.39 (d, J=12.0, Hz. 1H). 3.93-3.82 (m, 4H), 3.57 (d, J=12.0, Hz, 1H), 3.17-3.13 (m, 2H). 1.75-1.71 (m, 1H), 1.63-1.60 (m, 1H), 0.75-0.72 (m, 1H), 0.18-0.14 (m, 1H).

(cis) 4-(2-(3-azabicyclo[3.1.0]hexane-3-carbonyl)-4-(2,6-dimethylmorpholino)thiazol-5-yl)benzenesulfonamide (Compound 90). MS: m/z 463 (M+1).

$^1$HNMR (DMSO-d$_6$, 400 MHz): δ 7.93 (d, J=8.4, Hz, 2H), 7.86 (d, J=8.4 Hz, 2H), 7.43 (bs-exchanges with D$_2$O, 2H), 4.44 (d, J=12.0, Hz, 1H), 3.92-3.75 (m, 4H), 3.58 (dd, J=12.0, 4.4 Hz, 1H), 3.17-3.15 (m, 2H), 2.60-2.54 (m, 2H), 1.77-1.74 (m, 1H). 1.65-1.61 (m, 1H). 1.07-1.04 (m, 6H), 0.77-0.74 (m, 1H), 0.18-0.14 (m, 1H).

Example 7

Preparation of 4-(4-(4-chlorophenyl)-2-(piperidine-1-carbonyl)thiazol-5-yl)-3-fluorobenzenesulfonamide (Compound 50)

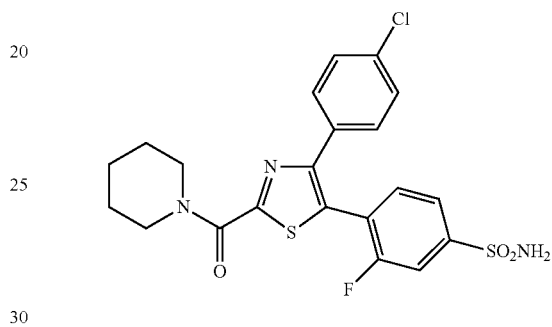

Step 1: (4-(4-chlorophenyl)thiazol-2-yl)(piperidin-1-yl)methanone

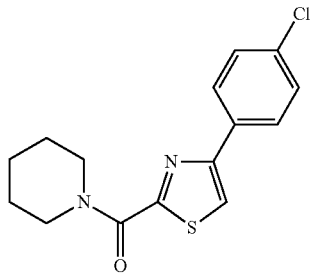 [SMILES: O=C(c1nc(-c2ccc(Cl)cc2)cs1)N1CCCCC1]

To a solution of 4-(4-chlorophenyl)thiazole-2-carboxylic acid (prepared according to the procedure given in US 2007/32531, 1.00 g, 4.17 mmol) in DMF (10 ml) was added HOST (0.96 g, 6.26 mmol) at room temperature, followed by the addition of piperidine (0.42 g, 5.01 mmol). The reaction mixture was cooled to 0° C. and to this were added EDC (1.20 g, 6.26 mmol) and triethylamine (2.11 g, 2.91 ml, 20.86 mmol). The reaction mixture was stirred at room temperature for 15 hr and the progress of reaction was monitored by TLC. The reaction mixture was concentrated under reduced pressure. The residue so obtained was taken in ethyl acetate (50 ml) and washed with saturated sodium bicarbonate solution (1×40 ml), brine (1×20 ml) and organic layers separated were dried over anhydrous sodium sulphate, filtered and concentrated under reduced pressure to get a crude product. The crude product was purified by column chromatography over silica gel (100-200 mesh) using 40% ethyl acetate in hexanes as an eluent to obtain the title compound (0.41 g, 32.4%). MS: m/z 308 (M+1).

$^1$HNMR (CDCl$_3$, 400 MHz): δ 7.84 (d, J=8.4 Hz, 2H), 7.66 (s, 1H), 7.43 (d, J=8.4 Hz, 2H), 4.37-4.34 (m, 2H), 3.77-3.74 (m, 2H), 1.78-1.72 (m, 6H).

Step 2: 4-(4-(4-chlorophenyl)-2-(piperidine-1-carbonyl)thiazol-5-yl)-3-fluorobenzenesulfonamide

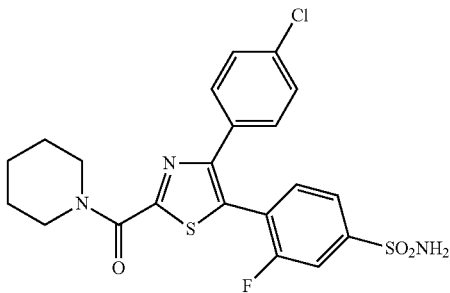 [SMILES: NS(=O)(=O)c1ccc(-c2sc(C(=O)N3CCCCC3)nc2-c2ccc(Cl)cc2)c(F)c1]

To a solution of (4-(4-chlorophenyl)thiazol-2-yl)(piperidin-1-yl)methanone (Step 1 of compound 50, 0.66 g, 2.16 mmol) in dimethyl acetamide (8 ml) were added 4-bromobenzenesulfonamide (0.55 g, 2.16 mmol) and potassium acetate (0.53 g, 5.41 mmol) at 25° C. in a tube, the nitrogen gas was bubbled through reaction mixture for 15 minutes. To this was added palladium (II) acetate (0.049 g, 0.21 mmol) under nitrogen and the tube was sealed. The reaction mixture was heated at 150° C. for 15 hr with stirring. The progress of reaction was monitored by TLC; the reaction mixture was cooled to 25° C. and concentrated under reduced pressure. The residue was dissolved in ethyl acetate (50 ml). The reaction mixture was washed with water (2×10 ml), dried over sodium sulphate and concentrated under reduced pressure to obtain a crude product; which was purified by column chromatography over silica gel (100-200 mesh) using 55% ethyl acetate in hexanes as an eluent to obtain the title compound (0.31 g, 29.8%). MS: m/z 480 (M+1).

$^1$HNMR (DMSO-d$_6$, 400 MHz): 7.76-7.69 (m, 3H), 7.63 (bs-exchanges with D$_2$O, 2H), 7.48-7.44 (m, 4H), 4.32-4.20 (m, 2H), 3.72-3.62 (m, 2H), 1.68-1.52 (m, 6H).

The following compounds were prepared according to the procedure described above but with appropriate changes to the reactants.

Compounds (mixture of two diastereomers) were separated by column chromatography as compound 15 and 16.

(+) 4-(4-(4-chlorophenyl)-2-(4-methoxy-cis-3,5-dimethylpiperidine-1-carbonyl)thiazol-5-yl)benzenesulfonamide (Compound 15). MS: m/z 520 (M+1). [α]$^{23}_D$: 0.90 (c=1.0, Acetone).

$^1$HNMR (DMSO-d$_6$, 400 MHz): δ 7.85 (d, J=8.4 Hz, 2H), 7.59 (d, J=8.4 Hz, 2H), 7.55-7.46 (m, 6H), 5.29 (d, J=12.8 Hz, 111), 4.39 (d, J=12.8 Hz, 1H), 3.39 (s, 3H), 2.90 (t, J=12.8 Hz, 1H), 2.70 (t, J=10.0 Hz, 1H), 2.58 (t, J=12.8 Hz, 1H), 1.75-1.61 (m, 2H), 1.03-0.95 (m, 6H).

(−) 4-(4-(4-chlorophenyl)-2-(4-methoxy-cis-3,5-dimethylpiperidine-1-carbonyl)thiazol-5-yl)benzenesulfonamide (Compound 16). MS: m/z 520 (M+1). [α]$^{23}_D$: −2.05 (c=1.0, Acetone).

$^1$HNMR (DMSO-d$_6$, 400 MHz): δ 7.85 (d, J=8.4 Hz, 2H), 7.59 (d, J=8.4 Hz, 2H), 7.47-7.42 (m, 6H), 5.03 (d, J=12.8 Hz, 1H), 4.17 (d, J=12.8 Hz, 1H), 3.45 (s, 3H), 3.23 (s, 1H), 3.01 (t, J=12.8 Hz, 1H), 2.68 (t, J=12.8 Hz, 1H), 1.91-1.75 (m, 2H), 1.03-0.95 (m, 6H).

(trans ±) 4-(2-(2,6-bis(fluoromethyl)morpholine-4-carbonyl)-4-(4-chlorophenyl)thiazol-5-yl)benzenesulfonamide (Compound 17). MS: m/z 528 (M+1).

$^1$HNMR (DMSO-d$_6$, 400 MHz): δ 7.85 (d, J=8.4 Hz, 2H), 7.60 (d, J=8.4 Hz, 2H), 7.49 (bs-exchanges with D$_2$O, 2H) 7.48-7.46 (m, 4H), 4.74-4.42 (m, 8H,) 3.97-3.92 (m, 1H), 3.57-3.51 (m, 1H).

4-(4-(4-chlorophenyl)-2-(3,3-difluoropiperidine-1-carbonyl)thiazol-5-yl)benzenesulfonamide (Compound 21). MS: m/z 498 (M+1).

$^1$HNMR (DMSO-d$_6$, 400 MHz): δ 7.85 (d, J=8.4 Hz, 2H), 7.61 (d, J=8.4 Hz, 2H), 7.52-7.35 (m, 6H), 4.82 (t, J=12.0 Hz, 1H), 4.35 (s, 1H), 4.04 (t, J=12.0 Hz, 1H), 3.72 (s, 1H) 2.21-2.07 (m, 2H), 1.88-1.72 (m, 2H).

4-(4-(4-chlorophenyl)-2-(4,4-difluoropiperidine-1-carbonyl)thiazol-5-yl)benzenesulfonamide (Compound 22). MS: m/z 498 (M+1).

$^1$HNMR (DMSO-d$_6$, 400 MHz): δ 7.85 (d, J=8.4 Hz, 2H), 7.60 (d, J=8.4 Hz, 2H), 7.50-7.42 (m, 6H), 4.50-4.42 (m, 2H), 3.85-3.72 (m, 2H), 2.16-2.04 (m, 4H).

(cis) 4-(4-(4-chlorophenyl)-2-(3,5-difluoropiperidine-1-carbonyl)thiazol-5-yl)benzenesulfonamide (Compound 23). MS: m/z 498 (M+1).

$^1$HNMR (DMSO-d$_6$, 400 MHz): δ 7.85 (d, J=8.4 Hz, 2H), 7.61 (d, J=8.4 Hz, 2H), 7.49-7.45 (m, 6H), 5.20-4.85 (m, 2H), 4.72-4.60 (m, 1H), 4.55-4.44 (m, 1H), 4.12-4.06 (m, 1H), 3.85-3.70 (m, 1H), 2.38-2.15 (m, 2H).

4-(4-(4-chlorophenyl)-2-(4-fluoro-cis-3,5-dimethylpiperidine-1-carbonyl)thiazol-5-yl)benzenesulfonamide (Compound 24). MS: m/z 508 (M+1).

$^1$HNMR (DMSO-d$_6$, 400 MHz): δ 7.85 (d, J=8.4 Hz, 2H), 7.60 (d, J=8.4 Hz, 2H), 7.49-7.42 (m, 6H), 5.36 (d, J=12.4 Hz, 1H), 4.46 (d, J=12.4 Hz, 1H), 4.14-3.97 (m, 1H), 2.98 (d, J=12.4 Hz, 1H), 2.68 (d, J=12.8 Hz, 1H), 1.91-1.75 (m, 2H), 1.05-0.99 (m, 6H).

4-(4-(4-chlorophenyl)-2-(pyrrolidine-1-carbonyl)thiazol-5-yl)benzenesulfonamide (Compound 25). MS: m/z 448 (M+1).

$^1$HNMR (DMSO-d$_6$, 400 MHz): δ 7.85 (d, J=8.4 Hz, 2H), 7.60 (d, J=8.4 Hz, 2H), 7.52-7.44 (m, 6H), 4.09 (t, J=6.8 Hz, 2H), 3.57 (t, J=6.8 Hz, 2H), 2.05-1.92 (m, 2H), 1.90-1.82 (m, 2H).

(S)-4-(4-(4-chlorophenyl)-2-(2-cyanopyrrolidine-1-carbonyl)thiazol-5-yl)benzenesulfonamide (Compound 26). MS: m/z 473 (M+1).

$^1$HNMR (DMSO-d$_6$, 400 MHz): δ 7.88-7.85 (m, 2H), 7.68-7.45 (m, 8H), 5.92-5.84 (m, 0.5H), 5.10-5.02 (m, 0.5H), 4.38-4.16 (m, 0.5H), 4.14-4.05 (m, 0.5H), 3.81-3.72 (m, 0.5H), 3.63-3.56 (m, 0.5H), 2.42-2.20 (m, 2H), 2.19-2.04 (m, 2H).

4-(4-(4-chlorophenyl)-2-(4,4-difluoropiperidine-1-carbonyl)thiazol-5-yl)-2-methylbenzenesulfonamide (Compound 51). MS: m/z 512 (M+1).

$^1$HNMR (DMSO-d$_6$, 400 MHz): δ 7.0 (d, J=8.0 Hz, 1H), 7.51 (bs-exchanges with D$_2$O, 2H), 7.49-7.46 (m, 5H), 7.34 (dd. J=8.0 Hz, 1.6 Hz, 1H), 4.51-4.40 (m, 2H), 3.85-3.78 (m, 2H), 2.56 (s, 3H), 2.24-2.05 (m, 4H).

4-(4-(4-chlorophenyl)-2-(pyrrolidine-1-carbonyl)thiazol-5-yl)-3-fluorobenzenesulfonamide (Compound 52). MS: m/z 466 (M+1).

$^1$HNMR (DMSO-d$_6$, 400 MHz): δ 7.78-7.70 (m, 3H), 7.63 (bs-exchanges with D$_2$O, 2H), 7.50-7.44 (m, 4H), 4.11 (t, J=6.8 Hz, 2H), 3.57 (t, J=6.8 Hz, 2H), 2.01-1.92 (m, 2H), 1.91-1.83 (m, 2H).

4-(4-(4-chlorophenyl)-2-(pyrrolidine-1-carbonyl)thiazol-5-yl)-2-fluorobenzenesulfonamide (Compound 53). MS: m/z 466 (M+1).

¹HNMR (DMSO-d₆, 400 MHz): δ 7.83-7.69 (m, 3H), 7.56-7.43 (m, 5H), 7.37 (d, J=8.4 Hz, 1H), 4.08 (t, J=6.8 Hz, 2H), 3.57 (t, J=6.8 Hz, 2H), 2.02-1.91 (m, 2H), 1.90-1.82 (m, 2H).

Example 8

Preparation of 4-(2-(3-oxa-8-azabicyclo[3.2.1]octan-8-yl)-4-(4-chlorophenyl)thiazol-5-yl)benzenesulfonamide (Compound 56)

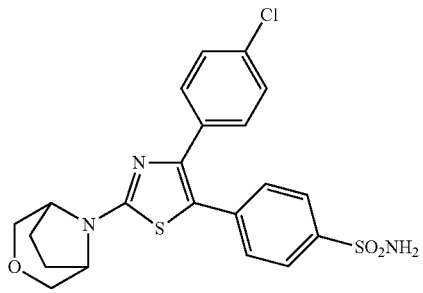 [SMILES: NS(=O)(=O)c1ccc(-c2sc(N3C4CCC3COC4)nc2-c2ccc(Cl)cc2)cc1]

Step 1: 8-(4-bromothiazol-2-yl)-3-oxa-8-azabicyclo[3.2.1]octane

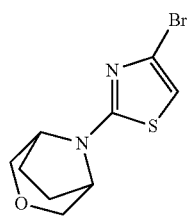 [SMILES: Brc1csc(N2C3CCC2COC3)n1]

To a stirred solution of 2,4-dibromothiazole (0.585 g, 2.41 mmol) in DMF (10 ml) were added 3-oxa-8-azabicyclo[3.2.1]octane (prepared according to the procedure given in WO 2010/120854, 0.3 g, 2.65 mmol) and DIPEA (0.47 gm, 0.63 ml, 3.62 mmol) under a stream of nitrogen. The reaction mixture was then stirred at 80° C. for 18 hrs and the progress of reaction was monitored by TLC. The reaction mixture was cooled to room temperature; quenched with cold water (20 ml) and extracted with ethyl acetate (3×30 ml). The combined organic layer was washed with water (2×10 ml), dried over sodium sulphate and concentrated to give crude compound; which was purified by flash column chromatography using 20% ethyl acetate in hexanes as an eluent to obtain the title compound (0.31 g, 46.7%). MS: m/z 276 (M+1).

¹HNMR (CDCl₃, 400 MHz): δ 6.47 (s, 1H), 4.17-4.12 (m, 2H), 3.90 (d, J=10.8 Hz, 2H), 3.60 (d, J=10.8 Hz, 2H), 2.13-2.02 (m, 4H).

Step 2: 8-(4-(4-chlorophenyl)thiazol-2-yl)-3-oxa-8-azabicyclo[3.2.1]octane

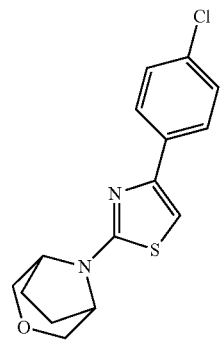 [SMILES: Clc1ccc(-c2csc(N3C4CCC3COC4)n2)cc1]

To a solution of 8-(4-bromothiazol-2-yl)-3-oxa-8-azabicyclo[3.2.1]octane (Step-1 of o compound 56, 0.29 g, 1.05 mmol) in a mixture of toluene:ethanol (1.5 ml:4.5 ml) were added (4-chlorophenyl) boronic acid (0.18 g, 1.16 mmol) and potassium carbonate (0.29 g, 2.11 mmol) at 25° C. in a tube, the nitrogen gas was bubbled through reaction mixture for 15 minutes. To the reaction mixture was added tetrakis(triphenylphosphine)palladium(0) (0.06 g, 0.05 mmol) under nitrogen and the tube was sealed. The reaction mixture was heated at 90-95° C. for 18 hr with stirring. The progress of reaction was monitored by TLC. The reaction mixture was cooled to 25° C. and filtered through celite. The residue was washed with mixture of 10% methanol in dichloromethane (2×10 ml). The filtrate was concentrated under reduced pressure to obtain a crude product; which was purified by flash column chromatography using 10% ethyl acetate in hexanes as an eluent to obtain the title compound (0.28 g, 88.0%). MS: m/z 307 (M+1).

¹HNMR (CDCl₃, 400 MHz): δ 7.78 (d, J=8.4 Hz, 2H), 7.35 (d, J=8.4 Hz, 2H), 6.80 (s, 1H), 4.26-4.24 (m, 2H), 3.98 (d, J=10.8 Hz, 2H), 3.63 (d, J=10.8 Hz, 2H), 2.14-2.06 (m, 4H).

Step 3: 8-(5-bromo-4-(4-chlorophenyl)thiazol-2-yl)-3-oxa-8-azabicyclo[3.2.1]octane

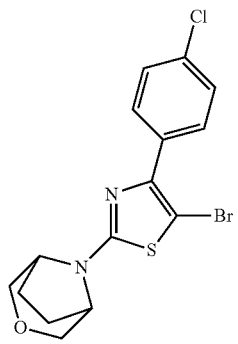 [SMILES: Clc1ccc(-c2nc(N3C4CCC3COC4)sc2Br)cc1]

To a stirred solution of 8-(4-(4-chlorophenyl)thiazol-2-yl)-3-oxa-8-azabicyclo[3.2.1]octane (Step-2 of compound 56, 0.27 g, 0.88 mmol) in DMF (5 ml) at 0° C. was added N-bromosuccinimide (0.19 g, 1.06 mmol) in a portion wise manner. The resulting mixture was stirred at room temperature for 30 min. The progress of reaction was monitored by TLC. To the reaction mixture water (20 ml) and 1M NaOH solution (5 ml)

were added slowly and aqueous layer was extracted with ethyl acetate (2×30 ml). The reaction mixture was washed with water (1×20 ml). The combined organic layer was dried over anhydrous Na$_2$SO$_4$ and the solvent was evaporated under reduced pressure to obtain a crude product; which was purified by flash column chromatography using 10% ethyl acetate in hexanes as an eluent to obtain the title compound (0.26 g, 78.0%). MS: m/z 386 (M+1).

$^1$HNMR (CDCl$_3$, 400 MHz): δ 7.87 (d, J=8.8 Hz, 2H), 7.38 (d, J=8.8 Hz, 2H), 4.15-4.12 (m, 2H), 3.94 (d, J=11.6 Hz, 2H), 3.63 (d, J=11.6 Hz, 2H), 2.14-2.06 (m, 4H).

Step 4: 4-(2-(3-oxa-8-azabicyclo[3.2.1]octan-8-yl)-4-(4-chlorophenyl)thiazol-5-yl)benzenesulfonamide

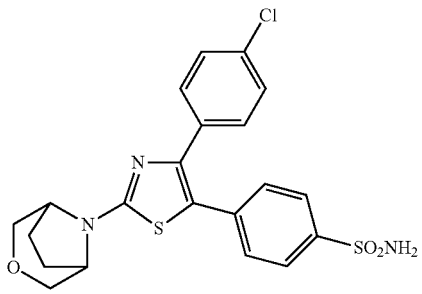

To a solution of 8-(5-bromo-4-(4-chlorophenyl)thiazol-2-yl)-3-oxa-8-azabicyclo[3.2.1]octane (Step 3 of compound 56, 0.26 g, 0.67 mmol) in a mixture of toluene:ethanol (2.5 ml:7.5 ml) were added 4-aminosulfonylbenzene boronic acid (0.15 g, 0.74 mmol) and potassium carbonate (0.23 g, 1.68 mmol) at 25° C. in a tube, the nitrogen gas was bubbled through reaction mixture for 15 minutes. To the reaction mixture was added tetrakis(triphenylphosphine)palladium(0) (0.039 g. 0.034 mmol) under nitrogen and the tube was sealed. The reaction mixture was heated at 90-95° C. for 18 hr with stirring. The progress of reaction was monitored by TLC. The reaction mixture was cooled to 25° C. and filtered through celite. The residue was washed with mixture of 10% methanol in dichloromethane (2×20 ml). The filtrate was concentrated under reduced pressure to obtain a crude product; which was purified by flash column chromatography using 2-3% methanol in DCM as an eluent to obtain the title compound (0.13 g, 41.7%). MS: m/z 462 (M+1).

$^1$HNMR (DMSO-d$_6$, 400 MHz): δ 7.75 (d, J=8.4 Hz, 2H), 7.44-7.38 (m, 8H), 4.13-4.11 (m, 2H), 3.78 (d, J=11.2 Hz, 2H), 3.59 (d, J=11.2 Hz, 2H), 2.00-1.88 (m, 4H).

The following compounds were prepared according to the procedure described above but with appropriate changes to the reactants.

(cis) 4-(4-(4-chlorophenyl)-2-(2,6-dimethylmorpholino)thiazol-5-yl)benzenesulfonamide (Compound 1). MS: m/z 464 (M+1).

$^1$HNMR (DMSO-d$_6$, 400 MHz): δ 7.75 (d, J=8.4 Hz, 2H), 7.43-7.40 (m, 8H), 3.80-3.66 (m, 4H), 2.76-2.70 (m, 2H), 1.16 (d, J=6.4 Hz, 6H).

4-(4-(4-chlorophenyl)-2-morpholinothiazol-5-yl)benzenesulfonamide (Compound 2). MS: m/z 436 (M+1).

$^1$HNMR (DMSO-d$_6$, 400 MHz): δ 7.74 (d, J=8.4 Hz, 2H), 7.41-7.39 (m, 8H), 3.74-3.72 (m, 4H), 3.46-3.42 (m, 4H).

4-(4-(4-chlorophenyl)-2-(4-methylpiperazin-1-yl)thiazol-5-yl)benzenesulfonamide (Compound 3). MS: m/z 449 (M+1).

$^1$HNMR (DMSO-d$_6$, 400 MHz): δ 7.73 (d, J=8.4 Hz, 2H), 7.43-7.37 (m, 8H), 3.48-3.43 (m, 4H), 2.45-2.39 (m, 4H), 2.23 (s, 3H).

4-(4-(4-chlorophenyl)-2-(piperidin-1-yl)thiazol-5-yl)benzenesulfonamide (Compound 4). MS: m/z 434 (M+1).

$^1$HNMR (CDCl$_3$, 400 MHz): δ 7.77 (d, J=8.4 Hz, 2H), 7.42 (d, J=8.8 Hz, 2H), 7.35 (d, J=8.8 Hz, 2H), 7.26 (d, J=8.4 Hz, 2H), 4.85 (bs-exchanges with D$_2$O, 2H), 3.98-3.56 (m, 4H) 1.78-1.65 (m, 6H).

(cis) 4-(4-(4-chlorophenyl)-2-(3,5-dimethylpiperidin-1-yl)thiazol-5-yl)benzenesulfonamide (Compound 5). MS: m/z 462 (M+1).

$^1$HNMR (DMSO-d$_6$, 400 MHz): δ 7.73 (d, J=8.4 Hz, 2H), 7.44-7.35 (m, 8H), 3.89 (dd, J=12.4, 3.2 Hz, 2H), 2.58 (t, J=12.4 Hz, 2H), 1.80-1.67 (m, 4H), 0.91 (d, J=6.8 Hz, 6H).

(trans ±) compounds (mixture of two enantiomers) were separated by chiral preparative HPLC.

(trans +) 4-(4-(4-chlorophenyl)-2-(3,5-dimethylpiperidin-1-yl)thiazol-5-yl)benzenesulfonamide (Compound 7). [α]$^{23}_D$: 32.32 (c=1.0, MeOH). MS: m/z 462 (M+1).

$^1$HNMR (DMSO-d$_6$, 400 MHz): δ 7.73 (d, J=8.4 Hz, 2H), 7.44-7.35 (m, 8H), 3.57 (dd, J=12.4, 4.0 Hz, 2H), 3.12 (dd, J=12.4, 6.8 Hz, 2H), 2.03-1.96 (m, 2H), 1.46 (t, J=6.8 Hz, 2H), 0.95 (d, J=6.8 Hz, 6H).

(trans −) 4-(4-(4-chlorophenyl)-2-(3,5-dimethylpiperidin-1-yl)thiazol-5-yl)benzenesulfonamide (Compound 8). MS: m/z 462 (M+1). [α]$^{23}_D$: −34.44 (c=1.0, MeOH).

$^1$HNMR (DMSO-d$_6$, 400 MHz): δ 7.73 (d, J=8.4 Hz, 2H), 7.42-7.35 (m, 8H), 3.57 (dd, J=12.4, 4.0 Hz, 2H), 3.12 (dd, J=12.4, 6.8 Hz, 2H), 2.03-1.96 (m. 2H), 1.46 (t, J=6.8 Hz, 2H), 0.95 (d, J=6.8 Hz, 6H).

4-(2-(8-oxa-3-azabicyclo[3.2.1]octan-3-yl)-4-(4-chlorophenyl)thiazol-5-yl)benzenesulfonamide (Compound 55). MS: m/z 462 (M+1).

$^1$HNMR (DMSO-d$_6$, 400 MHz): δ 7.73 (d, J=8.8 Hz, 2H), 7.42-7.37 (m, 8H), 4.50-4.44 (m, 2H), 3.54 (d, J=12.0 Hz, 2H), 3.26 (d, J=12.0 Hz, 2H), 1.95-1.66 (m, 4H).

4-(2-(8-azabicyclo[3.2.1]octan-8-yl)-4-(4-chlorophenyl)thiazol-5-yl)benzenesulfonamide (Compound 58). MS: m/z 460 (M+1).

$^1$HNMR (DMSO-d$_6$, 400 MHz): δ 7.72 (d, J=8.4 Hz, 2H), 7.45-7.36 (m, 8H), 4.26-4.18 (m, 2H), 2.10-2.02 (m, 2H), 1.96-1.79 (m, 5H), 1.57-1.43 (m, 3H).

4-(2-(3-azabicyclo[3.2.1]octan-3-yl)-4-(4-chlorophenyl)thiazol-5-yl)benzenesulfonamide (Compound 59). MS: m/z 460 (M+1).

$^1$HNMR (CDCl$_3$, 400 MHz): δ 7.77 (d, J=8.4 Hz, 2H), 7.35 (d, J=8.4 Hz, 2H), 7.28-7.25 (m, 4H), 4.83 (bs-exchanges with D$_2$O, 2H), 3.77-3.62 (m, 3H), 3.18 (d, J=12.0 Hz, 2H), 2.52-2.46 (m, 2H), 1.82-1.63 (m, 2H). 1.22-1.12 (m, 3H).

4-(2-(3-azabicyclo[3.1.0]hexan-3-yl)-4-(4-chlorophenyl)thiazol-5-yl)benzenesulfonamide (Compound 60). MS: m/z 432 (M+1).

$^1$HNMR (DMSO-d$_6$, 400 MHz): δ 7.72 (d, J=8.4 Hz, 2H), 7.42-7.34 (m, 8H), 3.61-3.54 (m, 4H), 1.77-1.70 (m, 2H), 0.83-0.76 (m, 1H), 0.28-0.21 (m, 1H).

(cis) 4-(4-(4-chlorophenyl)-2-(1,5-dimethyl-3-azabicyclo[3.1.0]hexan-3-yl)thiazol-5-yl)benzenesulfonamide (Compound 61). MS: m/z 460 (M+1).

¹HNMR (DMSO-d₆, 400 MHz): δ 7.72 (d, J=8.4 Hz, 2H), 7.43-7.34 (m, 8H), 3.62 (d, J=9.6 Hz, 2H), 3.33 (d, J=9.6 Hz, 2H), 1.21 (s, 6H), 0.53-0.44 (m, 2H).

Example 9

Preparation of 4-(2-(3-azabicyclo[3.1.0]hexan-3-yl)-4-(2,4-difluorophenyl)thiazol-5-yl)benzenesulfonamide. (Compound 66)

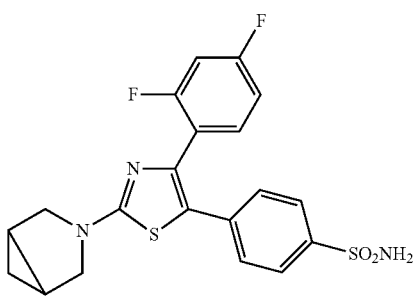 [SMILES: NS(=O)(=O)c1ccc(-c2sc(N3CC4CC4C3)nc2-c2ccc(F)cc2F)cc1]

Step 1:
2-(3-azabicyclo[3.1.0]hexan-3-yl)-4-bromothiazole

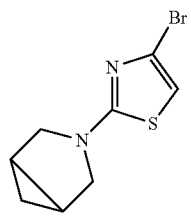 [SMILES: Brc1csc(N2CC3CC3C2)n1]

To a stirred solution of 2,4-dibromothiazole (0.5 g. 2.06 mmol) in DMF (15 ml) were added 3-azabicyclo[3.1.0]hexane hydrochloride (prepared according to the procedure given in Bioorganic and Medicinal Chemistry Letters, 2005, 15, 2093-2096, 0.27 g, 2.26 mmol) and DIPEA (0.80 g, 1.0 ml, 6.17 mmol) under a stream of nitrogen. The reaction was then stirred at 80° C. for 18 hrs; the progress of reaction was monitored by TLC. The reaction was quenched with cold water (20 ml) and extracted with ethyl acetate (3×30 ml). The combined organic layer was washed with water (2×10 ml), dried over sodium sulphate and concentrated to give crude compound; which was purified by flash column chromatography using 10% ethyl acetate in hexanes as an eluent to obtain the title compound (0.29 g, 58.5%). MS: m/z 246 (M+1).

¹HNMR (CDCl₃, 400 MHz): δ 6.33 (s, 1H), 3.62-3.51 (m, 4H), 1.69-1.66 (m, 2H), 0.84-0.79 (m, 1H), 0.28 (q, J=4.0 Hz, 1H).

Step 2: 2-(3-azabicyclo[3.1.0]hexan-3-yl)-4-(2,4-difluorophenyl)thiazole

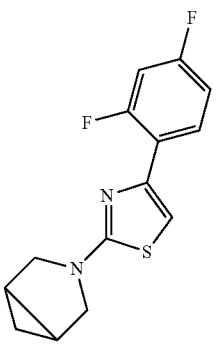 [SMILES: Fc1ccc(-c2csc(N3CC4CC4C3)n2)c(F)c1]

To a solution of 2-(3-azabicyclo[3.1.0]hexan-3-yl)-4-bromothiazole (Step-1 of compound 66, 0.29 g, 1.16 mmol) in a mixture of toluene: ethanol (4 ml:16 ml) were added (2,4-difluorophenyl) boronic acid (0.20 g, 1.28 mmol) and potassium carbonate (0.32 g, 2.32 mmol) at 25° C. in a tube, the nitrogen gas was bubbled through reaction mixture for 15 minutes. To the reaction mixture was added tetrakis(triphenylphosphine)palladium(0) (0.067 g, 0.058 mmol) under nitrogen and the tube was sealed. The reaction mixture was heated at 90-95° C. for 18 hr with stirring. The progress of reaction was monitored by TLC. The reaction mixture was cooled to 25° C. and filtered through celite; residue was washed with ethyl acetate (2×10 ml). The filtrate was concentrated under reduced pressure to obtain a crude product; which was purified by flash column chromatography using 10% ethyl acetate in hexanes as an eluent to obtain the title compound (0.25 g, 77.0%). MS: m/z 279 (M+1).

¹HNMR (CDCl₃, 400 MHz): δ 8.20-8.12 (m, 1H), 6.95-6.86 (m, 3H), 3.69 (d, J=10.0 Hz, 2H), 3.58-3.50 (m, 2H), 1.69-1.66 (m, 2H), 0.83-0.78 (m, 1H), 0.34 (q, J=4.0 Hz, 1H).

Step 3: 4-(2-(3-azabicyclo[3.1.0]hexan-3-yl)-4-(2,4-difluorophenyl)thiazol-5-yl)benzenesulfonamide

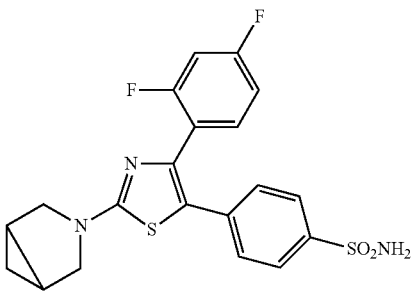 [SMILES: NS(=O)(=O)c1ccc(-c2sc(N3CC4CC4C3)nc2-c2ccc(F)cc2F)cc1]

To a solution of 2-(3-azabicyclo[3.1.0]hexan-3-yl)-4-(2,4-difluorophenyl)thiazole (Step 2 of compound 66, 0.23 g, 0.82 mmol) in dimethyl acetamide (5 ml) were added 4-bromobenzenesulfonamide (0.21 g, 0.90 mmol) and potassium acetate (0.16 g, 1.65 mmol) at 25° C. in a tube, the nitrogen gas was bubbled through reaction mixture for 15 minutes. To the reaction mixture was added palladium (II) acetate (0.019 gm, 0.08 mmol) under nitrogen and the reaction mixture was heated at 150° C. for 15 hr with stirring. The progress of reaction was monitored by TLC. The reaction mixture was cooled to 25° C. and concentrated under reduced pressure. The residue was dissolved in ethyl acetate (50 ml). The reaction mixture was washed with water (2×10 ml), dried over sodium sulphate and concentrated under reduced pressure to obtain a crude product; which was purified by flash column chromatography using 40% ethyl acetate in hexanes as an eluent to obtain the title compound (0.088 g, 24.5%). MS: m/z 434 (M+1).

¹HNMR (DMSO-d₆, 400 MHz): δ 7.67 (d, J=8.4 Hz, 2H), 7.53 (q, J=8.4 Hz, 1H), 7.28-7.14 (m, 6H), 3.54-3.51 (m, 4H), 1.74-1.71 (m, 2H), 0.83-0.78 (m, 1H), 0.26-0.24 (m, 1H).

The following compounds were prepared according to the procedure described above but with appropriate changes to the reactants.

(R)-4-(4-(4-chlorophenyl)-2-(3,4-dimethylpiperazin-1-yl)thiazol-5-yl)benzenesulfonamide (Compound 9). MS: m/z 463 (M+1).

¹HNMR (DMSO-d₆, 400 MHz): δ 7.73 (d, J=8.4 Hz, 2H), 7.43-7.38 (m, 8H), 2.84-2.78 (m, 2H), 3.22-3.15 (m, 1H), 2.84-2.78 (m, 2H), 2.25-2.12 (m, 5H), 1.05 (d, J=6.0 Hz, 3H).

4-(2-(6-oxa-3-azabicyclo[3.1.1]heptan-3-yl)-4-(4-chlorophenyl)thiazol-5-yl)benzenesulfonamide (Compound 57). MS: m/z 448 (M+1).

¹HNMR (DMSO-d₆, 400 MHz): δ 7.74 (d, J=8.4 Hz, 2H), 7.46-7.36 (m, 8H), 4.72 (d, J=6.4 Hz, 2H), 3.28-3.16 (m, 4H), 3.26-3.14 (m, 1H), 1.98-1.92 (m, 1H).

4-(4-(4-chlorophenyl)-2-(6-azaspiro[2.5]octan-6-yl)thiazol-5-yl)benzenesulfonamide (Compound 62). MS: m/z 460 (M+1).

¹HNMR (DMSO-d₆, 400 MHz): δ 7.74 (d, J=8.4 Hz, 2H), 7.44-7.38 (m, 8H), 3.55 (t, J=5.6 Hz, 4H), 1.45 (t, J=5.6 Hz, 4H), 0.38 (s, 4H).

4-(4-(4-chlorophenyl)-2-(5-azaspiro[2.5]octan-5-yl)thiazol-5-yl)benzenesulfonamide (Compound 63). MS: m/z 460 (M+1.

¹HNMR (DMSO-d₆, 400 MHz): δ 7.72 (d, J=8.4 Hz, 2H). 7.42-7.36 (m, 8H), 3.52 (t, J=5.2 Hz, 2H), 3.32 (s, 2H), 1.73-1.70 (m, 2H), 1.48 (t, J=5.2 Hz, 2H), 0.51 (t, J=4.4 Hz, 2H), 0.35 (t, J=4.4 Hz, 2H).

4-(4-(4-chlorophenyl)-2-(3,4-dihydroisoquinolin-2(1H)-yl)thiazol-5-yl)benzenesulfonamide (Compound 64). MS: m/z 482 (M+1).

¹HNMR (DMSO-d₆, 400 MHz): δ 7.75 (d, J=8.4 Hz, 2H), 7.48-7.39 (m, 8H), 7.29-7.20 (m, 4H), 4.69 (s, 2H), 3.78 (t, J=5.6 Hz, 2H), 2.94 (t, J=5.6 Hz, 2H).

4-(4-(4-chlorophenyl)-2-(3,4-dihydroquinolin-1(2H)-yl)thiazol-5-yl)benzenesulfonamide (Compound 65). MS: m/z 482 (M+1).

¹HNMR (DMSO-d₆, 400 MHz): δ 7.93 (dd, J=8.8, 1.2 Hz, 1H), 7.76 (d, J=8.4 Hz, 2H), 7.48-7.41 (m, 8H), 7.24-7.20 (m, 2H), 7.93 (dt, J=8.8, 1.2 Hz, 1H), 3.93 (t, J=6.0 Hz, 2H), 2.78 (t, J=6.0 Hz, 2H), 1.96 (quintet, J=6.0 Hz, 2H).

4-(4-(4-chlorophenyl)-2-(4-phenylpiperidin-1-yl)thiazol-5-yl)benzenesulfonamide (Compound 106). MS: m/z 510 (M+1).

¹HNMR (CDCl₃, 400 MHz): δ 7.78 (d, J=8.4 Hz, 2H), 7.43 (d, J=8.4 Hz, 2H), 7.39-7.22 (m, 9H), 5.03 (bs-exchanges with D₂O, 2H), 4.21 (d, J=12.0 Hz, 2H), 3.21 (d, J=10.8 Hz, 2H), 2.79 (t, J=12.0 Hz, 1H), 2.02-1.83 (m, 4H).

(cis) 4-(4-cyclopropyl-2-(2,6-dimethylmorpholino)thiazol-5-yl)benzenesulfonamide (Compound 6). MS: m/z 394 (M+1).

¹HNMR (DMSO-d₆, 400 MHz): δ 7.83 (d, J=8.0 Hz, 2H), 7.62 (d, J=8.0 Hz, 2H), 7.37 (bs-exchanges with D₂O, 2H), 3.72-3.58 (m, 4H), 2.64 (t, J=11.6 Hz, 2H), 2.02 (m, 1H), 1.15-0.90 (m, 6H), 0.92-0.84 (m, 4H).

Example 10

Preparation of 4-(4-(4-chlorophenyl)-2-(2-oxopiperidin-1-yl)thiazol-5-yl)benzenesulfonamide (Compound 10)

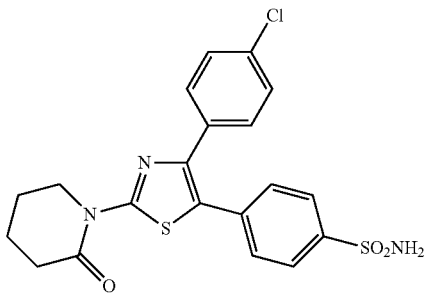 [SMILES: NS(=O)(=O)c1ccc(-c2sc(N3CCCCC3=O)nc2-c2ccc(Cl)cc2)cc1]

Step 1: 1-(4-bromothiazol-2-yl)piperidin-2-one

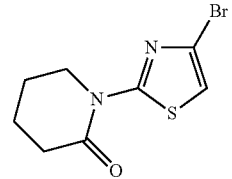 [SMILES: O=C1CCCCN1c1nc(Br)cs1]

2,4-dibromothiazole (2.0 g, 8.23 mmol) and piperidine-2-one (0.816 g. 8.23 mmol) were added to seal tube containing 1,4 dioxane (15 ml). Cesium carbonate (4.02 g, 12.35 mmol) and xantphos (027 g, 0.412 mmol) were added, the nitrogen gas was bubbled through reaction mixture for 15 minutes and tris(dibenzylideneacetone)dipalladium(0) (0.151 g, 0.165 mmol) was added under nitrogen and the tube was sealed. The reaction mixture was heated at 120° C. for 3 hr under stirring. The progress of reaction was monitored by TLC. The reaction mixture was cooled to 25° C. and diluted with water (50 ml) and extracted with ethyl acetate (3×100 ml). The combined organic extract was dried over sodium sulfate filtered and concentrated under reduced pressure to obtain a crude product; which was purified by flash column chromatography using 15% ethyl acetate in hexanes as an eluent to obtain the title compound (1.2 g, 55.8%). MS: m/z 262 (M+1).

¹HNMR (CDCl₃, 400 MHz): δ 6.90 (s, 1H), 4.16 (t, J=6.4 Hz, 2H), 2.69 (t, J=6.4 Hz, 2H), 2.06-1.98 (m, 2H), 1.96-1.90 (m, 2H).

Step 2: 1-(4-(4-chlorophenyl)thiazol-2-yl)piperidin-2-one

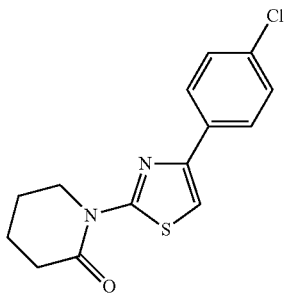 [SMILES: O=C1CCCCN1c1nc(-c2ccc(Cl)cc2)cs1]

To a solution of 1-(4-bromothiazol-2-yl)piperidin-2-one (Step-1 of compound 10, 1.0 g, 3.83 mmol) in a mixture of toluene:ethanol (10 ml: 30 ml) were added (4-chlorophenyl) boronic acid (0.72 g, 4.60 mmol) and potassium carbonate (1.06 g, 7.66 mmol) at 25° C. in a tube, the nitrogen gas was bubbled through reaction mixture for 15 minutes. To the reaction mixture was added tetrakis(triphenylphosphine)palladium(0) (0.44 g, 0.38 mmol) under nitrogen the tube was sealed. The reaction mixture was heated at 100° C. for 10 hr with stirring. The progress of reaction was monitored by TLC. The reaction mixture was cooled to 25° C. and filtered through celite. The residue was washed with ethyl acetate (2×30 ml). The filtrate was concentrated under reduced pressure to obtain a crude product; which was purified by flash column chromatography using 10% ethyl acetate in hexanes as an eluent to obtain the title compound (0.80 g, 71.4%). MS: m/z 293 (M+1).

$^1$HNMR (CDCl$_3$, 400 MHz): δ 7.84 (d, J=8.4 Hz, 2H), 7.40 (d, J=8.4 Hz, 2H), 7.19 (s, 1H), 4.29 (t, J=6.4 Hz, 2H), 2.73 (t, J=6.4 Hz, 2H), 2.08-1.98 (m, 2H), 1.97-1.92 (m, 2H).

Step 3: 4-(4-(4-chlorophenyl)-2-(2-oxopiperidin-1-yl)thiazol-5-yl)benzenesulfonamide

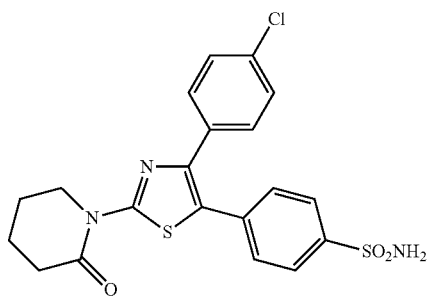 [SMILES: NS(=O)(=O)c1ccc(-c2sc(N3CCCCC3=O)nc2-c2ccc(Cl)cc2)cc1]

To a solution of 1-(4-(4-chlorophenyl)thiazol-2-yl)piperidin-2-one (Step 2 of compound 10, 0.5 g, 1.71 mmol) in dimethyl acetamide (5 ml) were added 4-bromobenzenesulfonamide (0.48 g, 2.05 mmol) and potassium acetate (0.42 g, 4.27 mmol) at 25° C. in a tube, the nitrogen gas was bubbled through reaction mixture for 15 minutes. To this was added palladium(II) acetate (0.02 g, 0.08 mmol) under nitrogen and the tube was sealed. The reaction mixture was heated at 150° C. for 15 hr under stirring. The progress of reaction was monitored by TLC. The reaction mixture was cooled to 25° C. and concentrated under reduced pressure. The residue was dissolved in ethyl acetate (30 ml), reaction mixture was washed with water (2×10 ml), dried over sodium sulphate and concentrated under reduced pressure to obtain a crude product; which was purified by preparative HPLC to obtain the title compound (0.25 g, 32.7%). MS: m/z 450 (M+1).

$^1$HNMR (DMSO-d$_6$, 400 MHz): δ 7.82 (d, J=8.4 Hz, 2H), 7.53 (d, J=8.4 Hz, 2H), 7.49-7.43 (m, 6H), 4.14 (t, J=6.4 Hz, 2H), 2.64 (t, J=6.4 Hz, 2H), 2.10-1.93 (m, 2H), 1.90-1.82 (m, 2H).

The following compounds were prepared according to the procedure described above but with appropriate changes to the reactants.

4-(4-(4-chlorophenyl)-2-(2-oxopyrrolidin-1-yl)thiazol-5-yl)benzenesulfonamide (Compound 11). MS: m/z 434 (M+1).

$^1$HNMR (DMSO-d$_6$, 400 MHz): 7.81 (d, J=8.4 Hz, 2H), 7.51 (d, J=8.4 Hz, 2H), 7.43-7.38 (m, 6H), 4.10 (d, J=7.2 Hz, 2H), 2.67 (t, J=4.8 Hz, 2H), 2.22-2.15 (m, 2H).

4-(4-(4-chlorophenyl)-2-(3-oxomorpholino)thiazol-5-yfi-benzenesulfonamide (Compound 12). MS: m/z 450 (M+1).

$^1$HNMR (DMSO-d$_6$, 400 MHz): δ 7.81 (d, J=8.4 Hz, 2H), 7.52 (d, J=8.4 Hz, 2H), 7.47-7.43 (m, 6H), 4.45 (s, 2H), 4.18 (t, J=4.8 Hz, 2H), 4.08 (t, J=4.8 Hz, 2H).

Example 11

4-(2-(3-azabicyclo[3.1.0]hexan-3-ylmethyl)-4-(4-chlorophenyl)thiazol-5-yl)benzenesulfonamide (Compound 102)

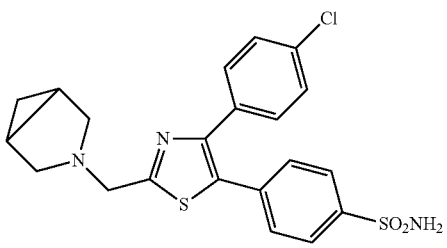 [SMILES: NS(=O)(=O)c1ccc(-c2sc(CN3CC4CC4C3)nc2-c2ccc(Cl)cc2)cc1]

Step 1: 2-(3-azabicyclo[3.1.0]hexan-3-ylmethyl)-4-bromothiazole

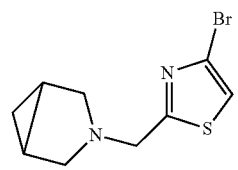 [SMILES: Brc1csc(CN2CC3CC3C2)n1]

A solution of methyl 4-bromo-2-(bromomethyl)thiazole (prepared according to the procedure reported in US 2010/298388, 0.60 g, 2.33 mmol) in DMF (5 ml) was added to a potassium carbonate (0.48 g, 3.50 mmol) and 3-azabicyclo [3.1.0]hexane hydrochloride (0.33 g, 2.80 mmol) at 0° C. under stirring. The reaction mixture was stirred at room temperature for 30 minutes. The progress of the reaction was monitored by TLC. The reaction mixture was quenched with water (5 ml). The mixture was then extracted with ethyl acetate (2×25 ml). The combined organic layer was dried over anhydrous Na$_2$SO$_4$. The solvent was evaporated from the dried organic layer under reduced pressure to obtain a crude product; the crud product was further purified by flash column chromatography using 20% ethyl acetate in hexanes as an eluent to obtain the title compound (0.47 g, 78%). MS: m/z 261 (M+1).

¹HNMR (CDCl₃, 400 MHz): δ 7.16 (s, 1H), 3.93 (s, 2H), 3.12 (d, J=8.4 Hz, 2H), 2.57 (d, J=8.4 Hz, 2H), 1.43-1.38 (m, 2H), 0.82-0.78 (m, 1H), 0.45-0.39 (m, 1H).

Step 2: 2-(3-azabicyclo[3.1.0]hexan-3-ylmethyl)-4-(4-chlorophenyl)thiazole

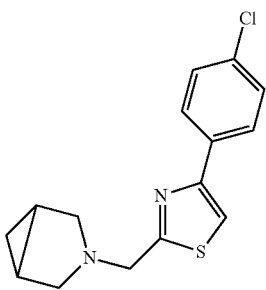 [SMILES: Clc1ccc(-c2csc(CN3CC4CC4C3)n2)cc1]

(4-chlorophenyl) boronic acid (0.34 g, 2.17 mmol) and potassium carbonate (0.63 g, 4.53 mmol) were added to a solution of 2-(3-azabicyclo[3.1.0]hexan-3-ylmethyl)-4-bromothiazole (Step-1 of compound 102, 0.47 g, 1.81 mmol) in a mixture of toluene:ethanol (5:15 ml) in a tube at 25° C. Nitrogen gas was bubbled through the reaction mixture for 15 minutes. Tetrakis(triphenylphosphine)(0)palladium (0.10 g, 0.09 mmol) was then added to the reaction mixture under nitrogen atmosphere and the tube was sealed. The reaction mixture was heated at 95-100° C. for 18 hr under stirring. The progress of the reaction was monitored by TLC. The reaction mixture was then cooled to 25° C. and filtered through celite. The celite cake was washed with ethanol (20 ml). The combined filtrate was concentrated under reduced pressure to obtain a crude product, which was then purified by column chromatography using 5% ethyl acetate in hexanes as an eluent to obtain the title compound (0.42 g, 79.0%). MS: m/z 291 (M+1).

¹HNMR (CDCl₃, 400 MHz): δ 7.83 (d, J=8.4 Hz, 2H), 7.43 (s, 1H), 7.40 (d, J=8.4 Hz, 2H), 4.03 (s, 2H), 3.20-3.15 (m, 2H), 2.65-2.61 (m, 2H), 1.43-1.41 (m, 2H), 0.89-0.87 (m, 1H), 0.45-0.39 (m, 1H).

Step 3: 4-(2-(3-azabicyclo[3.1.0]hexan-3-ylmethyl)-4-(4-chlorophenyl)thiazol-5-yl)benzenesulfonamide

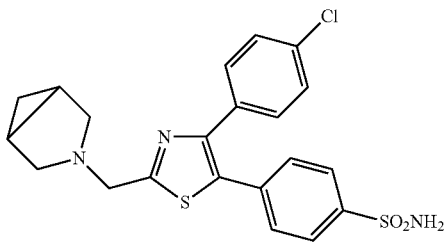 [SMILES: NS(=O)(=O)c1ccc(-c2sc(CN3CC4CC4C3)nc2-c2ccc(Cl)cc2)cc1]

4-bromobenzenesulfonamide (0.37 g, 1.57 mmol) and potassium acetate (0.28 g, 2.87 mmol) were added to a solution of 2-(3-azabicyclo[3.1.0]hexan-3-ylmethyl)-4-(4-chlorophenyl)thiazole (Step-2 of compound 102, 0.42 g, 1.43 mmol) in a DMA (5 ml) in a tube at 25° C. Nitrogen gas was bubbled through the reaction mixture for 15 minutes. Palladium acetate (0.032 g, 0.14 mmol) was then added to the reaction mixture under nitrogen atmosphere and the tube was sealed. The reaction mixture was heated at 150° C. for 20 hrs under stirring. The progress of the reaction was monitored by TLC. The reaction mixture was then cooled to 25° C. and filtered through celite. The celite cake was washed with ethyl acetate (20 ml). The combined filtrate was concentrated under reduced pressure to obtain a crude product, which was then purified by column chromatography using 30% ethyl acetate in hexanes as an eluent to obtain the title compound (0.14 g, 21.4%). MS: m/z 446 (M+1).

¹HNMR (DMSO-d₆, 400 MHz): δ 7.81 (d, J=8.4 Hz, 1H), 7.52 (d, J=8.4 Hz, 2H), 7.45 (bs-exchanges with D₂O, 2H), 7.42-7.38 (m, 4H), 3.98 (s, 2H), 3.11 (d, J=8.8 Hz, 1H), 2.55 (d, J=8.4, Hz, 2H), 1.43-1.41 (m, 2H), 0.69-0.67 (m, 1H), 0.41-0.36 (m, 1H).

Example 12

4-(4-(4-chlorophenyl)-2-((2-oxopyrrolidin-1-yl)methyl)thiazol-5-yl)benzenesulfonamide
(Compound 103)

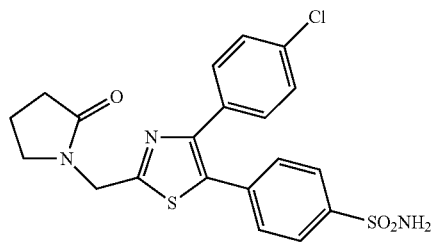 [SMILES: NS(=O)(=O)c1ccc(-c2sc(CN3CCCC3=O)nc2-c2ccc(Cl)cc2)cc1]

Step 1:
1-((4-bromothiazol-2-yl)methyl)pyrrolidin-2-one

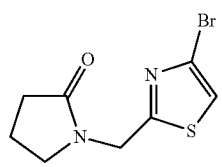 [SMILES: O=C1CCCN1Cc1nc(Br)cs1]

A solution of methyl 4-bromo-2-(bromomethyl)thiazole (prepared according to the procedure reported in US 2010/298388), (0.50 g, 1.94 mmol) in THF (5 ml) was added to a solution of sodium hydride (0.12 g 60% in paraffin oil, 2.92 mmol) and pyrrolidin-2-one (0.20 g, 2.33 mmol) in DMF (5 ml) at 0° C. under stirring. The reaction mixture was stirred at room temperature for 30 minutes. The progress of the reaction was monitored by TLC. The reaction mixture was quenched with water (5 ml). The mixture was then extracted with ethyl acetate (2×50 ml). The combined organic layer was dried over anhydrous Na₂SO₄. The solvent was evaporated from the dried organic layer under reduced pressure to obtain a crude product; the crud product was further purified by flash column chromatography using 60% ethyl acetate in hexanes as an eluent to obtain the title compound (0.40 g, 79%). MS: m/z 262 (M+1).

$^1$HNMR (CDCl$_3$, 400 MHz): δ 7.22 (s, 1H), 4.76 (s, 2H), 3.49 (t, J=8.0 Hz, 2H), 2.46 (t, J=8.0 Hz, 2H), 2.14-2.05 (m, 2H).

Step 2: 1-((4-(4-chlorophenyl)thiazol-2-yl)methyl) pyrrolidin-2-one

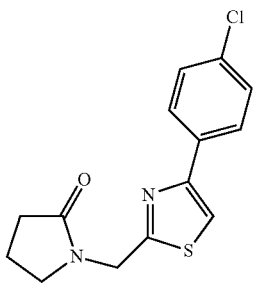 [SMILES: O=C1CCCN1Cc1nc(-c2ccc(Cl)cc2)cs1]

(4-chlorophenyl) boronic acid (0.22 g, 1.42 mmol) and potassium carbonate (0.41 g, 2.97 mmol) were added to a solution of 1-((4-bromothiazol-2-yl)methyl)pyrrolidin-2-one (Step-1 of Compound 103, 0.31 g, 1.18 mmol) in a mixture of toluene:ethanol (5:15 ml) in a tube at 25° C. Nitrogen gas was bubbled through the reaction mixture for 15 minutes. Tetrakis (triphenylphosphine)(0)palladium (0.07 g, 0.06 mmol) was then added to the reaction mixture under nitrogen atmosphere and the tube was sealed. The reaction mixture was heated at 95-100° C. for 1hr under stirring. The progress of the reaction was monitored by TLC. The reaction mixture was then cooled to 25° C. and filtered through celite. The celite cake was washed with ethanol (20 ml). The combined filtrate was concentrated under reduced pressure to obtain a crude product, which was then purified by column chromatography using 40% ethyl acetate in hexanes as an eluent to obtain the title compound (0.3 g, 86.6%).

MS: m/z 294 (M+1).
$^1$HNMR (CDCl$_3$, 400 MHz): δ 7.82 (d, J=8.8 Hz, 2H), 7.44 (s, 1H), 7.38 (d, J=8.8 Hz, 2H), 4.83 (s, 2H), 3.53 (t, J=7.6 Hz, 2H), 2.48 (t, J=7.6 Hz, 2H), 2.14-2.08 (m, 2H).

Step 3: 4-(4-(4-chlorophenyl)-2-((2-oxopyrrolidin-1-yl)methyl)thiazol-5-yl)benzenesulfonamide

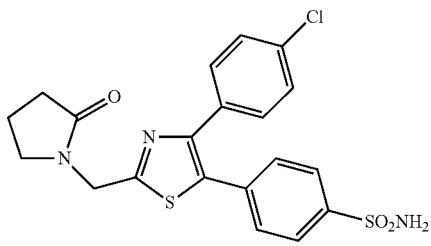 [SMILES: NS(=O)(=O)c1ccc(-c2sc(CN3CCCC3=O)nc2-c2ccc(Cl)cc2)cc1]

4-bromobenzenesulfonamide (0.26 g, 1.12 mmol) and potassium acetate (0.2 g, 2.04 mmol) were added to a solution of 1-((4-(4-chlorophenyl)thiazol-2-yl)methyl)pyrrolidin-2-one (Step-2 of Compound 103, 0.30 g, 1.02 mmol) in a DMA (5 ml) in a tube at 25° C. Nitrogen gas was bubbled through the reaction mixture for 15 minutes. Palladium acetate (0.023 g, 0.10 mmol) was then added to the reaction mixture under nitrogen atmosphere and the tube was sealed. The reaction mixture was heated at 150° C. for 4 hrs under stirring. The progress of the reaction was monitored by TLC. The reaction mixture was then cooled to 25° C. and filtered through celite. The celite cake was washed with ethyl acetate (20 ml). The combined filtrate was concentrated under reduced pressure to obtain a crude product, which was then purified by column chromatography using 50% ethyl acetate in hexanes as an eluent to obtain the title compound (0.11 g, 25.0%). MS: m/z 449 (M+1).

$^1$HNMR (DMSO-d$_6$, 400 MHz): δ 7.81 (d, J=8.4 Hz, 2H), 7.53 (d, J=8.4 Hz, 2H), 7.46 (bs-exchanges with D$_2$O, 2H), 7.43 (s, 4H), 4.73 (s, 2H), 3.50 (t, J=7.2 Hz, 2H), 2.33 (t, J=7.2 Hz, 2H), 2.03-1.96 (m, 2H).

The following compounds were prepared according to the procedure described above but with appropriate changes to the reactants.

4-(4-(4-chlorophenyl)-2-((2-oxopyrrolidin-1-yl)methyl) thiazol-5-yl)-3-fluorobenzenesulfonamide (Compound 104). MS: m/z 466 (M+1).

$^1$HNMR (DMSO-d$_6$, 400 MHz): δ 7.72-7.67 (m, 3H), 7.61 (br-s, exchanges with D$_2$O, 2H), 7.43 (s, 4H), 4.71 (s, 2H), 3.51 (t, J=7.6 Hz, 2H), 2.32 (t, J=7.6 Hz, 2H), 2.04-1.90 (m, 2H).

4-(4-(4-chlorophenyl)-2-((2-oxopiperidin-1-yl)methyl) thiazol-5-yl)benzenesulfonamide (Compound 105). MS: m/z 462 (M+1).

$^1$HNMR (DMSO-d$_6$, 400 MHz): δ 7.80 (d, J=8.4 Hz, 2H), 7.50 (d, J=8.4 Hz, 2H), 7.45 (br-s, exchanges with D$_2$O, 2H), 7.43 (s, 4H), 4.77 (s, 2H), 3.46 (t, J=6.4 Hz, 2H), 2.32 (t, J=6.4 Hz, 2H), 1.86-1.74 (m, 4H).

Example 13

Pharmacological Screening

Compounds were tested in a cell-based real-time kinetic assay in human IMR-32 cells with native expression of α7 nAChR. The increase in intracellular Ca$^{2+}$ levels was measured in a Fluorometric Imaging Plate Reader (FLIPR). Test compound and agonist solutions were made in assay buffer (HBSS, pH 7.4, 20 mM HEPES, and 10 mM CaCl$_2$) Briefly, cells were plated into Poly-D-Lysine coated back-walled clear-bottom 96-well microplates at a density of 80,000 to 100,000 cells/well and incubated at 37° C./5% CO$_2$ for 40-48 h prior to the experiment. For evaluation of compound mediated potentiation of agonist response, growth media was removed from the wells and 200 μl of FLIPR calcium 4 dye (Molecular Devices), reconstituted in assay buffer, and was added to the wells. After dye loading, microplates were incubated for 30 min at 37° C. and 30 min at room temperature and then directly transferred to the FLIPR. Baseline fluorescence was monitored for the first 10 to 30 s followed by the addition of 25 μl of test compound solution and subsequent monitoring of fluorescence changes for up to 10 min. This was followed by addition of 25 μl of agonist solution (PNU-282987, 10 μM) and measurement of fluorescence for 4 min. (Faghih R. et al. 2009, J. Med. Chem., 52, 3377-84.)

The compound induced fold increase in agonist response (fold PAM activity) was computed by dividing the maximum effect (Max-Min fluorescence) obtained with test compound in presence of agonist with the agonist-alone effect. EC$_{50}$ of the compound was calculated using GraphPad Prism software version 5.0, by plotting compound concentrations against fold PAM activity.

Fold activity at 1 µM concentration: compounds with activity between 1 to 5 folds are grouped as A, the compounds with activity between 5.1 folds and 15 folds are grouped as B and the compounds with activity above 15 folds are grouped as C.

Following table 1 provides fold activity of the compounds of the present invention

TABLE 1

| Sr. No. | Fold activation at 1 µM conc. (Group) | Compound No. |
|---|---|---|
| 1 | A | 5, 6, 14, 15, 16, 17, 18, 19, 20, 21, 22, 23, 24, 25, 27, 31, 32, 33, 34, 35, 36, 39, 41, 42, 43, 44, 45, 54, 55, 56, 57, 59, 61, 64, 65, 67, 68, 69, 70, 71, 72, 74, 75, 76, 77, 78, 81, 82, 83, 88, 89, 90, 91, 92, 93, 95, 96, 100, 102. |
| 2 | B | 1, 3, 29, 30, 38, 51, 58, 62, 86, 103, 105, 106. |
| 3 | C | 2, 4, 7, 8, 10, 11, 12, 13, 25, 28, 37, 40, 46, 47, 48, 49, 50, 52, 53, 60, 63, 66, 73, 79, 80, 84, 85, 87, 94, 97, 98, 99, 101, 104, |

The invention claimed is:

1. A compound of formula I, a tautomeric form, a stereoisomer, or a pharmaceutically acceptable salt thereof,

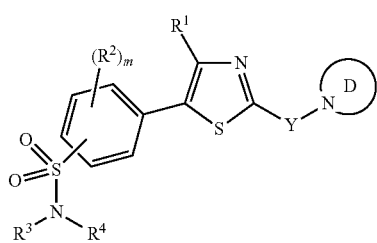

(I)

wherein, in the compound of formula I,
ring D is substituted- or unsubstituted-5 to 12 membered heterocycle optionally containing 1 to 3 additional heteroatom(s)/group(s) selected from —S(O)$_n$—, —NR$^5$—, and —O—;
ring D may be substituted on ring carbons with 1 to 6 substituent(s) independently selected from halogen, nitro, cyano, oxo, substituted- or unsubstituted-alkyl, perhaloalkyl, substituted- or unsubstituted-cycloalkyl, substituted- or unsubstituted-aryl, substituted- or unsubstituted-heteroaryl, substituted- or unsubstituted-heterocyclyl, R$^{6b}$O—, R$^6$N(H)C(=O)—, R$^{6a}$C(=O)N(H)—, R$^6$N(R$^7$)—, and R$^6$N(H)C(=O)N(H)—;
Y is a bond, —CH$_2$—, or —C(=O)—;
R$^1$ is selected from substituted- or unsubstituted-aryl, substituted- or unsubstituted-heteroaryl, substituted- or unsubstituted-cycloalkyl, and substituted- or unsubstituted-heterocyclyl;
R$^2$ is independently selected at each occurrence from halogen, nitro, cyano, substituted- or unsubstituted-alkyl, perhaloalkyl, substituted- or unsubstituted-cycloalkyl, substituted- or unsubstituted-heterocyclyl, R$^{6b}$O—, and R$^{6a}$C(=O)—, or
two R$^2$ groups and the carbon atoms to which they are attached together form a 5- to 6-membered cyclic system which optionally contains 1 to 3 heteroatom(s) selected from —N—, —S—, and —O—, said 5- to 6-membered cyclic system may be substituted with 1 to 3 substituent(s) independently selected from oxo, halogen, cyano, and alkyl;
R$^3$ and R$^4$ are independently selected from hydrogen, R$^{6a}$C(=O)—, substituted- or unsubstituted-alkyl, substituted- or unsubstituted-cycloalkyl, and substituted- or unsubstituted-heterocyclyl; or
R$^3$ and R$^4$ together with the nitrogen atom to which they are attached form a 3- to 10-membered heterocyclic ring system containing one to three heteroatom(s) selected from —S—, —N—, and —O—, said 3- to 10-membered heterocyclic ring system may be substituted with 1 to 3 substituent(s) independently selected from oxo, halogen, alkyl, OR$^{6b}$, and R$^6$N(H)—;
R$^5$ is selected from hydrogen, substituted- or unsubstituted-alkyl, substituted- or unsubstituted-cycloalkyl, substituted- or unsubstituted-aryl, substituted- or unsubstituted-heterocyclyl, R$^{6a}$C(=O)—, and R$^6$N(R$^7$)C(=O)—;
R$^6$ and R$^7$ are each independently selected from hydrogen, substituted- or unsubstituted-alkyl, substituted- or unsubstituted-cycloalkyl, and substituted- or unsubstituted-heterocyclyl;
R$^{6a}$ is selected from substituted- or unsubstituted-alkyl, perhaloalkyl, substituted- or unsubstituted-cycloalkyl, and substituted- or unsubstituted-heterocyclyl;
R$^{6b}$ is selected from hydrogen, substituted- or unsubstituted-alkyl, perhaloalkyl, substituted- or unsubstituted-cycloalkyl, and substituted- or unsubstituted-heterocyclyl;
m is an integer selected from 0, 1, 2, and 3;
n is an integer selected from 0, 1, and 2;
when the alkyl group is a substituted alkyl group, the alkyl group is substituted with 1 to 4 substituents selected independently from oxo, halogen, nitro, cyano, perhaloalkyl, substituted- or unsubstituted-cycloalkyl, substituted- or unsubstituted-aryl, substituted- or unsubstituted-heteroaryl, substituted- or unsubstituted-heterocyclyl, R$^{8b}$O—, R$^{8a}$S(O$_2$)—, R$^{8a}$OC(=O)—, R$^{8a}$C(=O)O—, R$^8$N(H)C(=O)—, R$^8$N(alkyl)C(=O)—, R$^{8a}$C(=O)N(H)—, R$^8$N(H)—, R$^8$N(alkyl)-, R$^8$N(H)C(=O)N(H)—, and R$^8$N(alkyl)C(=O)N(H)—;
when the cycloalkyl and the carbocyclic groups are substituted, each of them is substituted with 1 to 3 substituents selected independently from oxo, halogen, nitro, cyano, substituted- or unsubstituted-alkyl, perhaloalkyl, substituted- or unsubstituted-aryl, substituted- or unsubstituted-heteroaryl, substituted- or unsubstituted-heterocyclyl, R$^{8b}$O—, R$^{8c}$S(O$_2$)—, R$^{8c}$C(=O)—, R$^{8c}$OC(=O)—, R$^{8c}$C(=O)O—, R$^{8d}$N(H)C(=O)—, R$^{8d}$N(alkyl)C(=O)—, R$^{8c}$C(=O)N(H)—, R$^{8d}$N(H)—, R$^{8d}$N(alkyl)-, R$^{8d}$N(H)C(=O)N(H)—, and R$^{8d}$N(alkyl)C(=O)N(H)—;
when the aryl group is substituted, it is substituted with 1 to 3 substituents selected independently from halogen, nitro, cyano, hydroxy, substituted- or unsubstituted-alkyl, perhaloalkyl, substituted- or unsubstituted-cycloalkyl, substituted- or unsubstituted-heterocycle, (alkyl)O—, (perhaloalkyl)O—, (alkyl)N(alkyl)-, (alkyl)N(H)—, H$_2$N—, (alkyl)S(=O$_2$)—, (perhaloalkyl)S(O$_2$)—, (alkyl)C(=O)N(alkyl)-, (alkyl)C(=O)N(H)—, (alkyl)N(alkyl)C(=O)—, (alkyl)N(H)C(=O)—, H$_2$NC(=O)—, (alkyl)N(alkyl)S(O$_2$)—, (alkyl)N(H)S(O$_2$)—, and H$_2$NS(O$_2$)—;
when the heteroaryl group is substituted, it is substituted with 1 to 3 substituents selected independently from halogen, nitro, cyano, hydroxy, substituted- or unsubstituted-alkyl, perhaloalkyl, substituted- or unsubstituted-cycloalkyl, substituted- or unsubstituted-heterocycle, (alkyl)O—, (perhaloalkyl)O—, (alkyl)N(alkyl)-, (alkyl)N(H)—, H$_2$N—, (alkyl)S(O$_2$)—, (perhaloalkyl)S(O$_2$)—, (alkyl)C(=O)N(alkyl)-, (alkyl)C(=O)N(H)—, (alkyl)N(alkyl)C(=O)—, (alkyl)N(H)C(=O)—, H$_2$NC(=O)—, (alkyl)N(alkyl)S(O$_2$)—, (alkyl)N(H)S(O$_2$)—, and H$_2$NS(O$_2$)—;

when the heterocyclic group is substituted, it can be substituted either on a ring carbon atom or on a ring hetero atom, and when the heterocyclic group is substituted on a ring carbon atom, it is substituted with 1-3 substituents selected independently from halogen, nitro, cyano, oxo, substituted- or unsubstituted-alkyl, perhaloalkyl, substituted- or unsubstituted-cycloalkyl, substituted- or unsubstituted-aryl, substituted- or unsubstituted-heteroaryl, substituted- or unsubstituted-heterocyclyl, R$^{8b}$O—, R$^{8c}$OC(=O)—, R$^{8c}$C(=O)O—, R$^{8d}$N(H)C(=O)—, R$^{8d}$N(alkyl)C(=O)—, R$^{8c}$C(=O)N(H)—, R$^{8d}$N(H)—, R$^{8d}$N(alkyl)-, R$^{8d}$N(H)C(=O)N(H)—, and R$^{8d}$N(alkyl)C(=O)N(H)—; when the heterocyclic group is substituted on a ring nitrogen, it is substituted with a substituent selected from substituted- or unsubstituted-alkyl, substituted- or unsubstituted-cycloalkyl, substituted- or unsubstituted-aryl, substituted- or unsubstituted-heteroaryl, R$^{8a}$S(O$_2$)—, R$^{8a}$C(=O)—, R$^{8a}$OC(=O)—, R$^{8}$N(H)C(=O)—, and R$^{8}$N(alkyl)C(=O)—;

R$^{8}$ is selected from hydrogen, alkyl, cycloalkyl, aryl, heteroaryl, and heterocyclyl;

R$^{8a}$ is selected from alkyl, perhaloalkyl, cycloalkyl, aryl, heteroaryl, and heterocyclyl;

R$^{8b}$ is selected from hydrogen, alkyl, perhaloalkyl, cycloalkyl, aryl, heteroaryl, and heterocyclyl;

R$^{8c}$ is selected from alkyl, perhaloalkyl, and cycloalkyl; and

R$^{8d}$ is selected from hydrogen, alkyl, and cycloalkyl.

2. The compound of formula I, a tautomeric form, a stereoisomer, or a pharmaceutically acceptable salt thereof, as claimed in claim 1, wherein ring D is selected from

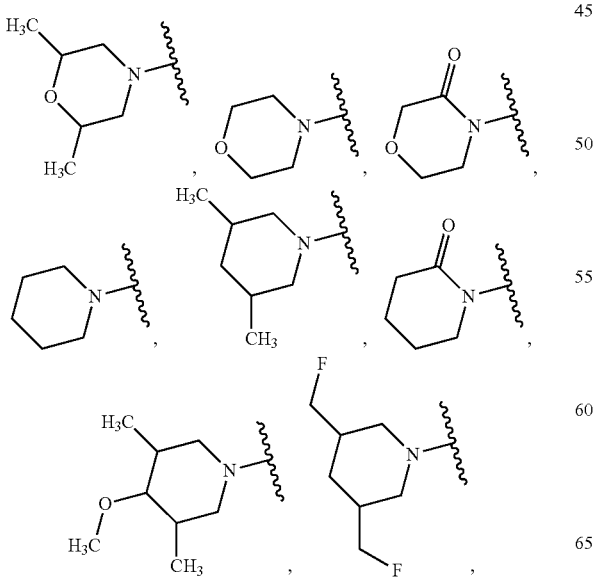

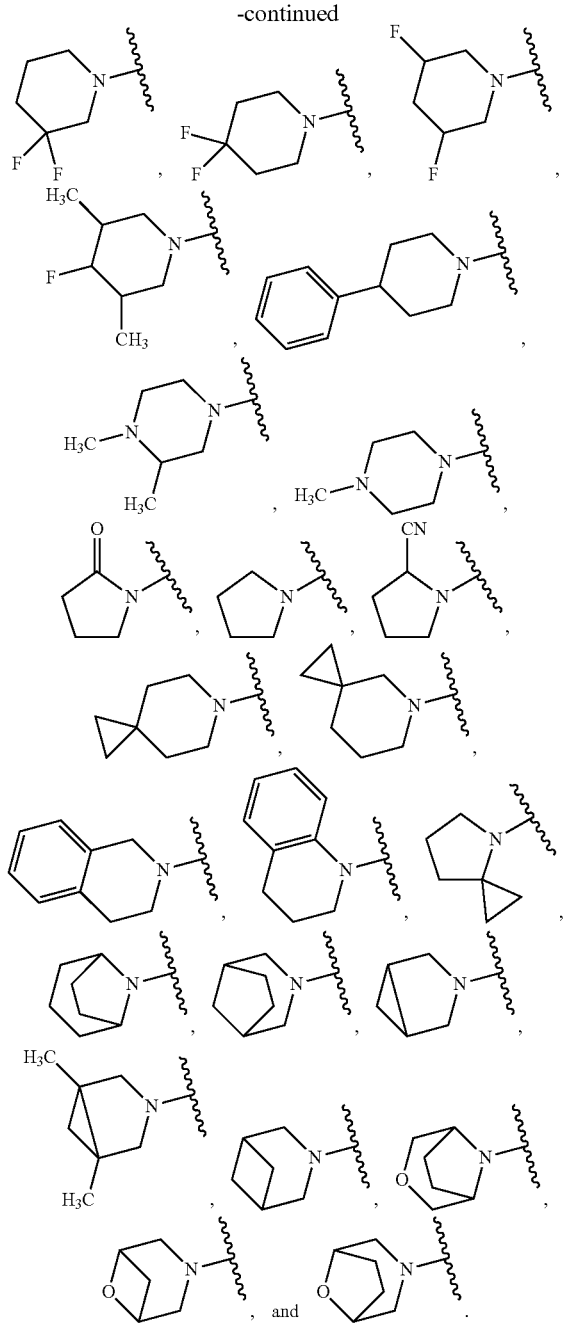

3. The compound of formula I, a tautomeric form, a stereoisomer, or a pharmaceutically acceptable salt thereof, as claimed in claim 1, wherein R$^1$ is selected from
a)

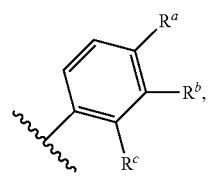

wherein R$^a$ is selected from halogen, cyano, cyclopropyl, methyl, trifluoromethyl, dimethylamino, H$_3$CS (O₂)—, H₂NC(=O)—, H₃CC(=O)N(H)—, and (CH₃)₂NC(=O)—; $R^b$ is selected from hydrogen, halogen, cyclopropyl, and methyl; and $R^c$ is selected from hydrogen and halogen;

b)

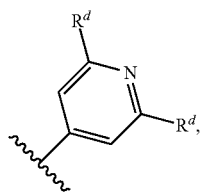

wherein $R^d$ is independently selected at each occurrence from hydrogen and methyl;

c)

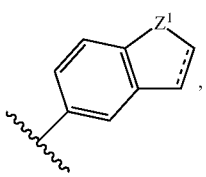

wherein, $Z^1$ is selected from —CH₂—, —N(H)—, —N(CH₃)—, and —N(COCH₃)—; ----- is either a single bond or a double bond; and d) cyclopropyl,

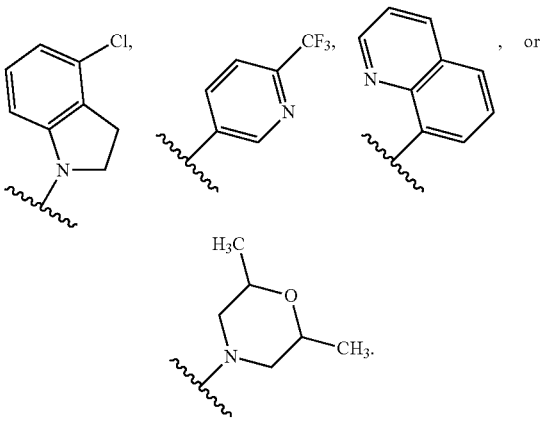

4. The compound of formula I, a tautomeric form, a stereoisomer, or a pharmaceutically acceptable salt thereof, as claimed in claim 1, wherein $R^2$ is selected from substituted- or unsubstituted-alkyl, halogen, and perhaloalkyl; or two $R^2$ groups and the carbon atoms to which they are attached together form a substituted- or unsubstituted-5 to 6 membered carbocycle.

5. The compound of formula I, a tautomeric form, a stereoisomer, or a pharmaceutically acceptable salt thereof, as claimed in claim 1, wherein $R^2$ is selected from methyl, fluoro, and trifluoromethyl; or two $R^2$ groups and two adjacent carbon atoms to which they are attached together form a six membered carbocycle.

6. The compound of formula I, a tautomeric form, a stereoisomer, or a pharmaceutically acceptable salt thereof, as claimed in claim 1, wherein m is selected from 0, 1, and 2.

7. The compound of formula I, a tautomeric form, a stereoisomer, or a pharmaceutically acceptable salt thereof, as claimed in claim 1, wherein $R^3$ and $R^4$ are selected independently from hydrogen, substituted- or unsubstituted-alkyl, and $R^{6a}C(=O)$—; or $R^3$, $R^4$ and the nitrogen to which they are attached together form a 3- to 10-membered heterocycle.

8. The compound of formula I, a tautomeric form, a stereoisomer, or a pharmaceutically acceptable salt thereof, as claimed in claim 1, wherein $R^3$ and $R^4$ are selected independently from hydrogen, methyl, and acetyl; or $R^3$, $R^4$ and the nitrogen to which they are attached together form a piperidinyl ring.

9. The compound of formula I, a tautomeric form, a stereoisomer, or a pharmaceutically acceptable salt thereof, as claimed in claim 1, wherein ring D is selected from

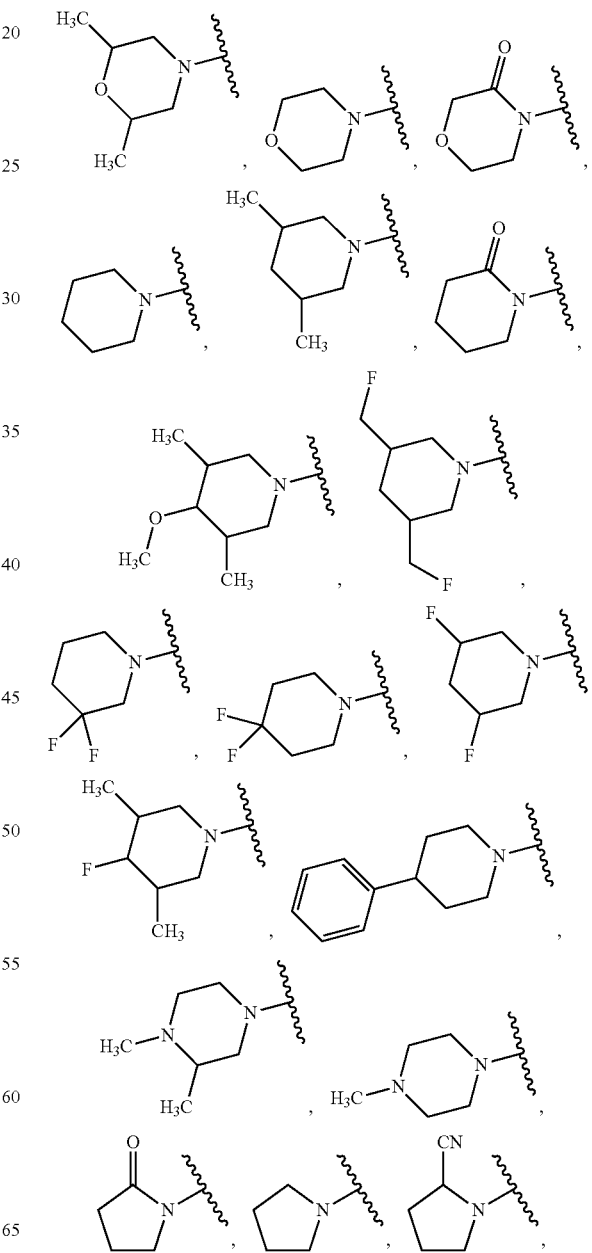

-continued

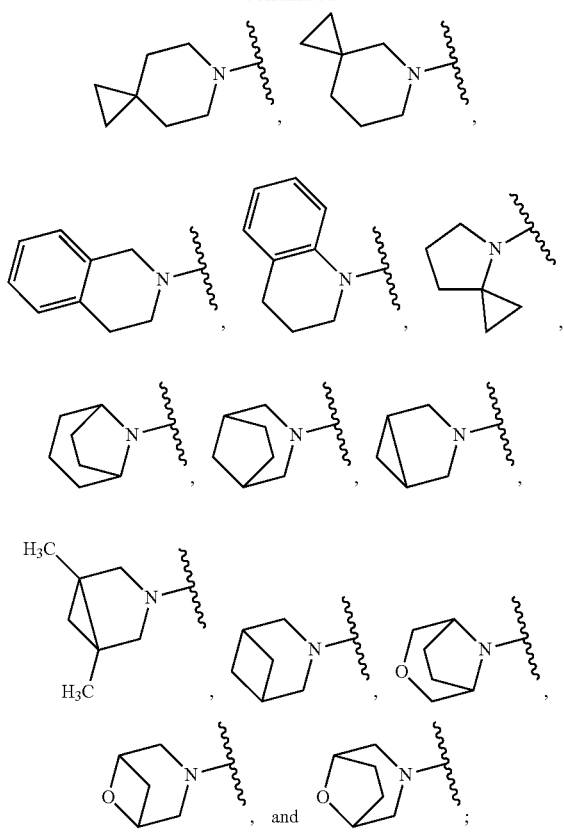

R[1] is selected from
a)

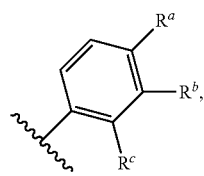

wherein R[a] is selected from halogen, cyano, cyclopropyl, methyl, trifluoromethyl, dimethylamino, H₃CS(O₂)—, H₂NC(=O)—, H₃CC(=O)N(H)—, and (CH₃)₂NC(=O)—; R[b] is selected from hydrogen, halogen, cyclopropyl, and methyl; R[c] is selected from hydrogen, and halogen;

b)

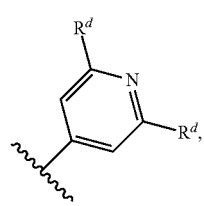

wherein R[d] is independently selected at each occurrence from hydrogen and methyl;

c)

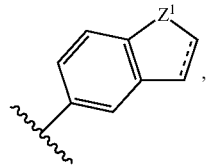

wherein, Z[1] is selected from —CH₂—, —N(H)—, —N(CH₃)—, and —N(COCH₃)—; ----- is either a single bond or a double bond; and d) cyclopropyl,

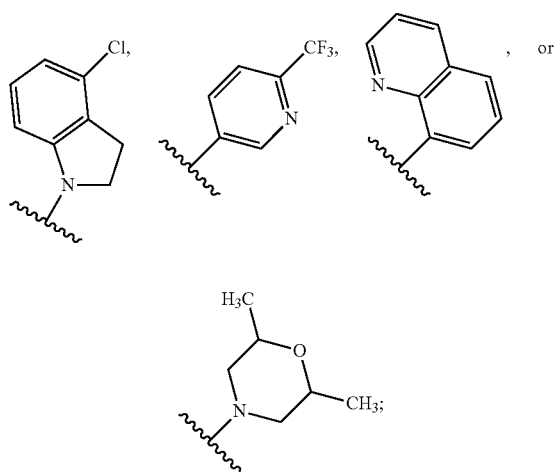

R[2] is selected from substituted- or unsubstituted-alkyl, halogen, and perhaloalkyl; or two R[2] groups and the carbon atoms to which they are attached together form a substituted- or unsubstituted-5 to 6 membered carbocycle; m is selected from 0, 1 and 2; and R[3] and R[4] are selected from hydrogen, substituted- or unsubstituted-alkyl, and R[6a]C(=O)—; or R[3], R[4] and the nitrogen to which they are attached together form a 3- to 10-membered heterocycle.

10. The compound of formula I, a tautomeric form, a stereoisomer, or a pharmaceutically acceptable salt thereof, as claimed in claim 1, wherein ring D is selected from

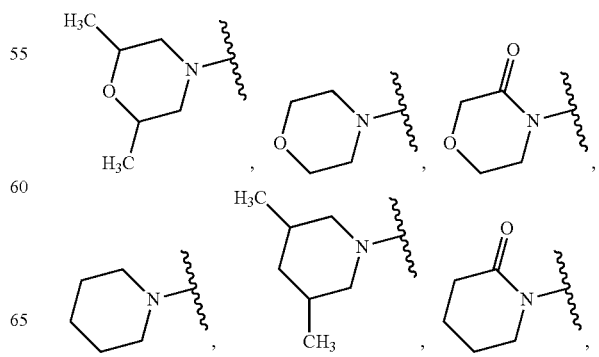

-continued

[chemical structures]

R¹ is selected from
a)

[structure with R^a, R^b, R^c]

wherein R^a is selected from halogen, cyano, cyclopropyl, methyl, trifluoromethyl, dimethylamino, H₃CS(O₂)—, H₂NC(=O)—, H₃CC(=O)N(H)—, and (CH₃)₂NC(=O)—; R^b is selected from hydrogen, halogen, cyclopropyl, and methyl; R^c is selected from hydrogen and halogen;

b)

[pyridine structure with R^d groups]

wherein R^d is independently selected at each occurrence from hydrogen and methyl;

c)

[bicyclic structure with Z¹]

wherein, Z¹ is selected from —CH₂—, —N(H)—, —N(CH₃)—, and —N(COCH₃)—; ==== is either a single bond or a double bond; and d) cyclopropyl,

[structures with Cl, CF₃, quinoline, or]

[morpholine structure with CH₃ groups]

R² is selected from methyl, fluoro, and trifluoromethyl; or two R² groups and two adjacent carbon atoms to which they are attached together form a six membered carbocycle; m is selected from 0, 1, and 2; and $R^3$ and $R^4$ are selected independently from hydrogen, methyl, and acetyl; or $R^3$, $R^4$ and the nitrogen to which they are attached together form a piperidinyl ring.

11. The compound of formula I, a tautomeric form, a stereoisomer, or a pharmaceutically acceptable salt thereof, as claimed in claim 1, wherein the compound is selected from:

(cis) 4-(4-(4-chlorophenyl)-2-(2,6-dimethylmorpholino)thiazol-5-yl)benzenesulfonamide;
4-(4-(4-chlorophenyl)-2-morpholinothiazol-5-yl)benzenesulfonamide;
4-(4-(4-chlorophenyl)-2-(4-methylpiperazin-1-yl)thiazol-5-yl)benzenesulfonamide;
4-(4-(4-chlorophenyl)-2-(piperidin-1-yl)thiazol-5-yl)benzenesulfonamide;
(cis)4-(4-(4-chlorophenyl)-2-(3,5-dimethylpiperidin-1-yl)thiazol-5-yl)benzenesulfonamide;
(cis)4-(4-cyclopropyl-2-(2,6-dimethylmorpholino)thiazol-5-yl)benzenesulfonamide;
(trans +)4-(4-(4-chlorophenyl)-2-(3,5-dimethylpiperidin-1-yl)thiazol-5-yl)benzenesulfonamide;
(trans −)-4-(4-(4-chlorophenyl)-2-(3,5-dimethylpiperidin-1-yl)thiazol-5-yl)benzenesulfonamide;
(R)-4-(4-(4-chlorophenyl)-2-(3,4-dimethylpiperazin-1-yl)thiazol-5-yl)benzenesulfonamide;
4-(4-(4-chlorophenyl)-2-(2-oxopiperidin-1-yl)thiazol-5-yl)benzenesulfonamide;
4-(4-(4-chlorophenyl)-2-(2-oxopyrrolidin-1-yl)thiazol-5-yl)benzenesulfonamide;
4-(4-(4-chlorophenyl)-2-(3-oxomorpholino)thiazol-5-yl)benzenesulfonamide;
(cis)4-(4-(4-chlorophenyl)-2-(2,6-dimethylmorpholine-4-carbonyl)thiazol-5-yl)benzenesulfonamide;
4-(4-(4-chlorophenyl)-2-(morpholine-4-carbonyl)thiazol-5-yl)benzenesulfonamide;
(+)4-(4-(4-chlorophenyl)-2-(4-methoxy-cis-3,5-dimethylpiperidine-1-carbonyl)thiazol-5-yl)benzenesulfonamide;
(−)4-(4-(4-chlorophenyl)-2-(4-methoxy-cis-3,5-dimethylpiperidine-1-carbonyl)thiazol-5-yl)benzenesulfonamide;
(trans ±) 4-(2-(2,6-bis(fluoromethyl)morpholine-4-carbonyl)-4-(4-chlorophenyl)thiazol-5-yl)benzenesulfonamide;
4-(4-(4-chlorophenyl)-2-(piperidine-1-carbonyl)thiazol-5-yl)benzenesulfonamide;
(trans ±)-4-(4-(4-chlorophenyl)-2-(3,5-dimethylpiperidine-1-carbonyl)thiazol-5-yl)benzenesulfonamide;
(cis)4-(4-(4-chlorophenyl)-2-(3,5-dimethylpiperidine-1-carbonyl)thiazol-5-yl)benzenesulfonamide;
4-(4-(4-chlorophenyl)-2-(3,3-difluoropiperidine-1-carbonyl)thiazol-5-yl)benzenesulfonamide;
4-(4-(4-chlorophenyl)-2-(4,4-difluoropiperidine-1-carbonyl)thiazol-5-yl)benzenesulfonamide;
(cis) 4-(4-(4-chlorophenyl)-2-(3,5-difluoropiperidine-1-carbonyl)thiazol-5-yl)benzenesulfonamide;
4-(4-(4-chlorophenyl)-2-(4-fluorO—cis-3,5-dimethylpiperidine-1-carbonyl)thiazol-5-yl)benzenesulfonamide;
4-(4-(4-chlorophenyl)-2-(pyrrolidine-1-carbonyl)thiazol-5-yl)benzenesulfonamide;
(S)-4-(4-(4-chlorophenyl)-2-(2-cyanopyrrolidine-1-carbonyl)thiazol-5-yl)benzenesulfonamide;
(R)-4-(4-(4-chlorophenyl)-2-(3,4-dimethylpiperazine-1-carbonyl)thiazol-5-yl)benzenesulfonamide;
(cis)4-(2-(2,6-dimethylmorpholine-4-carbonyl)-4-(4-(trifluoromethyl)phenyl)thiazol-5-yl)benzenesulfonamide;
(cis)4-(2-(2,6-dimethylmorpholine-4-carbonyl)-4-(p-tolyl)thiazol-5-yl)benzenesulfonamide;
(cis)4-(2-(2,6-dimethylmorpholine-4-carbonyl)-4-(4-fluorophenyl)thiazol-5-yl)benzenesulfonamide;
(cis)4-(4-(4-(dimethylamino)phenyl)-2-(2,6-dimethylmorpholine-4-carbonyl)thiazol-5-yl)benzenesulfonamide;
(cis)4-(2-(2,6-dimethylmorpholine-4-carbonyl)-4-(4-(methylsulfonyl)phenyl)thiazol-5-yl)benzenesulfonamide;
(cis)4-(4-(4-cyclopropylphenyl)-2-(2,6-dimethylmorpholine-4-carbonyl)thiazol-5-yl)benzenesulfonamide;
(cis) 4-(4-(4-cyanophenyl)-2-(2,6-dimethylmorpholine-4-carbonyl)thiazol-5-yl)benzenesulfonamide;
(cis) 4-(2-(2,6-dimethylmorpholine-4-carbonyl)-4-(2,6-dimethylpyridin-4-yl)thiazol-5-yl)benzenesulfonamide;
(cis)4-(2-(2,6-dimethylmorpholine-4-carbonyl)-4-(pyridin-4-yl)thiazol-5-yl)benzenesulfonamide;
(cis)4-(4-(2,4-difluorophenyl)-2-(2,6-dimethylmorpholine-4-carbonyl)thiazol-5-yl)benzenesulfonamide;
(cis)4-(4-(3,4-difluorophenyl)-2-(2,6-dimethylmorpholine-4-carbonyl)thiazol-5-yl)benzenesulfonamide;
(cis)4-(4-(4-chloro-3-cyclopropylphenyl)-2-(2,6-dimethylmorpholine-4-carbonyl)thiazol-5-yl)benzenesulfonamide;
4-(4-(4-chloro-3-methylphenyl)-2-(pyrrolidine-1-carbonyl)thiazol-5-yl)benzenesulfonamide;
(cis)4-(2-(2,6-dimethylmorpholine-4-carbonyl)-4-(1H-indol-5-yl)thiazol-5-yl)benzenesulfonamide;
(cis)4-(2-(2,6-dimethylmorpholine-4-carbonyl)-4-(1-methyl-1H-indol-5-yl)thiazol-5-yl)benzenesulfonamide;
(cis)4-(4-(2,3-dihydro-1H-inden-5-yl)-2-(2,6-dimethylmorpholine-4-carbonyl)thiazol-5-yl)benzenesulfonamide;
(cis)4-(4-(1-acetylindolin-5-yl)-2-(2,6-dimethylmorpholine-4-carbonyl)thiazol-5-yl)benzenesulfonamide;
(cis)4-(4-(4-chloroindolin-1-yl)-2-(2,6-dimethylmorpholine-4-carbonyl)thiazol-5-yl)benzenesulfonamide;
(cis)4-(4-(4-chlorophenyl)-2-(2,6-dimethylmorpholine-4-carbonyl)thiazol-5-yl)-2-methylbenzenesulfonamide;
(cis)4-(4-(4-chlorophenyl)-2-(2,6-dimethylmorpholine-4-carbonyl)thiazol-5-yl)-3-fluorobenzenesulfonamide;
(cis)4-(4-(4-chlorophenyl)-2-(2,6-dimethylmorpholine-4-carbonyl)thiazol-5-yl)-2-fluorobenzenesulfonamide;
(cis)4-(4-(4-chlorophenyl)-2-(2,6-dimethylmorpholine-4-carbonyl)thiazol-5-yl)-2-(trifluoromethyl)benzenesulfonamide;
4-(4-(4-chlorophenyl)-2-(piperidine-1-carbonyl)thiazol-5-yl)-3-fluorobenzenesulfonamide;
4-(4-(4-chlorophenyl)-2-(4,4-difluoropiperidine-1-carbonyl)thiazol-5-yl)-2-methylbenzenesulfonamide;
4-(4-(4-chlorophenyl)-2-(pyrrolidine-1-carbonyl)thiazol-5-yl)-3-fluorobenzenesulfonamide;
4-(4-(4-chlorophenyl)-2-(pyrrolidine-1-carbonyl)thiazol-5-yl)-2-fluorobenzenesulfonamide;
(cis) 4-(4-(4-chloro-3-cyclopropylphenyl)-2-(2,6-dimethylmorpholine-4-carbonyl)thiazol-5-yl)-2-methylbenzenesulfonamide;
4-(2-(8-oxa-3-azabicyclo[3.2.1]octan-3-yl)-4-(4-chlorophenyl)thiazol-5-yl)benzenesulfonamide;
4-(2-(3-oxa-8-azabicyclo[3.2.1]octan-8-yl)-4-(4-chlorophenyl)thiazol-5-yl)benzenesulfonamide;

4-(2-(6-oxa-3-azabicyclo[3.1.1]heptan-3-yl)-4-(4-chlorophenyl)thiazol-5-yl)benzenesulfonamide;
4-(2-(8-azabicyclo[3.2.1]octan-8-yl)-4-(4-chlorophenyl)thiazol-5-yl)benzenesulfonamide;
4-(2-(3-azabicyclo[3.2.1]octan-3-yl)-4-(4-chlorophenyl)thiazol-5-yl)benzenesulfonamide;
4-(2-(3-azabicyclo[3.1.0]hexan-3-yl)-4-(4-chlorophenyl)thiazol-5-yl)benzenesulfonamide;
(cis)4-(4-(4-chlorophenyl)-2-(1,5-dimethyl-3-azabicyclo[3.1.0]hexan-3-yl)thiazol-5-yl)benzenesulfonamide;
4-(4-(4-chlorophenyl)-2-(6-azaspiro[2.5]octan-6-yl)thiazol-5-yl)benzenesulfonamide;
4-(4-(4-chlorophenyl)-2-(5-azaspiro[2.5]octan-5-yl)thiazol-5-yl)benzenesulfonamide;
4-(4-(4-chlorophenyl)-2-(3,4-dihydroisoquinolin-2(1H)-yl)thiazol-5-yl)benzenesulfonamide;
4-(4-(4-chlorophenyl)-2-(3,4-dihydroquinolin-1(2H)-yl)thiazol-5-yl)benzenesulfonamide;
4-(2-(3-azabicyclo[3.1.0]hexan-3-yl)-4-(2,4-difluorophenyl)thiazol-5-yl)benzenesulfonamide;
4-(2-(8-oxa-3-azabicyclo[3.2.1]octane-3-carbonyl)-4-(4-chlorophenyl)thiazol-5-yl)benzenesulfonamide;
4-(2-(3-oxa-8-azabicyclo[3.2.1]octane-8-carbonyl)-4-(4-chlorophenyl)thiazol-5-yl)benzenesulfonamide;
4-(2-(6-oxa-3-azabicyclo[3.1.1]heptane-3-carbonyl)-4-(4-chlorophenyl)thiazol-5-yl)benzenesulfonamide;
4-(2-(8-azabicyclo[3.2.1]octane-8-carbonyl)-4-(4-chlorophenyl)thiazol-5-yl)benzenesulfonamide;
4-(2-(3-azabicyclo[3.2.1]octane-3-carbonyl)-4-(4-chlorophenyl)thiazol-5-yl)benzenesulfonamide;
(cis)4-(4-(4-chlorophenyl)-2-(1,5-dimethyl-3-azabicyclo[3.1.0]hexane-3-carbonyl)thiazol-5-yl)benzenesulfonamide;
4-(2-(3-azabicyclo[3.1.0]hexane-3-carbonyl)-4-(4-chlorophenyl)thiazol-5-yl)benzenesulfonamide;
4-(4-(4-chlorophenyl)-2-(1,2,3,4-tetrahydroquinoline-1-carbonyl)thiazol-5-yl)benzenesulfonamide;
4-(4-(4-chlorophenyl)-2-(1,2,3,4-tetrahydroisoquinoline-2-carbonyl)thiazol-5-yl)benzenesulfonamide;
4-(4-(4-chlorophenyl)-2-(6-azaspiro[2.5]octane-6-carbonyl)thiazol-5-yl)benzenesulfonamide;
4-(4-(4-chlorophenyl)-2-(5-azaspiro[2.5]octane-5-carbonyl)thiazol-5-yl)benzenesulfonamide;
4-(2-(3-azabicyclo[3.1.1]heptane-3-carbonyl)-4-(4-chlorophenyl)thiazol-5-yl)benzenesulfonamide;
4-(4-(4-chlorophenyl)-2-(4-azaspiro[2.4]heptane-4-carbonyl)thiazol-5-yl)benzenesulfonamide;
4-(2-(3-azabicyclo[3.1.0]hexane-3-carbonyl)-4-(4-chloro-3-methylphenyl)thiazol-5-yl)benzenesulfonamide;
4-(2-(3-azabicyclo[3.1.0]hexane-3-carbonyl)-5-(4-sulfamoylphenyl)thiazol-4-yl)benzamide;
N-(4-(2-(3-azabicyclo[3.1.0]hexane-3-carbonyl)-5-(4-sulfamoylphenyl)thiazol-4-yl)phenyl)acetamide;
4-(2-(3-azabicyclo[3.1.0]hexane-3-carbonyl)-5-(4-sulfamoylphenyl)thiazol-4-yl) -N,N-dimethylbenzamide;
4-(2-(3-azabicyclo[3.1.0]hexane-3-carbonyl)-4-(2,4-difluorophenyl)thiazol-5-yl)benzenesulfonamide;
4-(2-(3-azabicyclo[3.1.0]hexane-3-carbonyl)-4-(4-(trifluoromethyl)phenyl)thiazol-5-yl)benzenesulfonamide;
4-(2-(3-azabicyclo[3.1.0]hexane-3-carbonyl)-4-(4-cyclopropylphenyl)thiazol-5-yl)benzenesulfonamide;
4-(2-(3-azabicyclo[3.1.0]hexane-3-carbonyl)-4-(6-(trifluoromethyl)pyridin-3-yl)thiazol-5-yl)benzenesulfonamide;
4-(2-(3-azabicyclo[3.1.0]hexane-3-carbonyl)-4-(quinolin-8-yl)thiazol-5-yl)benzenesulfonamide;
4-(2-(3-azabicyclo[3.1.0]hexane-3-carbonyl)-4-(4-chloroindolin-1-yl)thiazol-5-yl)benzenesulfonamide;
(cis)4-(2-(3-azabicyclo[3.1.0]hexane-3-carbonyl)-4-(2,6-dimethylmorpholino)thiazol-5-yl)benzenesulfonamide;
4-(4-(1-acetylindolin-5-yl)-2-(3-azabicyclo[3.1.0]hexane-3-carbonyl)thiazol-5-yl)benzenesulfonamide;
4-(2-(3-azabicyclo[3.1.0]hexane-3-carbonyl)-4-(4-chlorophenyl)thiazol-5-yl)-N,N -dimethylbenzenesulfonamide;
3-azabicyclo[3.1.0]hexan-3-yl(4-(4-chlorophenyl)-5-(4-(piperidin-1-ylsulfonyl)phenyl)thiazol-2-yl)methanone;
4-(2-(3-azabicyclo[3.1.0]hexane-3-carbonyl)-4-(4-chlorophenyl)thiazol-5-yl)-2-methylbenzenesulfonamide;
N-((4-(2-(3-azabicyclo[3.1.0]hexane-3-carbonyl)-4-(4-chlorophenyl)thiazol-5-yl)phenyl)sulfonyl)acetamide;
4-(2-(3-azabicyclo[3.1.0]hexane-3-carbonyl)-4-(4-chlorophenyl)thiazol-5-yl)-2-(trifluoromethyl)benzenesulfonamide;
4-(2-(3-azabicyclo[3.1.0]hexane-3-carbonyl)-4-(4-chlorophenyl)thiazol-5-yl)-3-methylbenzenesulfonamide;
4-(2-(3-azabicyclo[3.1.0]hexane-3-carbonyl)-4-(4-chlorophenyl)thiazol-5-yl)-3-fluorobenzenesulfonamide;
4-(2-(3-azabicyclo[3.1.0]hexane-3-carbonyl)-4-(4-chlorophenyl)thiazol-5-yl)-2-fluorobenzenesulfonamide;
4-(2-(3-azabicyclo[3.1.0]hexane-3-carbonyl)-4-(4-chlorophenyl)thiazol-5-yl)-5,6,7,8-tetrahydronaphthalene-1-sulfonamide;
4-(2-(3-azabicyclo[3.1.0]hexane-3-carbonyl)-4-(4-chloro-3-methylphenyl)thiazol-5-yl)-2-fluorobenzenesulfonamide;
4-(2-(3-azabicyclo[3.1.0]hexan-3-ylmethyl)-4-(4-chlorophenyl)thiazol-5-yl)benzenesulfonamide;
4-(4-(4-chlorophenyl)-2-((2-oxopyrrolidin-1-yl)methyl)thiazol-5-yl)benzenesulfonamide;
4-(4-(4-chlorophenyl)-2-((2-oxopyrrolidin-1-yl)methyl)thiazol-5-yl)-3-fluorobenzenesulfonamide;
4-(4-(4-chlorophenyl)-2-((2-oxopiperidin-1-yl)methyl)thiazol-5-yl)benzenesulfonamide; and
4-(4-(4-chlorophenyl)-2-(4-phenylpiperidin-1-ypthiazol-5-yl)benzenesulfonamide.

12. A pharmaceutical composition comprising a compound of claim 1, a tautomeric form, a stereoisomer, or a pharmaceutically acceptable salt thereof, and a pharmaceutically acceptable carrier.

13. A method of treating a disease or disorder or condition mediated partially or completely by nicotinic acetylcholine receptors in a subject in need thereof, comprising administering to the subject a therapeutically effective amount of a compound of formula I, a tautomeric form, a stereoisomer, or a pharmaceutically acceptable salt thereof,

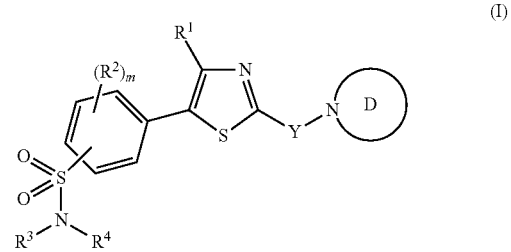

(I)

wherein, in the compound of formula I, ring D is substituted- or unsubstituted- 5 to 12 membered heterocycle optionally containing 1 to 3 additional heteroatom(s)/group(s) selected from —S(O)$_n$—, —NR$^5$—, and —O—;

ring D may be substituted on ring carbons with 1 to 6 substituent(s) independently selected from halogen, nitro, cyano, oxo, substituted- or unsubstituted-alkyl, perhaloalkyl, substituted- or unsubstituted-cycloalkyl, substituted- or unsubstituted-aryl, substituted- or unsubstituted-heteroaryl, substituted- or unsubstituted-heterocyclyl, R$^{6b}$O—, R$^6$N(H)C(=O)—, R$^{6a}$C(=O)N(H)—, R$^6$N(R$^7$)—, and R$^6$N(H)C(=O)N(H)—;

Y is a bond, —CH$_2$—, or —C(=O)—;

R$^1$ is selected from substituted- or unsubstituted-aryl, substituted- or unsubstituted-heteroaryl, substituted- or unsubstituted-cycloalkyl, and substituted- or unsubstituted-heterocyclyl;

R$^2$ is independently selected at each occurrence from halogen, nitro, cyano, substituted- or unsubstituted- alkyl, perhaloalkyl, substituted- or unsubstituted-cycloalkyl, substituted- or unsubstituted-heterocyclyl, R$^{6b}$O—, and R$^{6a}$C(=O)—, or two R$^2$ groups and the carbon atoms to which they are attached together form a 5- to 6-membered cyclic system which optionally contains 1 to 3 heteroatom(s) selected from —N—, —S—and —O—, 5- to 6-membered cyclic system may be substituted with 1 to 3 substituent(s) independently selected from oxo, halogen, cyano, and alkyl;

R$^3$ and R$^4$ are independently selected from hydrogen, R$^{6a}$C(=O)—, substituted- or unsubstituted-alkyl, substituted- or unsubstituted-cycloalkyl, and substituted- or unsubstituted-heterocyclyl; or R$^3$ and R$^4$ together with the nitrogen atom to which they are attached form a 3- to 10-membered heterocyclic ring system containing one to three heteroatom(s) selected from —S—, —N—, and —O—, said 3- to 10-membered heterocyclic ring system may be substituted with 1 to 3 substituent(s) independently selected from oxo, halogen, alkyl, OR$^{6b}$, and R$^6$N(H)—;

R$^5$ is selected from hydrogen, substituted- or unsubstituted-alkyl, substituted- or unsubstituted-cycloalkyl, substituted- or unsubstituted-aryl, substituted- or unsubstituted-heterocyclyl, R$^{6a}$C(=O)—, and R$^6$N(R$^7$)C(=O)—;

R$^6$ and R$^7$ are each independently selected from hydrogen, substituted- or unsubstituted-alkyl, substituted- or unsubstituted-cycloalkyl, and substituted- or unsubstituted-heterocyclyl;

R$^{6a}$ is selected from substituted- or unsubstituted-alkyl, perhaloalkyl, substituted- or unsubstituted-cycloalkyl, and substituted- or unsubstituted-heterocyclyl;

R$^{6b}$ is selected from hydrogen, substituted- or unsubstituted-alkyl, perhaloalkyl, substituted- or unsubstituted-cycloalkyl, and substituted- or unsubstituted-heterocyclyl;

m is an integer selected from 0, 1, 2, and 3;

n is an integer selected from 0, 1, and 2;

when the alkyl group is a substituted alkyl group, the alkyl group is substituted with 1 to 4 substituents selected independently from oxo, halogen, nitro, cyano, perhaloalkyl, substituted- or unsubstituted-cycloalkyl, substituted- or unsubstituted-aryl, substituted- or unsubstituted-heteroaryl, substituted- or unsubstituted-heterocyclyl, R$^{8b}$O—, R$^{8a}$S(O$_2$)—, R$^{8a}$OC(=O)—, R$^{8a}$C(=O)O—, R$^8$N(H)C(=O)—, R$^8$N(alkyl)C(=O)—, R$^{8a}$C(=O)N(H)—, R$^8$N(H)—, R$^8$N(alkyl)-, R$^8$N(H)C(=O)N(H)—, and R$^8$N(alkyl)C(=O)N(H)—;

when the cycloalkyl and the carbocyclic groups are substituted, each of them is substituted with 1 to 3 substituents selected independently from oxo, halogen, nitro, cyano, substituted- or unsubstituted-alkyl, perhaloalkyl, substituted- or unsubstituted-aryl, substituted- or unsubstituted-heteroaryl, substituted- or unsubstituted-heterocyclyl, R$^{8b}$O—, R$^{8c}$S(O$_2$)—, R$^{8c}$C(=O)—, R$^{8c}$OC(=O)—, R$^{8c}$C(=O)O—, R$^{8d}$N(H)C(=O)—, R$^{8d}$N(alkyl)C(=O)—, R$^{8c}$C(=O)N(H)—, R$^{8d}$N(H)—, R$^{8d}$N(alkyl)-, R$^{8d}$N(H)C(=O)N(H)—, and R$^{8d}$N(alkyl)C(=O)N(H)—;

when the aryl group is substituted, it is substituted with 1 to 3 substituents selected independently from halogen, nitro, cyano, hydroxy, substituted- or unsubstituted-alkyl, perhaloalkyl, substituted- or unsubstituted-cycloalkyl, substituted- or unsubstituted-heterocycle, (alkyl)O—, (perhaloalkyl)O—, (alkyl)N(alkyl)-, (alkyl)N(H)—, H$_2$N—, (alkyl)S(O$_2$)—, (perhaloalkyl)S(O$_2$)—, (alkyl)C(=O)N(alkyl)-, (alkyl)C(=O)N(H)—, (alkyl)N(alkyl)C(=O)—, (alkyl)N(H)C(=O)—, H$_2$NC(=O)—, (alkyl)N(alkyl)S(O$_2$)—, (alkyl)N(H)S(O$_2$)—, and H$_2$NS(O$_2$)—;

when the heteroaryl group is substituted, it is substituted with 1 to 3 substituents selected independently from halogen, nitro, cyano, hydroxy, substituted- or unsubstituted-alkyl, perhaloalkyl, substituted- or unsubstituted-cycloalkyl, substituted- or unsubstituted-heterocycle, (alkyl)O—, (perhaloalkyl)O—, (alkyl)N(alkyl)-, (alkyl)N(H)—, H$_2$N—, (alkyl)S(O$_2$)—, (perhaloalkyl)S(O$_2$)—, (alkyl)C(=O)N(alkyl)-, (alkyl)C(=O)N(H)—, (alkyl)N(alkyl)C(=O)—, (alkyl)N(H)C(=O)—, H$_2$NC(=O)—, (alkyl)N(alkyl)S(O$_2$)—, (alkyl)N(H)S(O$_2$)—, and H$_2$NS(O$_2$)—;

when the heterocyclic group is substituted, it can be substituted either on a ring carbon atom or on a ring hetero atom, and when the heterocyclic group is substituted on a ring carbon atom, it is substituted with 1-3 substituents selected independently from halogen, nitro, cyano, oxo, substituted- or unsubstituted-alkyl, perhaloalkyl, substituted- or unsubstituted-cycloalkyl, substituted- or unsubstituted-aryl, substituted- or unsubstituted-heteroaryl, substituted- or unsubstituted-heterocyclyl, R$^{8b}$O—, R$^{8c}$OC(=O)—, R$^{8c}$C(=O)O—, R$^{8d}$N(H)C(=O)—, R$^{8d}$N(alkyl)C(=O)—, R$^{8c}$C(=O)N(H)—, R$^{8d}$N(H)—, R$^{8d}$N(alkyl)-, R$^{8d}$N(H)C(=O)N(H)—, and R$^{8d}$N(alkyl)C(=O)N(H)—; when the heterocyclic group is substituted on a ring nitrogen, it is substituted with a substituent selected from substituted- or unsubstituted-alkyl, substituted- or unsubstituted-cycloalkyl, substituted- or unsubstituted-aryl, substituted- or unsubstituted-heteroaryl, R$^{8a}$S(O$_2$)—, R$^{8a}$C(=O)—, R$^{8a}$OC(=O)—, R$^8$N(H)C(=O)—, and R$^8$N(alkyl)C(=O)—;

R$^8$ is selected from hydrogen, alkyl, cycloalkyl, aryl, heteroaryl, and heterocyclyl;

R$^{8a}$ is selected from alkyl, perhaloalkyl, cycloalkyl, aryl, heteroaryl, and heterocyclyl;

R$^{8b}$ is selected from hydrogen, alkyl, perhaloalkyl, cycloalkyl, aryl, heteroaryl, and heterocyclyl;

R$^{8c}$ is selected from alkyl, perhaloalkyl, and cycloalkyl; and

R$^{8d}$ is selected from hydrogen, alkyl, and cycloalkyl.

14. The method of claim 13, wherein the disorder or condition or disease is selected from Alzheimer's disease, mild cognitive impairment, senile dementia, vascular dementia, dementia of Parkinson's disease, attention deficit disorder, attention deficit hyperactivity disorder, dementia associated with Lewy bodies, AIDS dementia complex, Pick's disease, dementia associated with Down's syndrome, Huntington's disease, cognitive deficits associated with traumatic brain injury, cognitive decline associated with stroke, poststroke neuroprotection, cognitive and sensorimotor gating deficits associated with schizophrenia, cognitive deficits associated with bipolar disorder, cognitive impairments associated with depression, acute pain, post-surgical or post-operative pain, chronic pain, inflammation, inflammatory pain, neuropathic pain, smoking cessation, need for new blood vessel growth associated with wound healing, need for new blood vessel growth associated with vascularization of skin grafts, and lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, and rheumatoid spondylitis.

15. The method of claim 13, wherein the disease or disorder or condition is selected from the group classified or diagnosed as major or minor neurocognitive disorders, or disorders arising due to neurodegeneration.

16. The method of claim 13, comprising administering a compound of formula I, a tautomeric form, a stereoisomer, or a pharmaceutically acceptable salt thereof, in combination with or as adjunct to medications utilized in the treatment of attention deficit hyperactivity disorders, schizophrenia, cognitive disorders such as Alzheimer's disease, Parkinson's dementia, vascular dementia or dementia associated with Lewy bodies, or traumatic brain injury.

17. The method of claim 13, further comprising administering a compound of formula I, a tautomeric form, a stereoisomer, or a pharmaceutically acceptable salt thereof, in combination with or as an adjunct to acetylcholinesterase inhibitors, disease modifying drugs or biologics for neurodegenerative disorders, dopaminergic drugs, antidepressants, or a typical or an atypical antipsychotic.

* * * * *

UNITED STATES PATENT AND TRADEMARK OFFICE
CERTIFICATE OF CORRECTION

PATENT NO. : 9,388,196 B2
APPLICATION NO. : 14/379134
DATED : July 12, 2016
INVENTOR(S) : Sinha et al.

Page 1 of 1

It is certified that error appears in the above-identified patent and that said Letters Patent is hereby corrected as shown below:

In the claims,

Column 83, line 60:

4-(4-(4-chlorophenyl)-2-(4-fluorO-cis-3,5-dimethylpipshould read:

4-(4-(4-chlorophenyl)-2-(4-fluoro-cis-3,5-dimethylpip-.

Column 86, line 43:

4-(4-(4-chlorophenyl)-2-(4-phenylpiperidin-1-ypthiazolshould read:

4-(4-(4-chlorophenyl)-2-(4-phenylpiperidin-1-yl)thiazol-.

Signed and Sealed this
Twenty-third Day of August, 2016

Michelle K. Lee
*Director of the United States Patent and Trademark Office*